United States Patent
Radeke et al.

(10) Patent No.: US 7,485,283 B2
(45) Date of Patent: *Feb. 3, 2009

(54) CONTRAST AGENTS FOR MYOCARDIAL PERFUSION IMAGING

(75) Inventors: Heike S. Radeke, South Grafton, MA (US); David S. Casebier, Carlisle, MA (US); Michael T. Azure, Henniker, NH (US); Douglas D. Dischino, Middlefield, CT (US)

(73) Assignee: Lantheus Medical Imaging, N. Billerica, MA (US)

( * ) Notice: Subject to any disclaimer, the term of this patent is extended or adjusted under 35 U.S.C. 154(b) by 322 days.

This patent is subject to a terminal disclaimer.

(21) Appl. No.: 11/113,486

(22) Filed: Apr. 25, 2005

(65) Prior Publication Data
US 2005/0244332 A1 Nov. 3, 2005

Related U.S. Application Data

(60) Provisional application No. 60/566,146, filed on Apr. 28, 2004.

(51) Int. Cl.
*A61K 51/00* (2006.01)
*A61M 36/14* (2006.01)

(52) U.S. Cl. .................. 424/1.89; 424/1.11; 424/1.65; 424/1.81; 424/1.85; 540/1

(58) Field of Classification Search .............. 424/1.11, 424/1.37, 1.65, 1.81, 1.85, 1.89, 9.1, 9.3, 424/9.4, 9.5, 9.6, 9.7, 9.8; 540/1; 549/200
See application file for complete search history.

(56) References Cited

U.S. PATENT DOCUMENTS

| | | | |
|---|---|---|---|
| 3,359,103 A * | 12/1967 | Foris et al. .................. 430/17 |
| 5,087,440 A | 2/1992 | Cacheris | |
| 5,088,499 A | 2/1992 | Unger | |
| 5,155,215 A | 10/1992 | Ranney | |
| 5,228,446 A | 7/1993 | Unger et al. | |
| 5,281,704 A | 1/1994 | Love et al. | |
| 5,412,148 A | 5/1995 | Keana | |
| 5,417,959 A | 5/1995 | Wallace | |
| 5,520,904 A | 5/1996 | Nosco et al. | |
| 5,547,656 A | 8/1996 | Unger | |
| 5,567,411 A | 10/1996 | Keana et al. | |
| 5,585,112 A | 12/1996 | Unger et al. | |
| 5,679,810 A | 10/1997 | Love et al. | |
| 5,760,191 A | 6/1998 | Snow et al. | |
| 5,801,228 A | 9/1998 | Hollister et al. | |
| 5,804,161 A | 9/1998 | Long et al. | |
| 5,846,517 A | 12/1998 | Unger | |
| 6,565,889 B2 * | 5/2003 | Zasadzinski et al. ........ 424/490 |

| | | |
|---|---|---|
| 2003/0044354 A1 | 3/2003 | Carpenter, Jr. et al. |
| 2004/0033197 A1 | 2/2004 | Madar et al. |
| 2004/0034239 A1 | 2/2004 | Nicolaou et al. |
| 2005/0191238 A1 | 9/2005 | Casbier et al. |

FOREIGN PATENT DOCUMENTS

| | | |
|---|---|---|
| EP | 0727225 A2 | 8/1996 |
| WO | WO 91/14460 | 10/1991 |
| WO | WO 92/17215 | 10/1992 |
| WO | WO 94/22496 | 10/1994 |
| WO | WO 02/20008 A1 | 3/2002 |
| WO | WO 03/086476 | 10/2003 |

OTHER PUBLICATIONS

Walker, John E., "The NADH: ubiquinone oxidoreductase (complex I) of respiratory chains," Quarterly Review of Biophysics, vol. 25, No. 3, pp. 253-324 (1992).
Esposti, Mauro D., "Inhibitors of NADH—ubiquinone reductase: an overview," Biochimica et Biophysica Acta, vol. 1364, pp. 222-235 (1998).
Brown, Michael et al., "Delineation of myocardial oxygen utilization with carbon -11—labeled acetate," Circulation, vol. 76, No. 3, pp. 687-696 (1987).
Krivokapich, Janine et al., "13N Ammonia Myocardial Imaging at Rest and With Exercise in Normal Volunteers, Quantification of Absolute Myocardial Perfusion With Dynamic Positron Emission Tomography," Circulation, vol. 80, No. 5, pp. 1328-1337 (1989).
Pauwels, E.K.J. et al., "Fluorine-18-radiolabeled pharmaceuticals for imaging with positron emission tomography, excluding [18F]-fluorodeoxyglucose," Drugs of the Future, vol. 27, pp. 655-667 (2002).
Magerstadt, Michael et al., "Gd(DOTA): An Alternative to Gd(DTPA) as a T1,2 Relaxation Agent for NMR Imaging of Spectroscopy," Magnetic Resonance in Medicine, vol. 3, pp. 808-812 (1986).
Runge, Val M. et al., "MR Imaging of Rat Brain Glioma: Gd-DTPA versus Gd-DOTA." Radiology, vol. 166, No. 3, pp. 835-838 (1988).
Bousquet, Jean-Claude, et al., "Gd-DOTA: Characterization of a New Paramagnetic Complex," Radiology, vol. 166, No. 3, pp. 693-698 (1988).
Nicolaou, KC, et al., "Combinatorial synthesis of novel and potent inhibitors of NADH:ubiquinone oxidoreductase," Chemistry & Biology, vol. 7, pp. 979-992, (2000).
Lindell, Stephen D. et al, "The design and synthesis of novel inhibitors of NADH:ubiquinone oxidoreductase," Bioorganic & Medicinal Chemistry Letters, vol. 14, pp. 511-514 (2004).
Schuler, F. et al., "Functional coupling of PSST and NDl subunits in NADH: ubiquinone oxidoreductase established by photoaffintiy labeling," Biochimica et Biophysica Acta 2001, *1506,* 79-87.

\* cited by examiner

*Primary Examiner*—D. L Jones
(74) *Attorney, Agent, or Firm*—Wolf Greenfield & Sacks, P.C.

(57) ABSTRACT

The present disclosure is directed, in part, to compounds and methods for imaging myocardial perfusion, comprising administering to a patient a contrast agent which comprises a compound that binds MC-1, and an imaging moiety, and scanning the patient using diagnostic imaging.

3 Claims, No Drawings

CONTRAST AGENTS FOR MYOCARDIAL PERFUSION IMAGING

CROSS REFERENCE TO RELATED APPLICATION

The present application claims the benefit of priority under 35 U.S.C. § 119(e) from the provisional application U.S. Ser. No. 60/566,146 filed Apr. 28, 2004.

CONTRAST AGENTS FOR MYOCARDIAL PERFUSION IMAGING

The present disclosure relates to novel compounds comprising imaging moieties, and their use for diagnosing certain disorders in a patient.

Mitochondria are membrane-enclosed organelles distributed through the cytosol of most eukaryotic cells. Mitochondria are especially concentrated in myocardium tissue.

Complex 1 ("MC-1") is a membrane-bound protein complex of 46 dissimilar subunits. This enzyme complex is one of three energy-transducing complexes that constitute the respiratory chain in mammalian mitochondria. This NADH-ubiquinone oxidoreductase is the point of entry for the majority of electrons that traverse the respiratory chain, eventually resulting in the reduction of oxygen to water (*Q. Rev. Biophys.* 1992, 25, 253-324).

Known inhibitors of MC-1 include deguelin, piericidin A, ubicidin-3, rolliniastatin-1, rolliniastatin-2 (bullatacin), capsaicin, pyridaben, fenpyroximate, amytal, MPP+, quinolines, and quinolones (BBA 1998, 1364,222-235).

The present disclosure is based, in part, on the recognition that interrupting the normal function of mitochondria could advantageously concentrate certain compounds in the mitochondria, and hence in the mitochondria-rich myocardium tissue. If these compounds were labeled with an imaging moiety, such a build up could be detected, thereby providing valuable diagnostic markers for myocardial perfusion imaging. For purposes of this specification, a compound is referred to as "labeled" when an imaging moiety which is attached to the compound.

In one embodiment the present disclosure provides a contrast agent comprising an imaging moiety and an annonaceous acetogenin, a quinone acetogenin, a substituted chromone, and an open-chain deguelin analog.

In another embodiment the present disclosure provides a contrast agent comprising an imaging moiety and an annonaceous acetogenin. Annonaceous acetogenins are a class of compounds typified by an aliphatic chain functionalized at one end with a furanone. Initially isolated from the plant class *Annonaceae*, they are reported to have high activity against a variety of tumor cell lines, and very high inhibition versus MC-1. The class is commonly divided into three categories based on central portions of the molecule: adjacent bis tetrahydrofarans, non-adjacent bis tetrahydrofurans, and monotetrahydrofurans, with the relative activity descending in that order (Nakanishi, 2003).

Experimental evidence indicates the configuration of the adjacent tetrahydrofuran rings is not a key contributing factor for SAR (structure activity relationship) (Miyoshi, 1998). For example, the inhibitory activities of trilobacin and bullatacin shown below reported as $IC_{50}$ of MC-1, are identical to one another within experimental error.

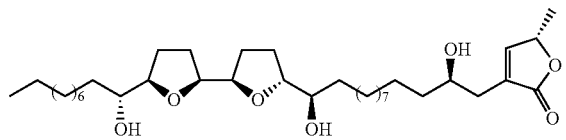

Trilobacin: 1.4nM

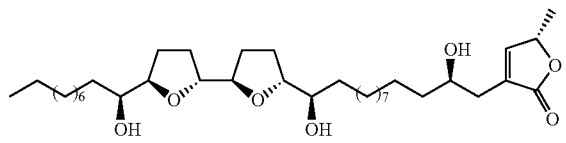

Bullatacin: 1.2nM

Other examples of annonaceous acetogenins with adjacent tetrahydrofuran rings include:

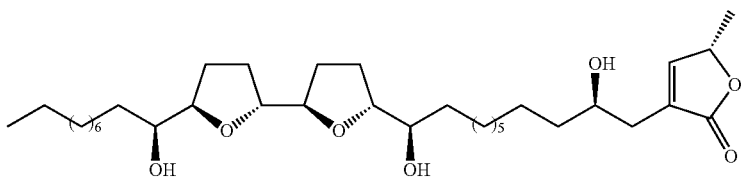

Molvizarin

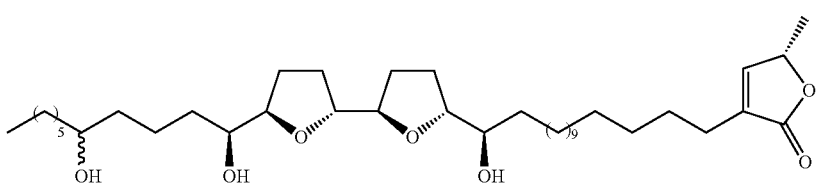

Squamocin: 1.6nM

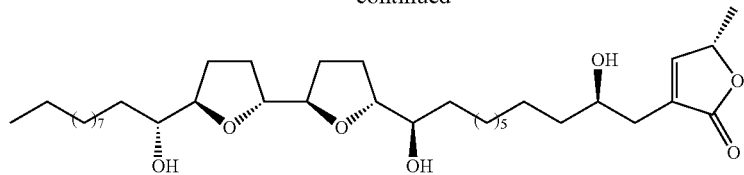

Parviflorin: 1.9nM

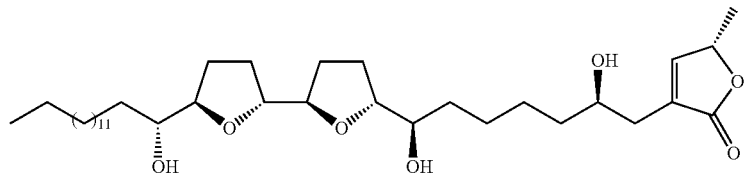

Longimicin C: 19nM

Annonaceous acetogenins with non-adjacent bis tetrahydrofurans typically have a pair of tetrahydrofurans linked by a carbon chain of a length of C-4 to C-8. Again, the relative stereochemistry does not seem to have a profound effect as shown by the high activity of both bullatalicin and sylvaticin below. These compounds differ only by the THF ring fusion and the hydroxyl chirality (trans:threo vs. cis:threo).

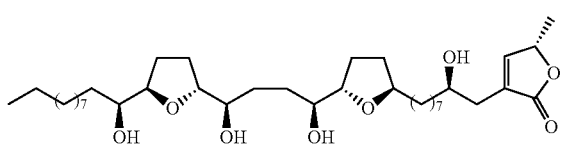

Bullatalicin: 1.6nM

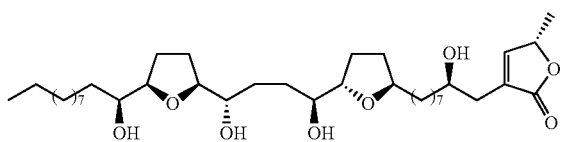

Sylvaticin: 1.4nM

While the monotetrahydrofuran annonaceous acetogenins tend to be less active, they still possess remarkable activity, and offer a synthetically easier target. Examples of annonaceous acetogenins with a monotetrahydrofuran ring include:

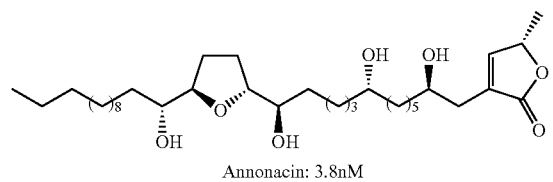

Annonacin: 3.8nM

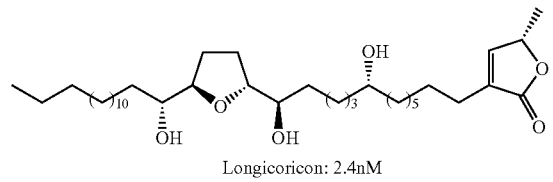

Longicoricon: 2.4nM

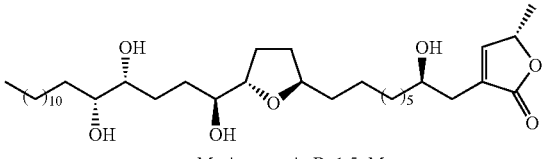

Muricatetrocin B: 1.5nM

Substitution of the lactone-furan linker at other than the 4-position or alpha to the furan rings typically lowers activity. In the case of murihexocin, is drastically alters the potency of the compound:

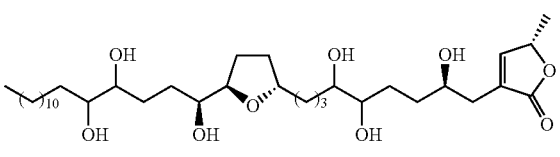

Murihexocin: 330nM

Recently, a group published a report of ethylene glycol ethers as a replacement for the bis-THF moiety (Jiang, 2002). These compounds have excellent antitumor properties, but they have not been tested against MC-1 directly. Presumably, they would show good activity, and are the most straightforward to synthesize:

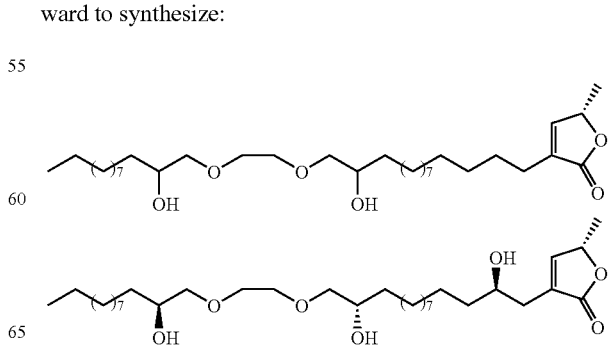

Thus, in one embodiment of the present disclosure, the contrast agent is of formula (I)

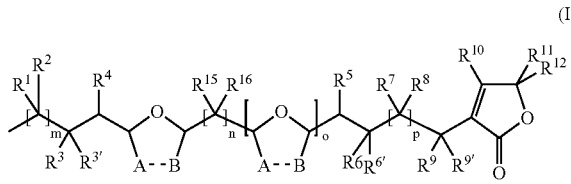

wherein
- m is 1, 2, 3, 4, 5, 6, 7, 8, 9, 10, 11, 12, 13, or 14;
- n is 0, 1, 2, 3, 4, 5, 6, 7, or 8;
- o is 0 or 1;
- p is 5, 6, 7, 8, 9, 10, 11, or 12;
- - - - is absent or a single bond;
- when - - - is absent, A and B are independently selected from hydrogen and an imaging moiety;
- when - - - is a single bond, A and B are each $(C(R^1)_2)_k$;
- k is 1 or 2, provided that when A and B are each $(C(R^1)_2)_k$, one k is 1 and the other is 1 or 2;
- $R^1$, $R^2$, $R^4$, $R^5$, $R^7$, $R^8$, $R^{10}$, $R^{15}$, and $R^{16}$ are independently at each occurrence hydrogen, hydroxy, or an imaging moiety;
- $R^3$ is hydrogen, hydroxy, or an imaging moiety;
- $R^{3'}$ is hydrogen; or
- $R^3$ and $R^{3'}$, together with the carbon atom to which they are attached, form C=O or C=$CR^{13}R^{14}$;
- $R^6$ is hydrogen, hydroxy, or an imaging moiety;
- $R^{6'}$ is hydrogen; or
- $R^6$ and $R^{6'}$, together with the carbon atom to which they are attached, form C=O or C=$CR^{13}R^{14}$;
- $R^9$ is hydrogen, hydroxy, or an imaging moiety;
- $R^{9'}$ is hydrogen; or
- $R^9$ and $R^{9'}$, together with the carbon atom to which they are attached, form C=O or C=$CR^{13}R^{14}$;
- $R^{11}$ is $C_1$-$C_6$ alkyl; and
- $R^{12}$, $R^{13}$, and $R^{14}$, are independently hydrogen, $C_1$-$C_6$ alkyl optionally substituted with an imaging moiety, arylalkyl, or an imaging moiety; provided that at least one imaging moiety is present in formula (I).

In another embodiment $R^4$ is an imaging moiety.
In another embodiment $R^5$ is an imaging moiety.
In another embodiment $R^8$ is an imaging moiety.
In another embodiment $R^9$ is an imaging moiety.

In another embodiment the present disclosure provides a contrast agent comprising an imaging moiety and an annonaceous acetogenin wherein the contrast agent is

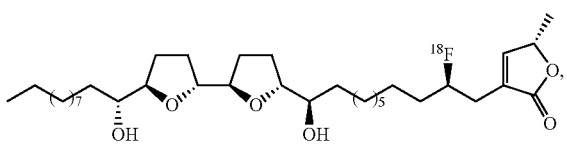

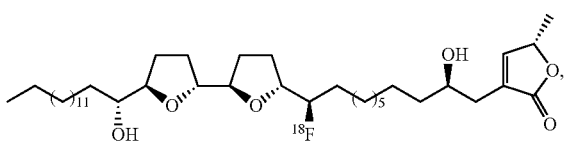

or

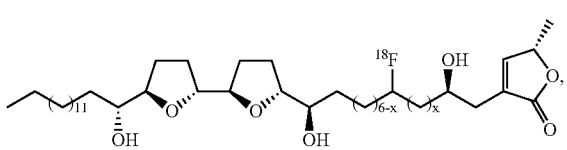

wherein x is 0, 1, 2, 3, 4, 5, or 6.

In another embodiment the present disclosure provides a contrast agent comprising an imaging moiety an annonaceous acetogenin wherein the contrast agent is

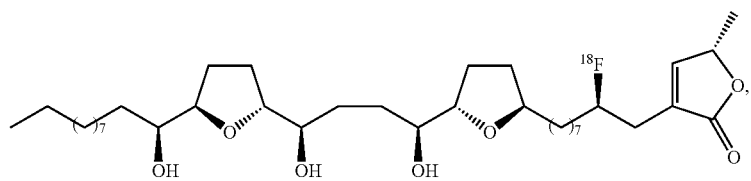

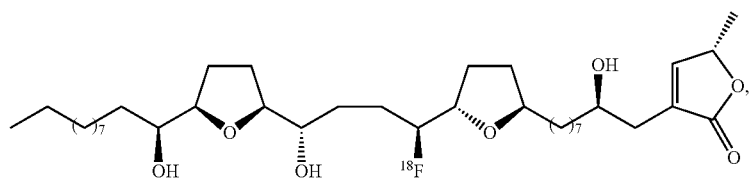

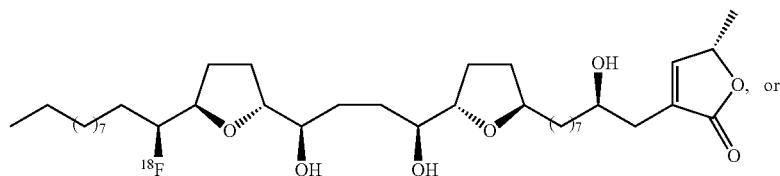

-continued

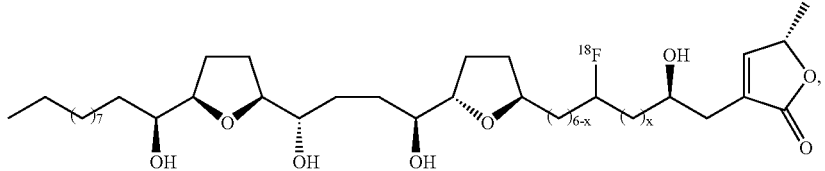

wherein x is 0, 1, 2, 3, 4, 5, or 6.

In another embodiment the present disclosure provides a contrast agent comprising an imaging moiety and an annonaceous acetogenin wherein the contrast agent is

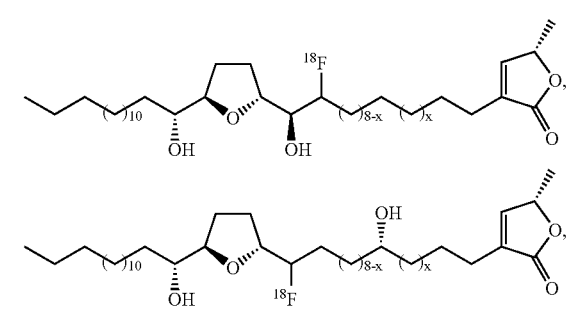

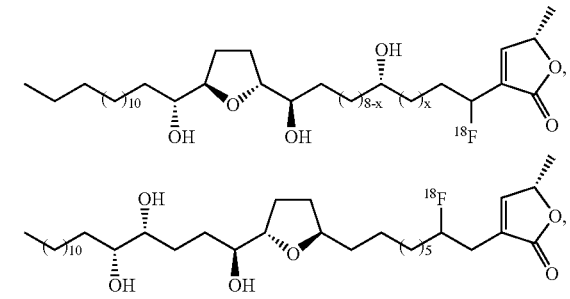

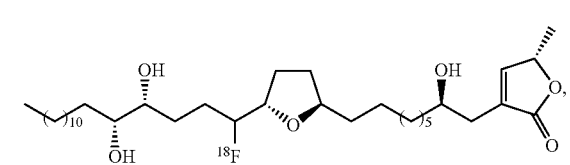

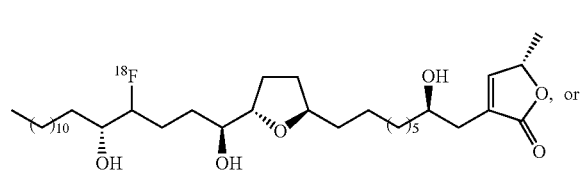

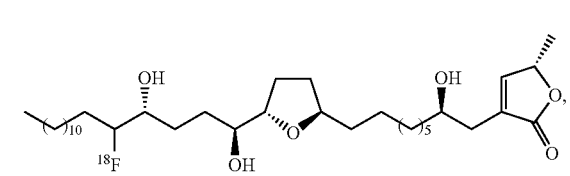

wherein x is 0, 1, 2, 3, 4, 5, 6, 7, or 8.

In another embodiment the present disclosure provides a contrast agent comprising an imaging moiety and an annonaceous acetogenin wherein the contrast agent is

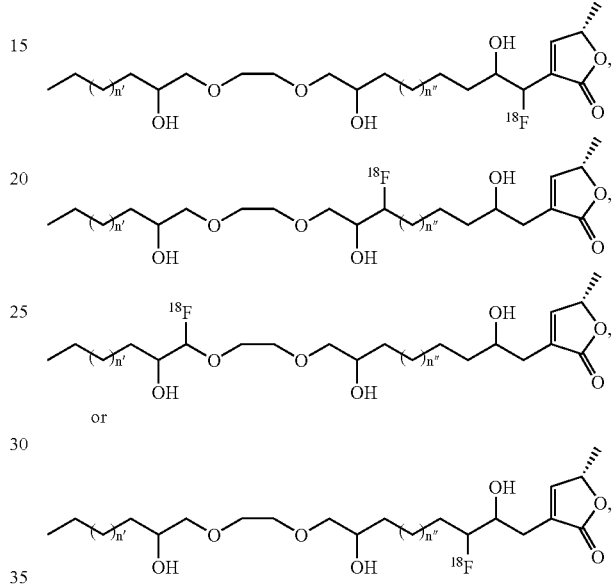

or

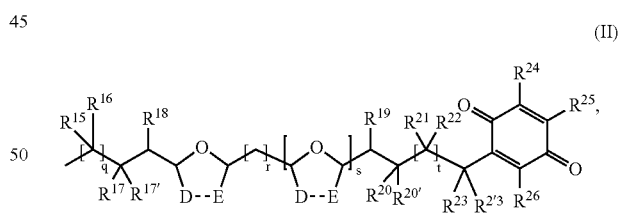

wherein n' is independently at each occurrence 0, 1, 2, 3, 4, 5, 6, 7, 8, 9, or 10; and where n" is independently at each occurrence 2, 3, 4, 5, 6, 7, 8, 9, or 10.

In another embodiment the present disclosure provides a contrast agent comprising an imaging moiety a quinone acetogenin wherein the contrast agent is of formula (II)

(II)

wherein
q is 1, 2, 3, 4, 5, 6, 7, 8, 9, 10, 11, 12, 13, or 14;
r is 0, 1, 2, 3, 4, 5, 6, 7, or 8;
s is 0 or 1;
t is 5, 6, 7, 8, 9, 10, 11, or 12;
- - - is absent or a single bond;
when - - - is absent, D and E are independently selected from hydrogen and an imaging moiety;
when - - - is a single bond, D and E are each $(C(R^{15})_2)_u$;
u is 1 or 2, provided that when D and E are each $(C(R^{15})_2)$, one u is 1 and the other is 1 or 2;
$R^{15}, R^{16}, R^{18}, R^{19}, R^{21}$, and $R^{22}$, are independently at each occurrence hydrogen, hydroxy, or an imaging moiety;

$R^{17}$ is hydrogen, hydroxy, or an imaging moiety;

$R^{17'}$ is hydrogen; or $R^{17}$ and $R^{17'}$, together with the carbon atom to which they are attached, form C=O or C=$CR^{27}R^{28}$;

$R^{20}$ is hydrogen, hydroxy, or an imaging moiety;

$R^{20'}$ is hydrogen; or $R^{20}$ and $R^{20'}$, together with the carbon atom to which they are attached, form C=O or C=$CR^{27}R^{28}$;

$R^{23}$ is hydrogen, hydroxy, or an imaging moiety;

$R^{23'}$ is hydrogen; or $R^{23}$ and $R^{23'}$, together with the carbon atom to which they are attached, form C=O or C=$CR^{27}R^{28}$;

$R^{24}$, $R^{25}$, and $R^{26}$ are independently hydrogen, $C_1$-$C_6$ alkyl optionally substituted with an imaging moiety, $C_1$-$C_6$ alkoxy, hydroxy, halo, or an imaging moiety; and $R^{27}$ and $R^{28}$ are independently hydrogen, $C_1$-$C_6$ alkyl optionally substituted with an imaging moiety, arylalkyl, an imaging moiety; provided that at least one imaging moiety is present in formula (II).

In another embodiment $R^{18}$, $R^{19}$, $R^{22}$, or $R^{23}$ is an imaging moiety.

In another embodiment $R^{22}$ is an imaging moiety.

In another embodiment the present disclosure provides a contrast agent comprising an imaging moiety and a quinone acetogenin wherein the contrast agent is

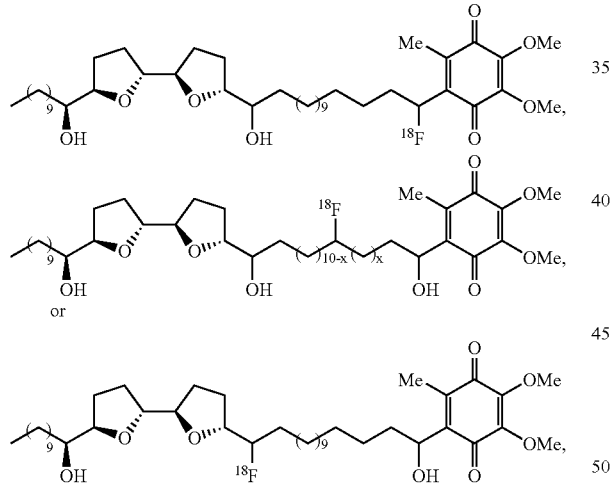

wherein x is 0, 1, 2, 3, 4, 5, 6, 7, 8, 9, or 10.

In another embodiment the present disclosure provides a contrast agent comprising an imaging agent and an open-chain deguelin analog. Recently, Nicoloau and coworkers (Nicoloau, K. C.; Pfefferkomn, J. A.; Schuler, F.; Roecker, A. J.; Cao, G.-Q.; Casida, J. E. Combinatorial Synthesis of Novel and Potent Inhibitors of NADH:Ubiquinone Oxidoreductase Chemistry & Biology 2000, 7, 979-992; Nicoloau, K. C.; Pfefferkorn, J. A.; Roecker, A. J.; Cao, G.-Q. Inhibitors of NADH:Ubiquinone Oxidoreductase PCT WO 02/20008A1) described several highly selective inhibitors for MC-1 based upon the gross pharmacophoric layout of deguelin.

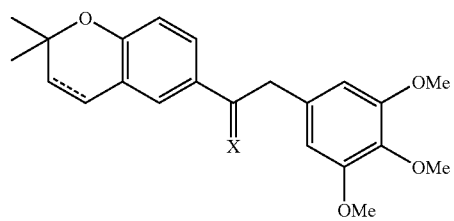

X = O, unsat'd: 39nM
X = O sat'd: 24 nM
X = CH2 unsat'd: 19 nM
X = CH2 sat'd: 18nM Using standard screening and optimization methods, they were able to construct a class of compounds with a wide range of activities, some with reasonably low affinity/inhibition of MC-1. These compounds were made for the purposes of chemoprotective/chemotherapeutic applications. Further examples include the incorporation of labile functionalities, that could allow for the rapid metabolism of the molecule from circulating plasma, clearing background signal from perfused material:

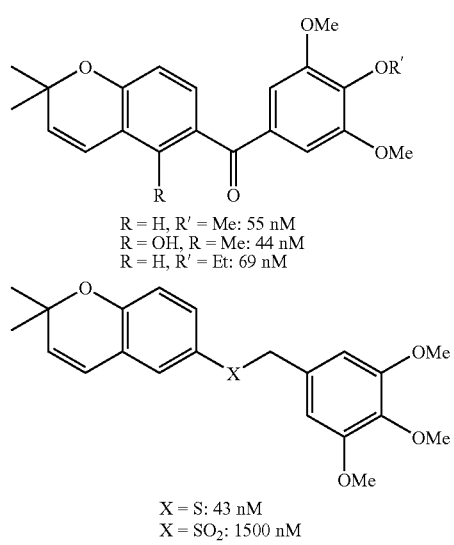

R = H, R' = Me: 55 nM
R = OH, R = Me: 44 nM
R = H, R' = Et: 69 nM

X = S: 43 nM
X = $SO_2$: 1500 nM

Thus, in another embodiment the present disclosure provides a contrast agent comprising an imaging moiety and an open-chain deguelin analog wherein the contrast agent is of formula (III)

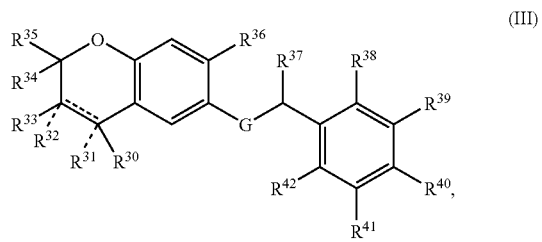

(III)

wherein

G is —S—, —O—,

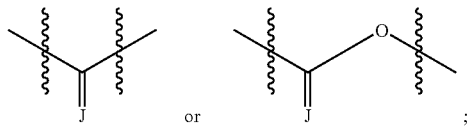

or

J is S. C(R$^{37}$)$_2$, or O;

----- is a single or double bond; and
R$^{30}$, R$^{31}$, R$^{32}$, R$^{33}$, R$^{34}$, R$^{35}$, R$^{36}$, R$^{37}$, R$^{38}$, R$^{39}$, R$^{40}$, R$^{41}$, and R$^{42}$ are independently at each occurance hydrogen, C$_1$-C$_6$ alkyl optionally substituted with an imaging moiety, C$_1$-C$_6$ alkoxy optionally substituted with an imaging moiety, or an imaging moiety; provided that when

----- is a double bond, R$^{31}$ and R$^{32}$ are absent; and provided at least one imaging moiety is present in formula (III).

In another embodiment R$^{36}$, R$^{37}$, R$^{38}$, or R$^{42}$ is an imaging moiety.

In another embodiment R$^{38}$ is an imaging moiety.

In another embodiment the present disclosure provides a contrast agent comprising an imaging moiety and an open-chain deguelin analog wherein the contrast agent is

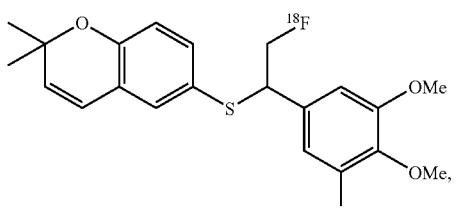

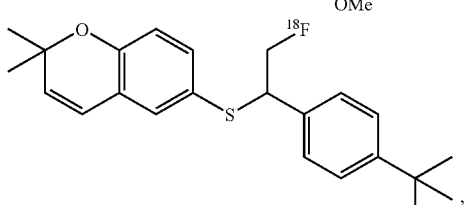

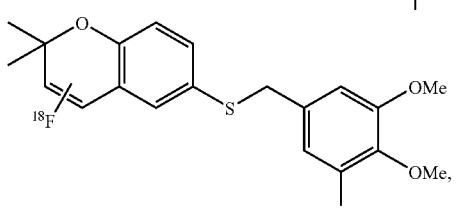

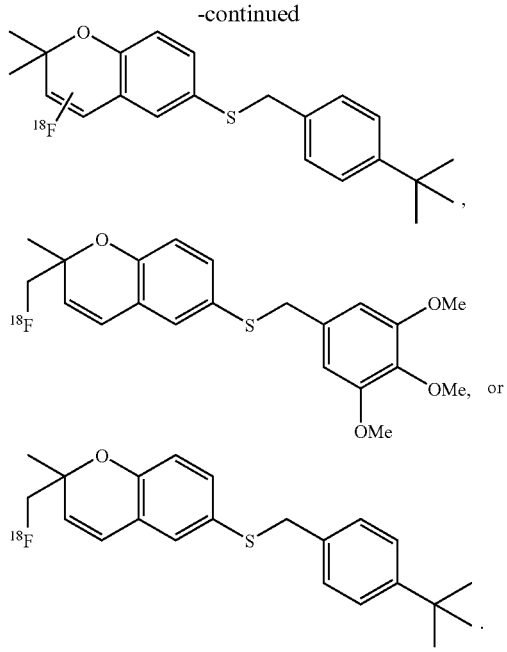

In another embodiment the present disclosure provides a contrast agent comprising an imaging moiety and an open-chain deguelin analog wherein the contrast agent is

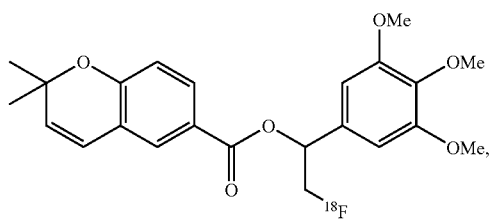

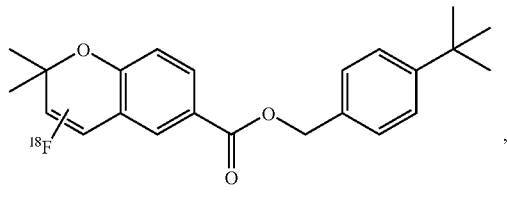

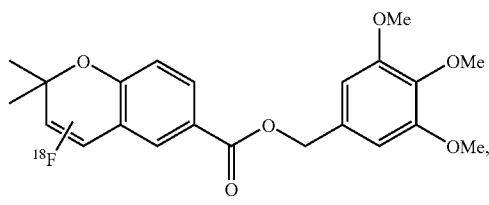

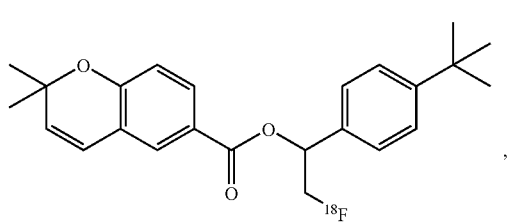

-continued

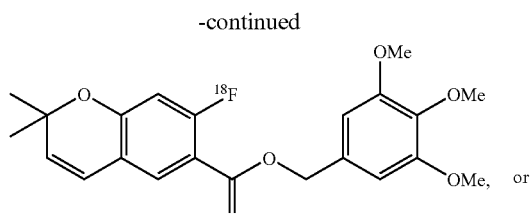

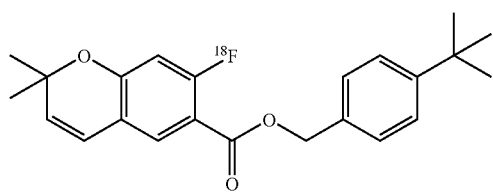

In another embodiment the present disclosure provides a contrast agent comprising an imaging moiety and an open-chain deguelin analog wherein the contrast agent is

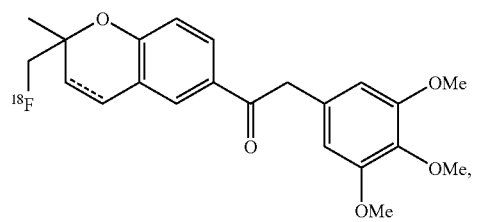

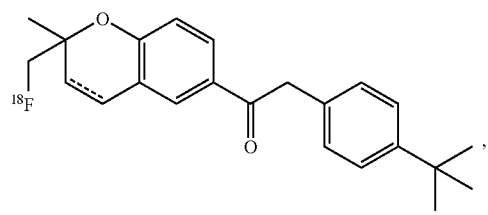

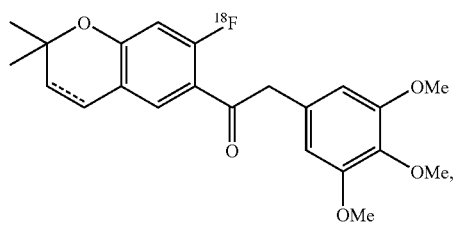

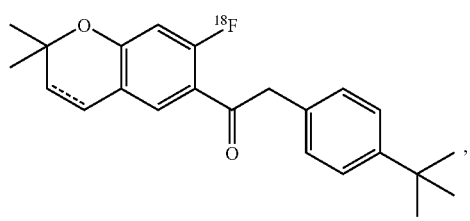

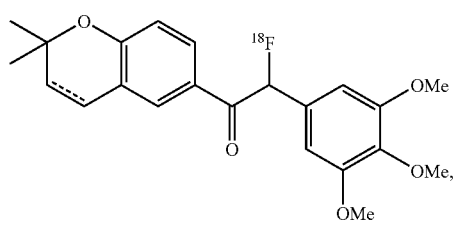

-continued

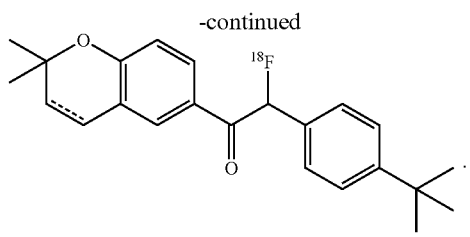

In another embodiment the present disclosure provides a contrast agent comprising an imaging moiety and an open-chain deguelin analog wherein the contrast agent is

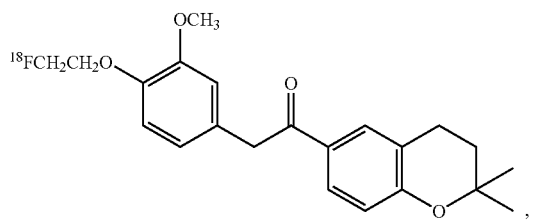

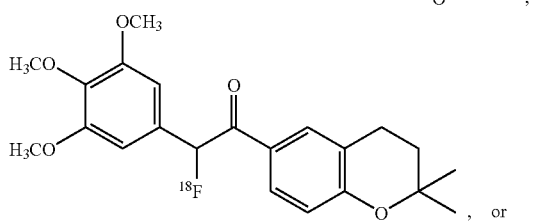

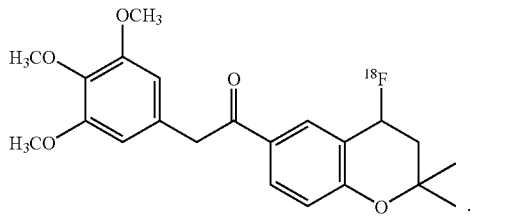

In another embodiment the present disclosure provides a contrast agent comprising an imaging agent and a substituted chromone. Recently, Lindell and co-workers (*Bioorg. Med. Chem. Letters* 2004, 14, 511-514) described a series of substituted chromones that are highly selective inhibitors for MC-I. These compounds comprise similar activity to the known commercial acaricide pyridaben (Sanmite™), a highly active MC-I inhibitor, with similar sidechain SAR requirements incorporated into the molecule.

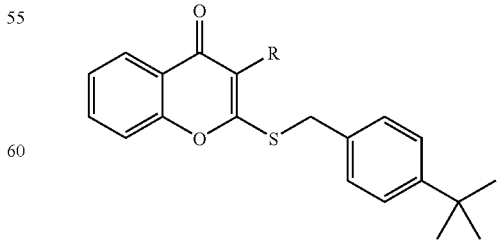

R = H, Me
MC-I IC$_{50}$ = 500 & 8 nM respectively

Thus, in another embodiment the present disclosure provides a contrast agent comprising an imaging moiety and a substituted chromone wherein the contrast agent is of formula (IV)

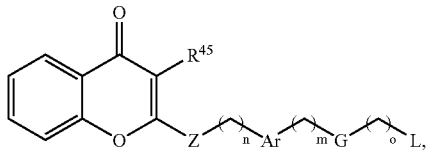

wherein n, m, and o are independently 1, 2, 3, or 4;

Z is O, S, or $NR^{46}$;

$R^{45}$ is an imaging moiety or $C_1$-$C_4$ alkyl optionally substituted with an imaging moiety;

$R^{46}$ is hydrogen or $C_1$-$C_3$ alkyl;

Ar is phenyl, furyl, thienyl, oxazolinyl, isoxazolinyl, thiazolyl, isothiazolyl, pyridyl, naphthyl, pyrimidinyl, or pyrazinyl;

G is absent or O; and

L is an imaging moiety; provided that when G is absent, o is 3.

In another embodiment the present disclosure provides a contrast agent comprising an imaging moiety and a substituted chromone wherein the contrast agent is

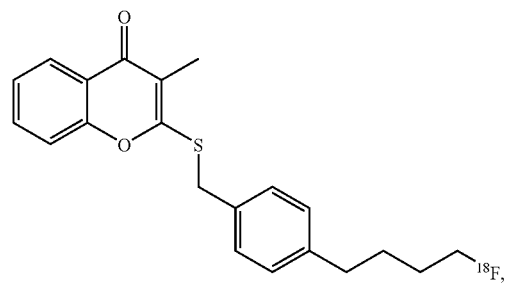

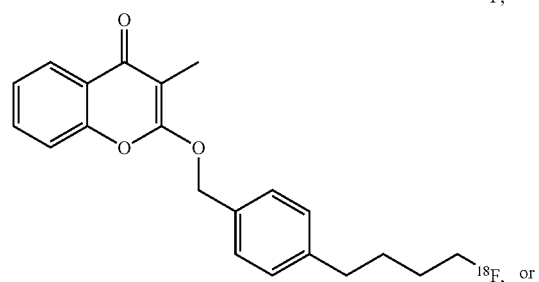

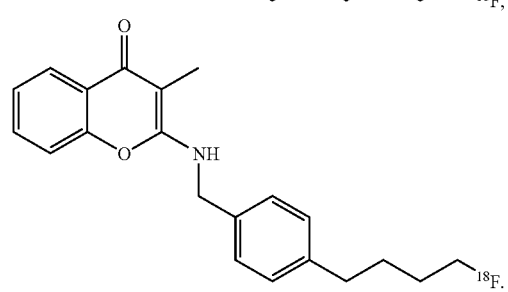

In another embodiment the present disclosure provides a contrast agent comprising an imaging moiety and a substituted chromone wherein the contrast agent is

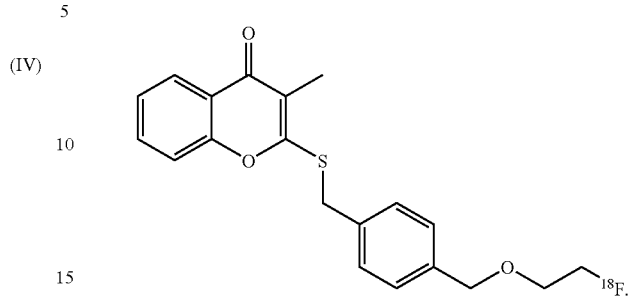

In another embodiment the present disclosure provides a contrast agent comprising an imaging moiety and a compound selected from an annonaceous acetogenin, a quinone acetogenin, a substituted chromone, and an open-chain deguelin analog wherein the imaging moiety is a radioisotope for nuclear medicine imaging, a paramagnetic species for use in MRI imaging, an echogenic entity for use in ultrasound imaging, a fluorescent entity for use in fluorescence imaging, or a light-active entity for use in optical imaging.

In another embodiment the imaging moiety is a paramagnetic species for use in MRI imaging wherein the paramagnetic species is $Gd^{3+}$, $Fe^{3+}$, $In^{3+}$, or $Mn^{2+}$.

In another embodiment the imaging moiety is an echogenic entity for use in ultrasound imaging wherein the echogenic entity is a fluorocarbon encapsulated surfactant microsphere.

In another embodiment the imaging moiety is a radioisotope for nuclear medicine imaging wherein the radioisotope is $^{11}C$, $^{13}N$, $^{18}F$, $^{123}I$, $^{124}I$, $^{125}I$, $^{99m}Tc$, $^{95}Tc$, $^{111}In$, $^{76}Br$, $^{62}Cu$, $^{64}Cu$, $^{67}Ga$, or $^{68}Ga$. In another embodiment the imaging moiety is $^{18}F$. In another embodiment the imaging moiety is $^{99m}Tc$.

In another embodiment the present disclosure provides a method of imaging myocardial perfusion comprising administering to a patient a contrast agent which comprises an imaging moiety and a compound selected from an annonaceous acetogenin, a quinone acetogenin, a substituted chromone, and an open-chain deguelin analog; and scanning the patient using diagnostic imaging. In another embodiment the imaging moiety is a radioisotope for nuclear medicine imaging, a paramagnetic species for use in MRI imaging, an echogenic entity for use in ultrasound imaging, a fluorescent entity for use in fluorescence imaging, or a light-active entity for use in optical imaging.

In another embodiment the present disclosure provides a contrast agent comprising an imaging moiety and capsaicin or a derivative thereof.

Imaging Moieties

Nuclear medicine contrast agents of the present disclosure include $^{11}C$, $^{13}N$, $^{18}F$, $^{123}I$, $^{124}I$, $^{125}I$, $^{99m}Tc$, $^{95}Tc$, $^{111}In$ $^{76}Br$, $^{62}Cu$, $^{64}Cu$, $^{67}Ga$, and $^{68}Ga$. $^{11}C$-Palmitate has been used to probe fatty acid oxidation and $^{11}C$-acetate has been used to assess oxidative metabolism in the myocardium (*Circulation* 1987, 76, 687-696). $^{13}N$-Ammonia has been used widely to image myocardial perfusion (*Circulation* 1989, 80, 1328-37). Agents based on $^{18}F$ have been used as imaging agents for hypoxia and cancer (*Drugs of the Future* 2002, 27,655-667). 15-($^{123}I$)-iodophenyl)-pentadecanoic acid and 15-(p-($^{123}I$)-iodophenyl)-3(R,S)-methylpentadecanoic acid are two iodinated agents that have been used for imaging myocardial metabolism. In one embodiment, the imaging moiety employed in the present contrast agents is $^{18}$F. Further imaging moieties of the present disclosure may be comprised of one or more X-ray absorbing or "heavy" atoms of atomic number 20 or greater, further comprising an optional linking moiety, L, between the parent molecular moiety and the X-ray absorbing atoms. A frequently used heavy atom in X-ray contrast agents is iodine. Recently, X-ray contrast agents comprised of metal chelates (U.S. Pat. No. 5,417,959) and polychelates comprised of a plurality of metal ions (U.S. Pat. No. 5,679,810) have been disclosed. More recently, multinuclear cluster complexes have been disclosed as X-ray contrast agents (U.S. Pat. No. 5,804,161, WO 91/14460, and WO 92/17215). In certain embodiments of the present disclosure the specific metals used in the X-ray contrast agents include Re, Sm, Ho, Lu, Pm, Y, Bi, Pd, Gd, La, Au, Yb, Dy, Cu, Rh, Ag, and Ir.

MRI contrast agents of the present disclosure may be comprised of one or more analog moieties attached to one or more paramagnetic metal ions, further comprising an optional linking moiety, L, between the analog moieties and the paramagnetic metal ions. The paramagnetic metal ions may be present in the form of metal chelates or complexes or metal oxide particles. U.S. Pat. Nos. 5,412,148, and 5,760,191, describe examples of chelators for paramagnetic metal ions for use in MRI contrast agents. U.S. Pat. No. 5,801,228, U.S. Pat. No. 5,567,411, and U.S. Pat. No. 5,281,704, describe examples of polychelants useful for complexing more than one paramagnetic metal ion for use in MRI contrast agents. U.S. Pat. No. 5,520,904, describes particulate compositions comprised of paramagnetic metal ions for use as MRI contrast agents. Examples of specific metals include $Gd^{3+}$, $Fe^{3+}$, $In^{3+}$, and $Mn^{2+}$.

The ultrasound contrast agents of the present disclosure may comprise a plurality of analog moieties attached to or incorporated into a microbubble of a biocompatible gas, a liquid carrier, and a surfactant microsphere, further comprising an optional linking moiety, L, between the analog moieties and the microbubble. In this context, the term "liquid carrier" means aqueous solution and the term "surfactant" means any amphiphilic material which may produce a reduction in interfacial tension in a solution. A list of suitable surfactants for forming surfactant microspheres is disclosed, for example, in EP0727225A2. The term "surfactant microsphere" includes microspheres, nanospheres, liposomes, vesicles and the like. The biocompatible gas can be any physiologically accepted gas, including, for example, air, or a fluorocarbon, such as a $C_3$-$C_5$ perfluoroalkane, which provides the difference in echogenicity and thus the contrast in ultrasound imaging. The gas may be encapsulated, contained, or otherwise constrained in or by the microsphere to which is attached the analog moiety, optionally via a linking group. The attachment can be covalent, ionic or by van der Waals forces. Specific examples of such contrast agents include, for example, lipid encapsulated perfluorocarbons with a plurality of tumor neovasculature receptor binding peptides, polypeptides or peptidomimetics. Examples of gas filled imaging moieties include those found in U.S. patent application Ser. No. 09/931,317, filed Aug. 16, 2001, and U.S. Pat. Nos. 5,088,499, 5,547,656, 5,228,446, 5,585,112, and 5,846,517.

Chelators

Many approaches to labeling compounds with $^{99m}$Tc are known, including direct labeling of the compound or inclusion of a chelating moiety ("chelator"). In one embodiment, the chelator is DADT, MAG3, MAMA, PAMA, or DOTA.

The compounds of the disclosure may optionally contain a chelator ("C"). In certain embodiments of the compounds of the disclosure, the chelator is a surfactant capable of forming an echogenic substance-filled lipid sphere or microbubble. In certain other embodiments, the chelator is a bonding unit having a formula selected from

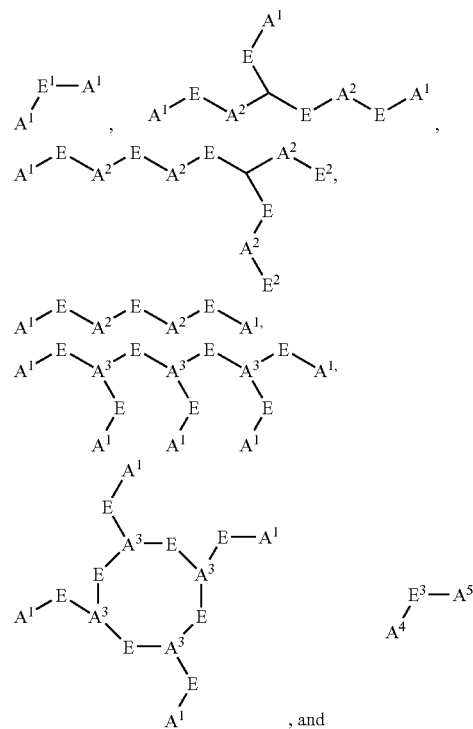

wherein
each $A^1$ is independently selected from —$NR^{46}R^{47}$, —$NHR^{53}$, —SH, —S(Pg), —OH, —$PR^{46}R^{47}$, —P(O)$R^{48}R^{49}$, and a bond to the compound that binds MC-1;
each $A^2$ is independently selected from $N(R^{53})$, $N(R^{46})$, S, O, $P(R^{46})$, and —OP(O)($R^{48}$)O—;
$A^3$ is N;
$A^4$ is selected from OH and OC(=O)$C_1$-$C_{20}$ alkyl;
$A^5$ is OC(=O)$C_1$-$C_{20}$ alkyl;
each E is independently selected from $C_1$-$C_{16}$ allylene substituted with 0-3 $R^{50}$, $C_6$-$C_{10}$ arylene substituted with 0-3 $R^{50}$, $C_3$-$C_{10}$ cycloalkylene substituted with 0-3 $R^{50}$, heterocyclyl-$C_1$-$C_{10}$ alkylene substituted with 0-3 $R^{50}$, $C_6$-$C_{10}$ aryl-$C_1$-$C_{10}$ alkylene substituted with 0-3 $R^{50}$, and heterocyclylene substituted with 0-3 $R^{50}$;
$E^1$ is selected from a bond and E;
each $E^2$ is independently selected from $C_1$-$C_{16}$ alkyl substituted with 0-3 $R^{50}$, $C_6$-$C_{10}$ aryl substituted with 0-3 $R^{50}$, $C_3$-$C_{10}$ cycloalkyl substituted with 0-3 $R^{50}$, heterocyclyl-$C_1$-$C_{10}$ alkyl substituted with 0-3 $R^{50}$, $C_6$-$C_{10}$ aryl-$C_1$-$C_{10}$ alkyl substituted with 0-3 $R^{50}$, $C_1$-$C_{10}$ alkyl-$C_6$-$C_{10}$ aryl substituted with 0-3 $R^{50}$, and heterocyclyl substituted with 0-3 $R^{50}$;
$E^3$ is $C_1$-$C_{10}$ alkylene substituted with 1-3 $R^{59}$;
Pg is a thiol protecting group;
$R^{46}$ and $R^{47}$ are each independently selected from a bond to the compound that binds MC-1, hydrogen, $C_1$-$C_{10}$ alkyl substituted with 0-3 $R^{50}$, aryl substituted with 0-3 $R^{50}$, $C_3$-$C_{10}$ cycloalkyl substituted with 0-3 $R^{50}$, heterocyclyl-$C_1$-$C_{10}$ alkyl substituted with 0-3 $R^{50}$, $C_6$-$C_{10}$ aryl-$C_1$-$C_{10}$ alkyl substituted with 0-3 $R^{50}$, and heterocyclyl substituted with 0-3 $R^{50}$;

$R^{48}$ and $R^{49}$ are each independently selected from a bond to the compound that binds MC-1, —OH, $C_1$-$C_{10}$ alkyl substituted with 0-3 $R^{50}$, aryl substituted with 0-3 $R^{50}$, $C_3$-$C_{10}$ cycloalkyl substituted with 0-3 $R^{50}$, heterocyclyl-$C_1$-$C_{10}$ alkyl substituted with 0-3 $R^{50}$, $C_6$-$C_{10}$ aryl-$C_1$-$C_{10}$ alkyl substituted with 0-3 $R^{50}$, and heterocyclyl substituted with 0-3 $R^{50}$;

each $R^{50}$ is independently selected from a bond to the compound that binds MC-1, =O, halo, trifluoromethyl, cyano, —$CO_2R^{51}$, —C(=O)$R^{51}$, —C(=O)N($R^{51}$)$_2$, —CHO, —$CH_2OR^{51}$, —OC(=O)$R^{51}$, —OC(=O)O$R^{51}$, —O$R^{51}$, —OC(=O)N($R^{51}$)$_2$, —$NR^{51}$C(=O)$R^{51}$, —$NR^{51}$C(=O)O$R^{51}$, —$NR^{51}$C(=O)N($R^{51}$)$_2$, —$NR^{51}$SO$_2$N($R^{51}$)$_2$, —$NR^{51}$SO$_2R^{51}$, —$SO_3H$, —$SO_2R^{51}$, —$SR^{51}$, —S(=O)$R^{51}$, —$SO_2$N($R^{51}$)$_2$, —N($R^{51}$)$_2$, —NHC(=S)$NHR^{51}$, =$NOR^{51}$, $NO_2$, —C(=O)$NHOR^{51}$, —C(=O)NH(N($R^{51}$)$_2$, —$OCH_2CO_2H$, 2-(1-morpholino)ethoxy, $C_1$-$C_5$ alkyl, $C_2$-$C_4$ alkenyl, $C_3$-$C_6$ cycloalkyl, $C_3$-$C_6$ cycloalkylmethyl, $C_2$-$C_6$ alkoxyalkyl, aryl substituted with 0-2 $R^{51}$, and heterocyclyl;

each $R^{51}$ is independently selected from a bond to the compound that binds MC-1, hydrogen, $C_1$-$C_6$ alkyl, phenyl, benzyl, and $C_{1-6}$ alkoxy;

$R^{53}$ is a co-ordinate bond to a metal;

each $R^{59}$ selected from $R^{61}$, =O, —$CO_2R^{60}$, —C(=O)$R^{60}$, —C(=O)N($R^{60}$)$_2$, —$CH_2OR^{60}$, —$OR^{60}$, —N($R^{60}$)$_2$, and $C_2$-$C_4$ alkenyl;

each $R^{60}$ is independently selected from $R^{61}$, hydrogen, $C_1$-$C_6$ alkyl, phenyl, benzyl, and trifluoromethyl; and $R^{61}$ is a bond to the compound that binds MC-1;

wherein at least one of $A^1$, $R^{46}$, $R^{47}$, $R^{48}$, $R^{49}$, $R^{50}$, $R^{51}$, and $R^{61}$ is a bond to the compound that binds MC-1.

Methods of Making

Typically $^{18}$F labeled compounds are synthesized by $S_n2$ displacement of an appropriate leaving group. These leaving groups are preferably sulfonic acid esters such as toluenesulfonate (tosylate, TsO), methanesulfonate (mesylate, MsO), or trifluoromethanesulfonate (triflate, TfO). The leaving group may also be a halide, a phosphineoxide (via Mitsunobu reaction), or an internal leaving group (such as an epoxide or cyclic sulfate). These compounds are made from highly activated, dry $K^{18}F$, that is made "hotter" by the addition of cryptands such as krytofix[2.2.2]. Purification is generally via salt removal by reverse-phase chromatography (Sep-Pak).

Representative methods of making the contrast agents are described in the following examples. The foregoing chemical transformations may be conducted using techniques which would be readily apparent to one of ordinary skill in the art, once armed with the teachings in the present applications. Representative reaction solvents include, for example, DMF, NMP, DMSO, THF, ethyl acetate, dichloromethane, and chloroform. The reaction solution may be kept neutral or basic by the addition of an amine such as triethylamine or DIEA. Reactions may be carried out at ambient temperatures and protected from oxygen and water with a nitrogen atmosphere.

Temporary protecting groups may be used to prevent other reactive functionality, such as amines, thiols, alcohols, phenols, and carboxylic acids, from participating in the reaction. Representative amine protecting groups include, for example, tert-butoxycarbonyl and trityl (removed under mild acidic conditions), Fmoc (removed by the use of secondary amines such as piperidine), and benzyloxycarbonyl (removed by strong acid or by catalytic hydrogenolysis). The trityl group may also used for the protection of thiols, phenols, and alcohols. In certain embodiments the carboxylic acid protecting groups include, for example, tert-butyl ester (removed by mild acid), benzyl ester (usually removed by catalytic hydrogenolysis), and alkyl esters such as methyl or ethyl (usually removed by mild base). All protecting groups may be removed at the conclusion of synthesis using the conditions described above for the individual protecting groups, and the final product may be purified by techniques which would be readily apparent to one of ordinary skill in the art, once armed with the present disclosure.

Annonaceous acetogenins have been made synthetically by rather long routes (Naito, 1995; Hoye, 1995, 1996, 1997), as well as several unnatural bis-THF analogs (Sasaki, 1998; Kuwabara, 2000). The preceding compounds could be made via the nucleophilic ring opening of an epoxide. These epoxides could conveniently be made through epoxidation of an olefin within the aliphatic chain:

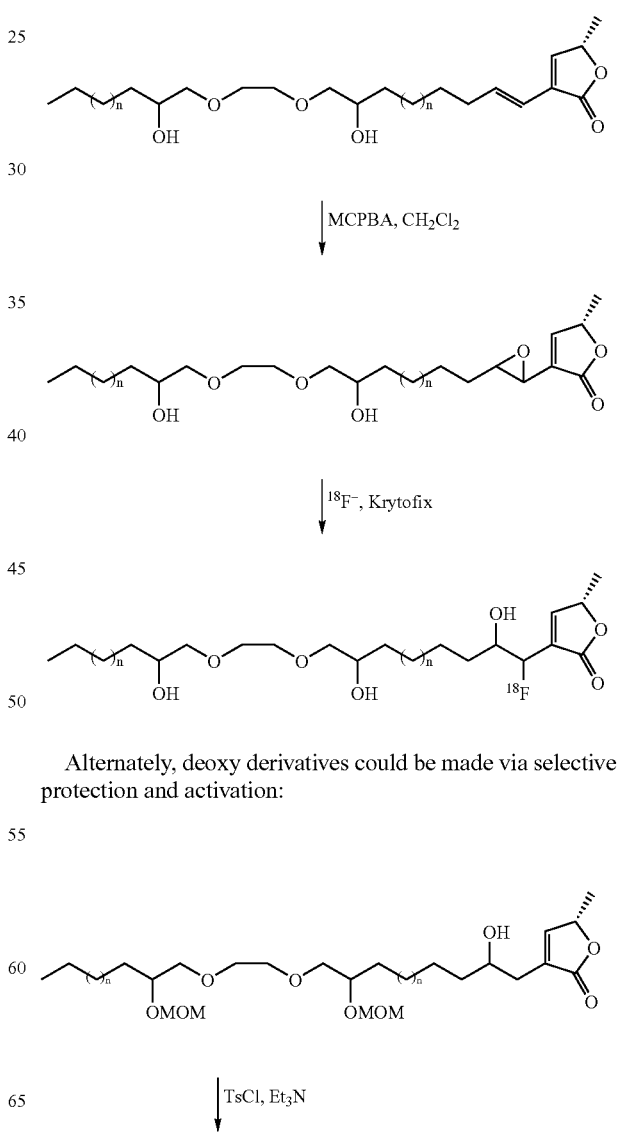

Alternately, deoxy derivatives could be made via selective protection and activation:

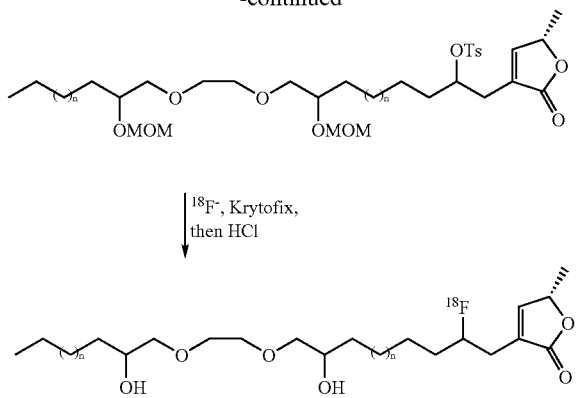

Use

The contrast agents of the present disclosure may be used in a method of imaging, including methods of imaging in a patient comprising administering the contrast agent to the patient by injection, infusion, or any other known method, and imaging the area of the patient wherein the event of interest is located.

The useful dosage to be administered and the particular mode of administration will vary depending upon such factors as age, weight, and particular region to be treated, as well as the particular contrast agent used, the diagnostic use contemplated, and the form of the formulation, for example, suspension, emulsion, microsphere, liposome, or the like, as will be readily apparent to those skilled in the art.

Typically, dosage is administered at lower levels and increased until the desirable diagnostic effect is achieved. In one embodiment, the above-described contrast agents may be administered by intravenous injection, usually in saline solution, at a dose of about 0.1 to about 100 mCi per 70 kg body weight (and all combinations and subcombinations of dosage ranges and specific dosages therein), or preferably at a dose of about 0.5 to about 50 mCi. Imaging is performed using techniques well known to the ordinarily skilled artisan.

For use as nuclear medicine contrast agents, the compositions of the present disclosure, dosages, administered by intravenous injection, will typically range from about 0.5 µmol/kg to about 1.5 mmol/kg (and all combinations and subcombinations of dosage ranges and specific dosages therein), preferably about 0.8 µmol/kg to about 1.2 mmol/kg.

For use as MRI contrast agents, the compositions of the present disclosure may be used in a similar manner as other MRI agents as described in U.S. Pat. No. 5,155,215; U.S. Pat. No. 5,087,440; *Magn. Reson. Med.* 1986, 3, 808; *Radiology* 1988, 166, 835; and *Radiology* 1988, 166, 693. Generally, sterile aqueous solutions of the contrast agents may be administered to a patient intravenously in dosages ranging from about 0.01 to about 1.0 mmols per kg body-weight (and all combinations and subcombinations of dosage ranges and specific dosages therein).

The ultrasound contrast agents of the present disclosure may be administered by intravenous injection in an amount from about 10 to about 30 µL (and all combinations and subcombinations of dosage ranges and specific dosages therein) of the echogenic gas per kg body weight or by infusion at a rate of approximately 3 µL/kg/min.

Another aspect of the present disclosure is diagnostic kits for the preparation of diagnostic agents for detecting, imaging, and/or monitoring myocardial perfusion. Diagnostic kits of the present disclosure comprise one or more vials containing the sterile, non-pyrogenic, formulation comprising a predetermined amount of a reagent of the present disclosure, and optionally other components such as one or two ancillary ligands such as tricine and 3-[bis(3-sulfophenyl)phosphine]benzenesulfonic acid (TPPTS), reducing agents, transfer ligands, buffers, lyophilization aids, stabilization aids, solubilization aids and bacteriostats. The kits may also comprise a reducing agent, such as, for example, tin(II).

Buffers useful in the preparation of contrast agents and kits include, for example, phosphate, citrate, sulfosalicylate, and acetate buffers. A more complete list can be found in the United States Pharmacopoeia.

Lyophilization aids useful in the preparation of contrast agents and kits include, for example, mannitol, lactose, sorbitol, dextran, FICOLL® polymer, and polyvinylpyrrolidine (PVP).

Stabilization aids useful in the preparation of contrast agents and kits include, for example, ascorbic acid, cysteine, monothioglycerol, sodium bisulfite, sodium metabisulfite, gentisic acid, and inositol.

Solubilization aids useful in the preparation of contrast agents and kits include, for example, ethanol, glycerin, polyethylene glycol, propylene glycol, polyoxyethylene sorbitan monooleate, sorbitan monoloeate, polysorbates, poly(oxyethylene)-poly(oxypropylene)-poly(oxyethylene) block copolymers ("Pluronics") and lecithin. In certain embodiments the solubilizing aids are polyethylene glycol and Pluronics.

Bacteriostats useful in the preparation of contrast agents and kits include, for example, benzyl alcohol, benzalkonium chloride, chlorbutanol, and methyl, propyl, or butyl paraben.

A component in a diagnostic kit can also serve more than one function. For example, a reducing agent for a radionuclide can also serve as a stabilization aid, or a buffer can also serve as a transfer ligand, or a lyophilization aid can also serve as a transfer, ancillary, or co-ligand.

The compounds herein described may have asymmetric centers. Unless otherwise indicated, all chiral, diastereomeric and racemic forms are included in the present disclosure. Many geometric isomers of olefins, C═N double bonds, and the like can also be present in the compounds described herein, and all such stable isomers are contemplated in the present disclosure. It will be appreciated that compounds of the present disclosure may contain asymmetrically substituted carbon atoms, and may be isolated in optically active or racemic forms. It is well known in the art how to prepare optically active forms, such as by resolution of racemic forms or by synthesis from optically active starting materials. Two distinct isomers (cis and trans) of the peptide bond are known to occur; both can also be present in the compounds described herein, and all such stable isomers are contemplated in the present disclosure. The D- and L-isomers of a particular amino acid are designated herein using the conventional 3-letter abbreviation of the amino acid, as indicated by the following examples: D-Leu, or L-Leu.

For the sake of simplicity, connection points ("-") are not depicted. When an atom or compound is described to define a variable, it is understood that it is intended to replace the variable in a manner to satisfy the valency of the atom or compound. For example, if a variable A" was identified as $C(R^{80})=C(R^{80})$, both carbon atoms would form a part of the chain in order to satisfy their respective valences.

When any variable occurs more than one time in any substituent or in any formula, its definition in each occurrence is independent of its definition at every other occurrence. Thus, for example, if a group, or plurality of groups, is shown to be substituted with 0-2 $R^{80}$, then said group(s) may optionally be substituted with up to two $R^{80}$, and $R^{80}$ at each occurrence in each group is selected independently from the defined list of possible $R^{80}$. Also, by way of example, for the group —N($R^{81}$)$_2$, each of the two $R^{81}$ substituents on N is independently selected from the defined list of possible $R^{81}$. Combinations of substituents and/or variables are permissible only if such combinations result in stable compounds. When a bond to a substituent is shown to cross the bond connecting two atoms in a ring, then such substituent may be bonded to any atom on the ring.

Definitions

In certain instances the number of carbon atoms in a particular group is denoted before the recitation of the group. For example, the term "$C_6$-$C_{10}$aryl" denotes an aryl group containing from six to ten carbon atoms, and the term "$C_6$-$C_{10}$aryl-$C_1$-$C_{10}$alkyl," refers to an aryl group of six to ten carbon atoms attached to the parent molecular moiety through an alkyl group of one to ten carbon atoms.

The term "alkenyl," as used herein, refers to a straight or branched chain hydrocarbon containing at least one carbon-carbon double bond.

The term "alkoxy," as used herein, refers to a $C_1$-$C_6$ alkyl group attached to the parent molecular moiety through an oxygen atom.

The term "alkoxyalkyl," as used herein, refers to a $C_1$-$C_6$ alkyl group substituted with one, two, or three alkoxy groups.

The term "alkyl," as used herein, refers to a group derived from a straight or branched chain saturated hydrocarbon of one to twenty carbon atoms.

The term "alkylene," as used herein, refers to a divalent group derived from a straight or branched chain saturated hydrocarbon.

The term "analog moiety," as used herein, refers to the compounds of the present disclosure excluding the imaging moiety or moieties.

The term "aryl," as used herein, refers to a phenyl group, or a bicyclic fused ring system wherein one or more of the rings is a phenyl group. Bicyclic fused ring systems consist of a phenyl group fused to a monocyclic cycloalkenyl group, a monocyclic cycloalkyl group, or another phenyl group. The aryl groups of the present disclosure can be attached to the parent molecular moiety through any substitutable carbon atom in the group. Representative examples of aryl groups include, but are not limited to, anthracenyl, azulenyl, fluorenyl, indanyl, indenyl, naphthyl, phenyl, and tetrahydronaphthyl.

The term "arylalkyl," as used herein, refers to an alkyl group substituted with one, two, or three aryl groups.

The term "arylalkylene," as used herein, refers to a divalent arylalkyl group, where one point of attachment to the parent molecular moiety is on the aryl portion and the other is on the alkyl portion.

The term "arylene," as used herein, refers to a divalent aryl group.

As used herein, the terms "ancillary" or "co-ligands" refers to ligands that serve to complete the coordination sphere of the radionuclide together with the chelator or radionuclide bonding unit of the reagent. For radiopharmaceuticals comprising a binary ligand system, the radionuclide coordination sphere comprises one or more chelators or bonding units from one or more reagents and one or more ancillary or co-ligands, provided that there are a total of two types of ligands, chelators or bonding units. For example, a radiopharmaceutical comprised of one chelator or bonding unit from one reagent and two of the same ancillary or co-ligands and a radiopharmaceutical comprising two chelators or bonding units from one or two reagents and one ancillary or co-ligand are both considered to comprise binary ligand systems. For radiopharmaceuticals comprising a ternary ligand system, the radionuclide coordination sphere comprises one or more chelators or bonding units from one or more reagents and one or more of two different types of ancillary or co-ligands, provided that there are a total of three types of ligands, chelators or bonding units. For example, a radiopharmaceutical comprised of one chelator or bonding unit from one reagent and two different ancillary or co-ligands is considered to comprise a ternary ligand system.

Ancillary or co-ligands useful in the preparation of radiopharmaceuticals and in diagnostic kits useful for the preparation of said radiopharmaceuticals comprise one or more oxygen, nitrogen, carbon, sulfur, phosphorus, arsenic, selenium, and tellurium donor atoms. A ligand can be a transfer ligand in the synthesis of a radiopharmaceutical and also serve as an ancillary or co-ligand in another radiopharmaceutical. Whether a ligand is termed a transfer or ancillary or co-ligand depends on whether the ligand remains in the radionuclide coordination sphere in the radiopharmaceutical, which is determined by the coordination chemistry of the radionuclide and the chelator or bonding unit of the reagent or reagents.

A "bacteriostat" is a component that inhibits the growth of bacteria in a formulation either during its storage before use of after a diagnostic kit is used to synthesize a radiopharmaceutical.

The term "bubbles" or "microbubbles," as used herein, refers to vesicles which are generally characterized by the presence of one or more membranes or walls surrounding an internal void that is filled with a gas or precursor thereto. Exemplary bubbles or microbubbles include, for example, liposomes, micelles, and the like.

The terms "chelator" and "bonding unit," as used herein, refer to the moiety or group on a reagent that binds to a metal ion through one or more donor atoms.

The term "contrast agent," as used herein, refers to an agent used to highlight specific areas so that organs, blood vessels, and/or tissues are more visible. By increasing the visibility of the surfaces being studied, the presence and extent of disease and/or injury can be determined.

The term "cycloalkenyl," as used herein, refers to a non-aromatic, partially unsaturated monocyclic, bicyclic, or tricyclic ring system having three to fourteen carbon atoms and zero heteroatoms. Representative examples of cycloalkenyl groups include, but are not limited to, cyclohexenyl, octahydronaphthalenyl, and norbornylenyl.

The term "cycloalkyl," as used herein, refers to a saturated monocyclic, bicyclic, or tricyclic hydrocarbon ring system having three to fourteen carbon atoms and zero heteroatoms. Representative examples of cycloalkyl groups include, but are not limited to, cyclopropyl, cyclopentyl, bicyclo[3.1.1]heptyl, and adamantyl.

The term "$C_3$-$C_{10}$ cycloalkylene," as used herein, refers to a divalent cycloalkyl group containing from three to ten carbon atoms.

The term "diagnostic imaging," as used herein, refers to a procedure used to detect a contrast agent.

A "diagnostic kit" or "kit" comprises a collection of components, termed the formulation, in one or more vials which are used by the practicing end user in a clinical or pharmacy setting to synthesize diagnostic radiopharmaceuticals. The kit preferably provides all the requisite components to synthesize and use the diagnostic pharmaceutical except those that are commonly available to the practicing end user, such as water or saline for injection, a solution of the radionuclide, equipment for heating the kit during the synthesis of the radiopharmaceutical, if required, equipment necessary for administering the radiopharmaceutical to the patient such as syringes, shielding, imaging equipment, and the like. Contrast agents are provided to the end user in their final form in a formulation contained typically in one vial, as either a lyophilized solid or an aqueous solution. The end user typically reconstitutes the lyophilized material with water or saline and withdraws the patient dose or just withdraws the dose from the aqueous solution formulation as provided.

The term "donor atom," as used herein, refers to the atom directly attached to a metal by a chemical bond.

The term "halo," as used herein, refer to F, Cl, Br, or I.

The term "heterocyclyl," as used herein, refers to a five-, six-, or seven-membered ring containing one, two, or three heteroatoms independently selected from the group consisting of nitrogen, oxygen, and sulfur. The five-membered ring has zero to two double bonds and the six- and seven-membered rings have zero to three double bonds. The term "heterocyclyl" also includes bicyclic groups in which the heterocyclyl ring is fused to a phenyl group, a monocyclic cycloalkenyl group, a monocyclic cycloalkyl group, or another monocyclic heterocyclyl group. The heterocyclyl groups of the present disclosure can be attached to the parent molecular moiety through a carbon atom or a nitrogen atom in the group. Examples of heterocyclyl groups include, but are not limited to, benzothienyl, furyl, imidazolyl, indolinyl, indolyl, isothiazolyl, isoxazolyl, morpholinyl, oxazolyl, piperazinyl, piperidinyl, pyrazolyl, pyridinyl, pyrrolidinyl, pyrrolopyridinyl, pyrrolyl, thiazolyl, thienyl, and thiomorpholinyl.

The term "heterocyclylalkyl," as used herein, refers to an alkyl group substituted with one, two, or three heterocyclyl groups.

The term "heterocyclylalkylene," as used herein, refers to a divalent heterocyclylalkyl group, where one point of attachment to the parent molecular moiety is on the heterocyclyl portion and the other is on the alkyl portion.

The term "heterocyclylene," as used herein, refers to a divalent heterocyclyl group.

The term "hydroxy," as used herein, refers to —OH.

The term "imaging moiety," as used herein, refer to a portion or portions of a molecule that allow for the detection, imaging, and/or monitoring of the presence and/or progression of a condition(s), pathological disorder(s), and/or disease(s).

The term "linking group," as used herein, refers to a portion of a molecule that serves as a spacer between two other portions of the molecule. Linking groups may also serve other functions as described herein. Examples of linking groups include linear, branched, or cyclic alkyl, aryl, ether, polyhydroxy, polyether, polyamine, heterocyclic, aromatic, hydrazide, peptide, peptoid, or other physiologically compatible covalent linkages or combinations thereof.

As used herein, the term "lipid" refers to a synthetic or naturally-occurring amphipathic compound which comprises a hydrophilic component and a hydrophobic component. Lipids include, for example, fatty acids, neutral fats, phosphatides, glycolipids, aliphatic alcohols and waxes, terpenes and steroids. Exemplary compositions which comprise a lipid compound include suspensions, emulsions and vesicular compositions.

"Liposome" refers to a generally spherical cluster or aggregate of amphipathic compounds, including lipid compounds, typically in the form of one or more concentric layers, for example, bilayers. They may also be referred to herein as lipid vesicles.

A "lyophilization aid" is a component that has favorable physical properties for lyophilization, such as the glass transition temperature, and is generally added to the formulation to improve the physical properties of the combination of all the components of the formulation for lyophilization.

The term "open chain deguelin analog," as used herein, refers to an analog of deguelin (shown below) wherein at least one of rings C and D is not present, i.e., is replaced by a linker connecting the remaining rings.

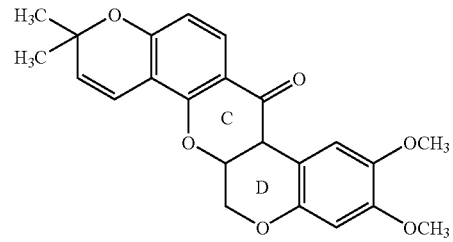

deguelin

As used herein, the phrase "pharmaceutically acceptable" refers to those compounds, materials, compositions, and/or dosage forms that are, within the scope of sound medical judgment, suitable for use in contact with the tissues of human beings and animals without excessive toxicity, irritation, allergic response, or other problem or complication, commensurate with a reasonable benefit/risk ratio.

The compounds of the present disclosure can exist as pharmaceutically acceptable salts. The term "pharmaceutically acceptable salt," as used herein, represents salts or zwitterionic forms of the compounds of the present disclosure which are water or oil-soluble or dispersible, which are, within the scope of sound medical judgment, suitable for use in contact with the tissues of patients without excessive toxicity, irritation, allergic response, or other problem or complication commensurate with a reasonable benefit/risk ratio, and are effective for their intended use The salts can be prepared during the final isolation and purification of the compounds or separately by reacting a suitable nitrogen atom with a suitable acid. Representative acid addition salts include acetate, adipate, alginate, citrate, aspartate, benzoate, benzenesulfonate, bisulfate, butyrate, camphorate, camphorsulfonate; digluconate, glycerophosphate, hemisulfate, heptanoate, hexanoate, formate, fumarate, hydrochloride, hydrobromide, hydroiodide, 2-hydroxyethanesulfonate, lactate, maleate, mesitylenesulfonate, methanesulfonate, naphthylenesulfonate, nicotinate, 2-naphthalenesulfonate, oxalate, palmoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Examples of acids which can be employed to form pharmaceutically acceptable addition salts include inorganic acids such as hydrochloric, hydrobromic, sulfuric, and phosphoric, and organic acids such as oxalic, maleic, succinic, and citric.

By "reagent" is meant a compound of this disclosure capable of direct transformation into a metallopharmaceutical of this disclosure. Reagents may be utilized directly for the preparation of the metallopharmaceuticals of this disclosure or may be a component in a kit of this disclosure.

A "reducing agent" is a compound that reacts with a radionuclide, which is typically obtained as a relatively unreactive, high oxidation state compound, to lower its oxidation state by transferring electron(s) to the radionuclide, thereby making it more reactive. Reducing agents useful in the preparation of radiopharmaceuticals and in diagnostic kits useful for the preparation of said radiopharmaceuticals include, for example, stannous chloride, stannous fluoride, formamidine sulfinic acid, ascorbic acid, cysteine, phosphines, and cuprous or ferrous salts. Other reducing agents are described, for example, in Brodack et. al., PCT Application 94/22496.

A "stabilization aid" is a component that is typically added to the metallopharmaceutical or to the diagnostic kit either to stabilize the metallopharmaceutical or to prolong the shelf-life of the kit before it must be used. Stabilization aids can be antioxidants, reducing agents or radical scavengers and can provide improved stability by reacting preferentially with species that degrade other components or the metallopharmaceuticals.

By "stable compound" is meant herein a compound that is sufficiently robust to survive isolation to a useful degree of purity from a reaction mixture, and formulation into an efficacious pharmaceutical agent.

A "solubilization aid" is a component that improves the solubility of one or more other components in the medium required for the formulation.

The term "thiol protecting group," as used herein, refers to a group intended to protect a thiol group against undesirable reactions during synthetic procedures. Any thiol protecting group known in the art may be used. Examples of thiol protecting groups include, but are not limited to, the following: acetamidomethyl, benzamidomethyl, 1-ethoxyethyl, benzoyl, and triphenylmethyl.

A "transfer ligand" is a ligand that forms an intermediate complex with a metal ion that is stable enough to prevent unwanted side-reactions but labile enough to be converted to a contrast agent. The formation of the intermediate complex is kinetically favored while the formation of the metallopharmaceutical is thermodynamically favored. Transfer ligands useful in the preparation of contrast agents and in diagnostic kits useful for the preparation of diagnostic radiopharmaceuticals include, for example, gluconate, glucoheptonate, mannitol, glucarate, N,N,N',N'-ethylenediaminetetraacetic acid, pyrophosphate and methylenediphosphonate. In general, transfer ligands are comprised of oxygen or nitrogen donor atoms.

As used herein, the term "vesicle" refers to a spherical entity which is characterized by the presence of an internal void. In one embodiment vesicles are formulated from lipids, including the various lipids described herein. In any given vesicle, the lipids may be in the form of a monolayer or bilayer, and the mono- or bilayer lipids may be used to form one of more mono- or bilayers. In the case of more than one mono- or bilayer, the mono- or bilayers are generally concentric. The lipid vesicles described herein include such entities commonly referred to as liposomes, micelles, bubbles, microbubbles, microspheres and the like. Thus, the lipids may be used to form a unilamellar vesicle (comprised of one monolayer or bilayer), an oligolamellar vesicle (comprised of about two or about three monolayers or bilayers) or a multilamellar vesicle (comprised of more than about three monolayers or bilayers). The internal void of the vesicles may be filled with a liquid, including, for example, an aqueous liquid, a gas, a gaseous precursor, and/or a solid or solute material, including, for example, a bioactive agent, as desired.

As used herein, the term "vesicular composition" refers to a composition which is formulate from lipids and which comprises vesicles.

The present disclosure will now be described in connection with certain embodiments which are not intended to limit its scope. On the contrary, the present disclosure covers all alternatives, modifications, and equivalents as can be included within the scope of the claims. Thus, the following examples will illustrate one practice of the present disclosure, it being understood that the examples are for the purposes of illustration of certain embodiments and are presented to provide what is believed to be the most useful and readily understood description of its procedures and conceptual aspects.

EXAMPLE 1

1a. {2R-[2α[2'R*, 5'R*(R*)], 5β[1(S*), 2R*, 11R*]}-3-{2-[(1,1-dimethylethyl)diphenylsilyloxy]-11-methoxymethyloxy-11-[octahydro-5'-(1-(methoxymethyloxy)undec-3-ynyl) [2.2'-bifuran]-5-yl]-6-undecen-8-ynyl}-5-methyl-2-(5H)-furanone

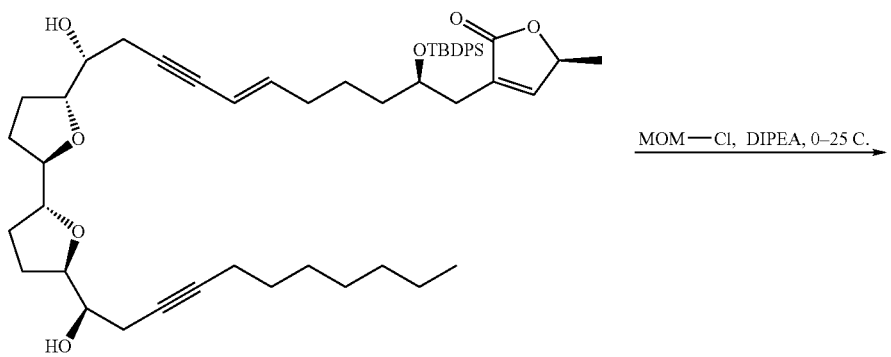

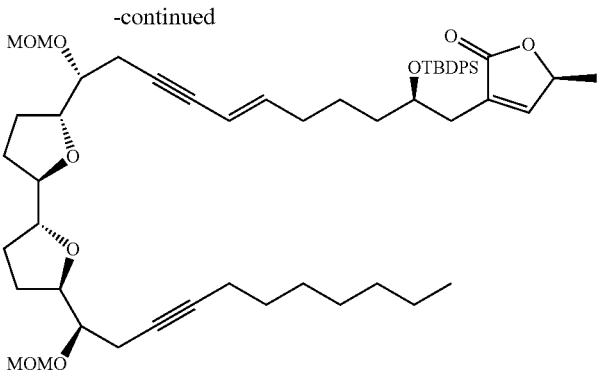

A solution of {2R-[2α[2'R*, 5'R*(R*)],5β[1(S*), 2R*, 11R*]}-3-{2-[(1,1-dimethylethyl)diphenylsilyloxy]-11-hydroxy-11-[octahydro-5'-(1-hydroxyundec-3-ynyl)[2.2'-bifuran]-5-yl]-6-undecen-8-ynyl}-5-methyl-2-(5H)-furanone (82.3 mg, 0.1 mmol, which can be prepared via the route described in Hoye and Ye, U.S. Pat. No. 5,677,4671 and J. Am. Chem. Soc. 1996, 118, 1801-1802) in diisopropylethylamine (2 mL) is stirred at room temperature while methoxymethyl chloride (24 mg, 23 μL) is added. The mixture is stirred at room temperature for four hours, and concentrated in vacuo. The residue is partitioned between water (2 mL) and ether (2 mL). The aqueous phase is separated and extracted with ether (2 mL) and the combined organic fractions are washed (1×5% CuSO₄, 1× water) dried (saturated aqueous NaCl, sodium sulfate), filtered, and concentrated. Chromatography (hexane-2:1 hexane:ethyl acetate gradient over silica gel 230-400 mesh) provides the desired product.

1b. {2R-[2α[2'R*, 5'R*(R*)],5β[1(S*), 2R*, 11R*]}-3-{2-hydroxy-11-methoxymethyloxy-11-[octahydro-5'-(1-(methoxymethyloxy)undecyl)[2.2'-bifuran]-5-yl]undecyl}-5-methyl-2-(5H)-furanone

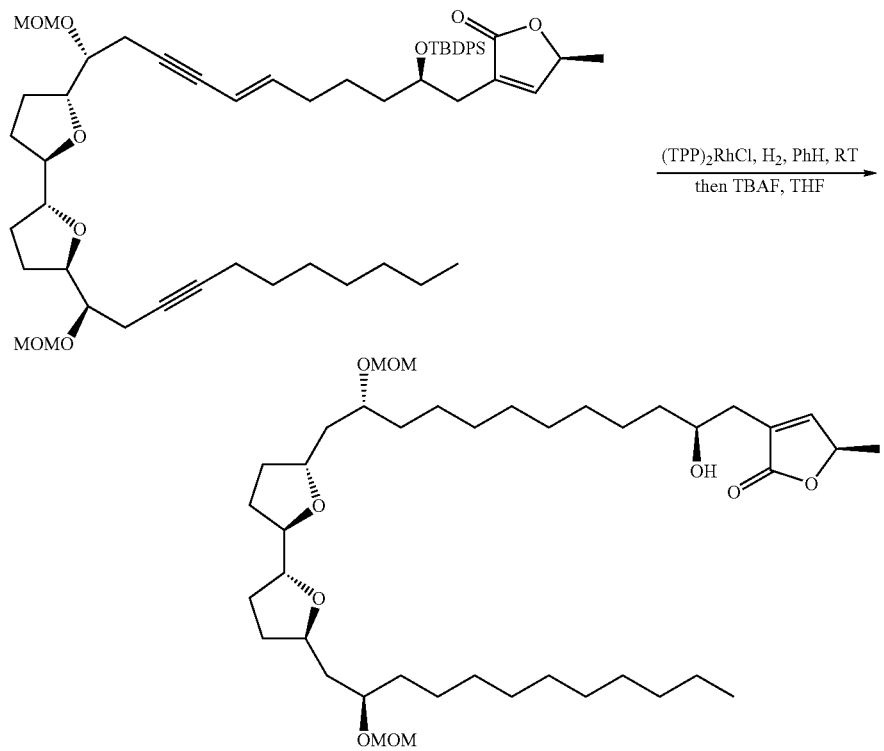

A solution of {2R-[2α[2'R*, 5'R*(R*)],5β[1(S*), 2R*, 11R*]}-3-{2-[(1,1-dimethylethyl)diphenylsilyloxy]-11-methoxymethyloxy-11-[octahydro-5'-(1-(methoxymethyloxy)undec-3-ynyl) [2.2'-bifuran]-5-yl]-6-undecen-8-ynyl}-5-methyl-2-(5H)-furanone (64 mg, 70 mmole) in benzene (0.5 mL) is stirred at room temperature under a flow of nitrogen while tris(triphenylphosphine)rhodium chloride (14 mg, 15 mmole) is added. The mixture is charged with hydrogen gas and stirred at room temperature for two days. Water is added, and the layers are separated. The aqueous extracted with ethyl acetate (3×2 mL) and the combined organic fractions are washed (1×20 mL water) dried (saturated aqueous NaCl, sodium sulfate), filtered, and concentrated. Chromatography (hexane-2:1 hexane:ethyl acetate gradient over silica gel 230-400 mesh) affords the desired product.

The material is dissolved in THF (2 mL) and a solution of tetra-n-butylammonium fluoride (100 uL of a 1.0M solution in THF) is added. The mixture is stirred at room temperature for 30 minutes, and concentrated in vacuo. The residue is partitioned between water (2 mL) and ethyl acetate (2 mL). The aqueous phase is separated and extracted with ethyl acetate (2×2 mL) and the combined organic fractions are washed (1× water), dried (saturated aqueous NaCl, sodium sulfate), filtered, and concentrated. Chromatography (hexane-2:1 hexane:ethyl acetate gradient over silica gel 230-400 mesh) affords the desired product.

1c. {2R-[2α[2'R*, 5'R*(R*)],5β[1(S*), 2R*, 11R*]-3-2-[p-toluenesulfonato]-11-methoxymethyloxy-11-[octahydro-5'-(1-(methoxymethyloxy)undecyl) [2.2'-bifuran]-5-yl]undecyl}-5-methyl-2-(5H)-furanone A solution of {2R-[2α[2'R*, 5'R*(R*)],5β[1(S*), 2R*, 11R*]}-3-{2-hydroxy-11-methoxymethyloxy-11-[octahydro-5'-(1-(methoxymethyloxy)undecyl) [2.2'-bifuran]-5-yl] undecyl}-5-methyl-2-(5H)-furanone (34 mg, 50 mmole) in pyridine (2 mL) is stirred at room temperature while p-toluenesulfonyl chloride (20 mg, 60 mmole) is added. The mixture is stirred at room temperature for fifteen hours, and concentrated in vacuo. The residue is partitioned between water (2 mL) and ethyl acetate (2 mL). The aqueous phase is separated and extracted with ethyl acetate (3×2 mL) and the combined organic fractions are washed (1×5% CuSO$_4$, 1× water) dried (saturated aqueous NaCl, sodium sulfate), filtered, and concentrated. Chromatography (hexane-2:1 hexane:ethyl acetate gradient over silica gel 230-400 mesh) affords the desired product.

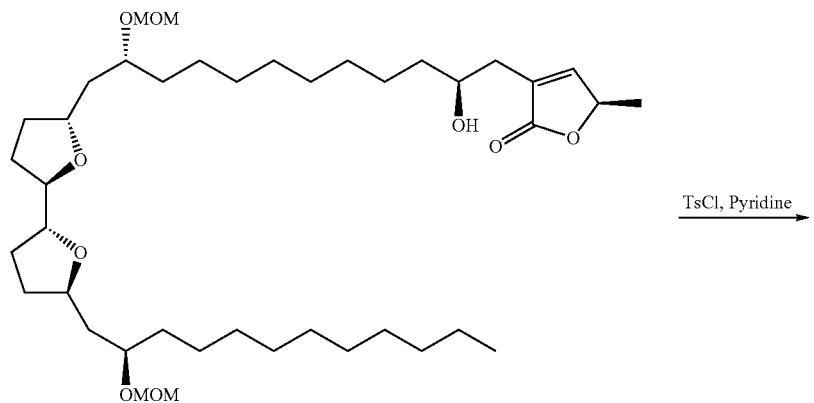

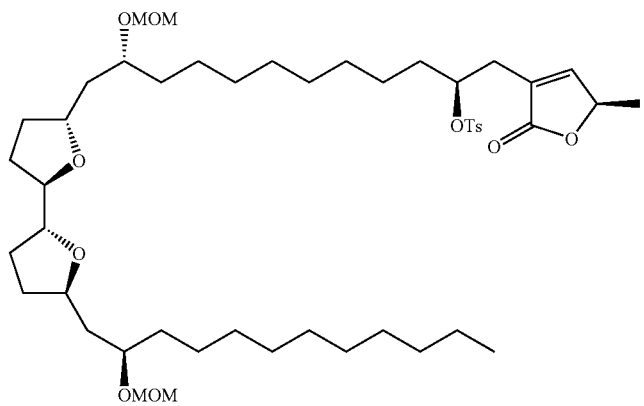

1d. {2S-[2α[2'R*, 5'R*(R*)],5β[1(S*), 2R*, 11R*]}-3-{2-[18F]fluoro-11-hydroxy-11-[octahydro-5'-(1-hydroxyundecyl) [2.2'-bifuran]-5-yl]undecyl}-5-methyl-2-(5H)-furanone

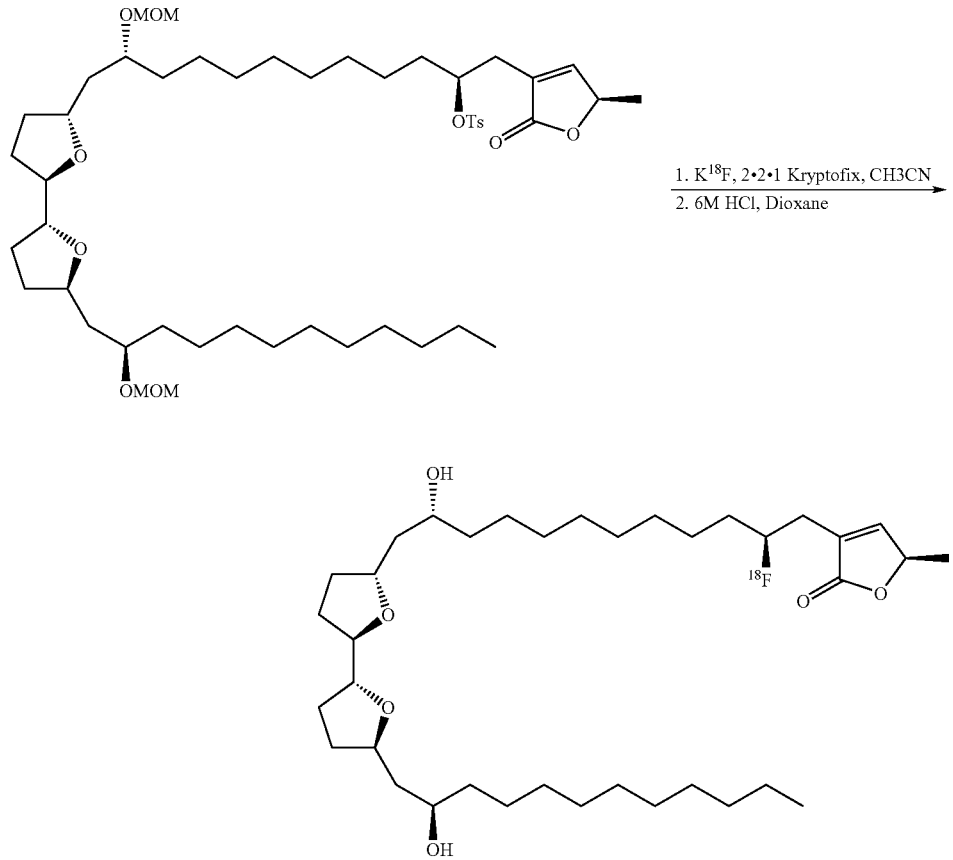

A thin-wall 10 mL, silanized vacutainer with a silanized stopper is charged with tetrabutyl ammonium hydroxide (5 uL, 40% w/v solution in water), and a solution of 18F— in water (10 mCi, 200 uL). The resultant mixture is evaporated to dryness under a flow of nitrogen at 100° C. The residue is dried further by repeated cycles of addition and evaporation of acetonitrile (3×200 μL). An additional aliquot of acetonitrile is added and the mixture is concentrated under vacuum without heating. Prior to complete solvent removal, a solution of {2R-[2α[2R*, 5'R*(R*)],5β[1(S*), 2R*,6E,11R*]}-3-{2-[p-toluene sulfonato]-11-methoxymethyloxy-11-[octahydro-5'-(1-(methoxymethyloxy) undecyl) [2.2'-bifuran]-5-yl] undecyl}-5-methyl-2-(5H)-furanone (2 mg) in THF (150 μL) is added rapidly. The vial is heated at 65° C. for 30 minutes. After cooling, a solution of HCl in THF (30 μL, 6M) is added, the vial is heated again to 65° C. for 15 minutes, then cooled. The contents of the vial are diluted with water (4 mL) and passed through a silica gel cartridge (pre-loaded Waters Light C-18 Sep-Pak) to load the sample. The cartridge is rinsed with water and eluted with acetonitrile (2 mL). The acetonitrile is evaporated and the residue is purified via HPLC to afford the desired product.

EXAMPLE 2

2a. 5-formyl-octahydro-5'-(1-methoxymethoxyundecyl) [2.2'-bifuran]

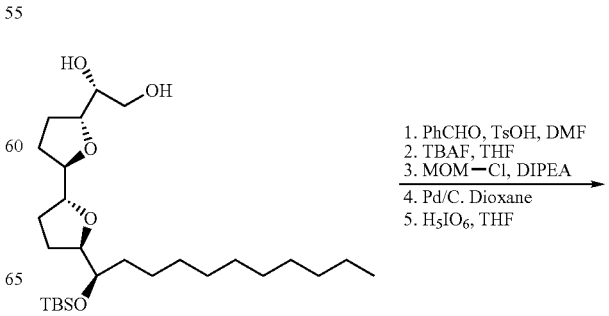

1. PhCHO, TsOH, DMF
2. TBAF, THF
3. MOM—Cl, DIPEA
4. Pd/C. Dioxane
5. H5IO6, THF

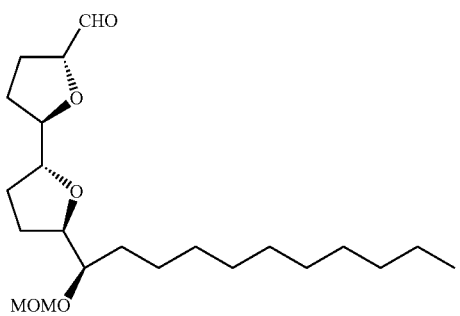

A solution of decyloctahydro-α'-(hydroxymethyl)-2,2'-bifuran-5,5'-dimethanol-α-{[(1,1-dimethylethyl)dimethyl]silylether} (4.87 g, 10 mmol, which can be prepared via the route shown in U.S. Pat. No. 5,587,491, Example 15) is treated with benzaldehyde dimethylacetal (2.27 g, 15 mmol) in DMF (25 mL) and toluenesulfonic acid (30 mg). The mixture is stirred at room temperature for 24 hours, and concentrated in vacuo. The residue is partitioned between water (50 mL) and ethyl acetate (50 mL). The aqueous phase is separated and extracted with ethyl acetate (2×50 mL) and the combined organic fractions are washed (1×saturated aqueous NaHCO$_3$, 1× water), dried (saturated aqueous NaCl, sodium sulfate), filtered, and concentrated.

The residual oil is dissolved in THF (20 mL) and tetrabutylammonium fluoride (1.0M in THF, 10.5 mL, 1.05 eq.) is added, and the mixture stirred at room temperature for two hours. The solvent is removed in vacuo, and the residue is partitioned between water (50 mL) and ethyl acetate (50 mL). The aqueous phase is separated and extracted with ethyl acetate (2×50 mL) and the combined organic fractions are washed (1× water), dried (saturated aqueous NaCl, sodium sulfate), filtered, and concentrated.

The residual oil is dissolved in diisopropylethylamine (15 mL), and chloromethyl methyl ether (880 mg, 11 mmol) is added. The mixture is stirred for eight hours at room temperature, and the solvent is removed in vacuo. The residue is partitioned between water (40 mL) and ethyl acetate (40 mL). The aqueous phase is separated and extracted with ethyl acetate (2×40 mL) and the combined organic fractions are washed (1× water), dried (saturated aqueous NaCl, sodium sulfate), filtered, and concentrated. Chromatography (hexane-2:1 hexane:ethyl acetate gradient over silica gel 230-400 mesh) affords the acetal as an oil.

The oil is dissolved in dioxane (20 mL) and transferred to a hydrogenation bomb. Palladium on carbon (5%, 100 mg) is added, and the apparatus is pressurized with hydrogen (2 atm) for 45 minutes. The gas is vented, and the mixture is filtered through diatomaceous earth (Celite®) with the aid of additional dioxane. The filtrate is concentrated in vacuo, and chromatographed (hexane-2:1 hexane:ethyl acetate gradient over silica gel 230-400 mesh) to afford the diol as an oil.

A portion of this oil (416 mg, 1.0 mmol) is dissolved in THF (5 mL) and a saturated solution of ethereal H$_5$IO$_6$ (16 mL, which can prepared according to the procedure described in *J. Org. Chem.* 1963, 28, 23) is added. The precipitated iodic acid is filtered, and the resultant solution is concentrated in vacuo, and chromatographed (hexane-2:1 hexane:ethyl acetate gradient over silica gel 230-400 mesh) to afford the aldehyde as an oil.

2b. 5-(,1,1-dimethylethyl)dimethylsilyloxynona-1,8-diyne

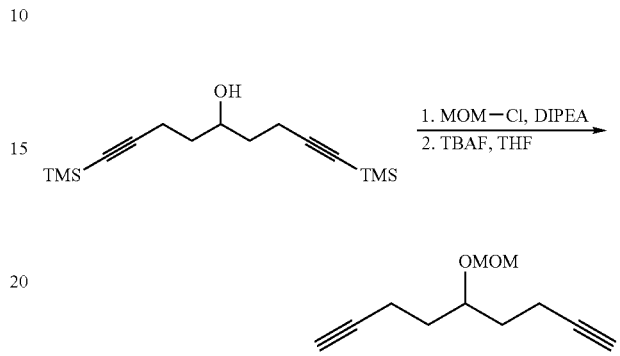

A solution of 1,9-bis-triemtylsilylnona-1,8-diyn-5-ol (2.80 g, 10 mmol, prepared via the method of Clive, D. L. J.; Cole, D.C. JCS, Perkin 1 1991, 12, 3263-70) in diisopropylethylamine (10 mL) is stirred at room temperature while chloromethyl methyl ether (880 mg, 11 mmol) is added. The mixture is stirred for four hours, and is then concentrated in vacuo. The residue is partitioned between ether (100 mL) and water (100 mL). The aqueous phase is separated and extracted with ether (2×100 mL) and the combined organics are washed (2×100 mL 0.5M NaHSO$_4$), dried (saturated aqueous NaCl, sodium sulfate), filtered, and concentrated.

The oil is dissolved in THF (10 mL) and TBAF (1.0M soln. in THF, 21 mL) is added. The mixture is stirred at room temperature for one hour, and poured into water (100 mL). The aqueous phase is separated and extracted with ether (2×100 mL), and the combined organics are concentrated in vacuo, and chromatographed (hexane-2:1 hexane:ethyl acetate gradient over silica gel 230-400 mesh) to afford the diyne as an oil.

2c. 5-(1,1-dimethylethyl)dimethylsilyloxy-10-methoxymethoxy-10-[octahydro-5'-(1-(methoxymethyloxy)undecyl) [2.2'-bifuran]-5-yl]deca-1,8-diyne

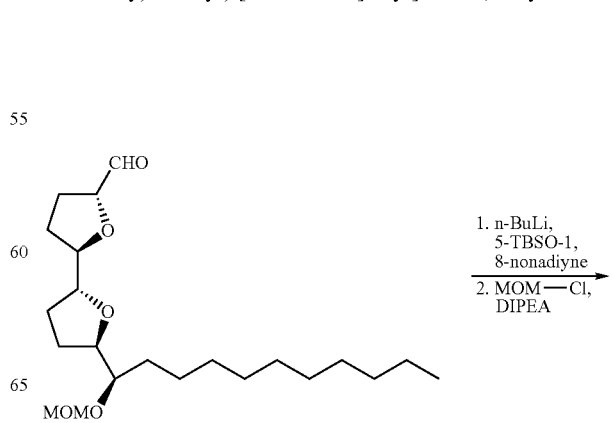

-continued

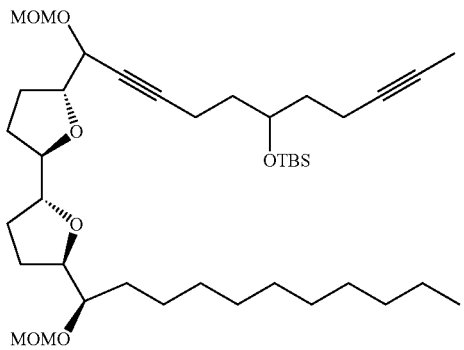

A solution of 5-(1,1-dimethylethyl)dimethylsilyloxynona-1,8-diyne (1.80 g, 10 mmol) in THF (10 mL) is stirred at −78° C. while a solution of n-butyllithium (2.0M in hexanes, 4.95 mL) is added. The mixture is stirred for ten minutes at −78 degrees C. and boron trifluoride etherate (9.9 mmol, 1.25 mL) is added. After another thirty minutes stirring at −78° C., a solution of 5-formyl-octahydro-5'-(1-methoxymethoxy undecyl)-[2.2']-bifuran (1.35 g, 3.5 mmol) in THF (8 mL) is added. The resulting solution is stirred at −78° C. for four hours, and is poured into an aqueous solution of NH$_4$Cl (100 mL, 2.0 M). The mixture is extracted with ethyl acetate (3×100 mL) and the combined organic fractions are washed (1× water), filtered, (saturated aqueous NaCl, sodium sulfate) and concentrated. Chromatography (hexane-2:1 hexane:ethyl acetate gradient over silica gel 230-400 mesh) affords 5-(1,1-dimethylethyl)dimethylsilyloxy-10-methoxymethoxy-10-[octahydro-5'-(1-hydroxyundecyl) [2.2'-bifuran]-5-yl]deca-1,8-diyne as an oil.

A solution of this oil (1.27 g, 2 mmol) in diisopropylethylamine (6 mL) is treated with chloromethyl methyl ether (201 mg, 2.5 mmol) at room temperature. After two hours of stirring, the mixture is concentrated in vacuo, and the residue is partitioned between water (50 mL) and ethyl acetate (50 mL). The aqueous phase is separated and extracted with ethyl acetate (2×50 mL) and the combined organic fractions are washed (1× water), dried (saturated aqueous NaCl, sodium sulfate), filtered, and concentrated. Chromatography (hexane-2:1 hexane:ethyl acetate gradient over silica gel 230-400 mesh) affords 5-(1,1-dimethylethyl)dimethylsilyloxy-10-methoxymethyloxy-10-[octahydro-5'-(1-(methoxymethyloxy)undecyl)[2.2'-bifuran]-5-yl]deca-1,8-diyne as an oil.

2d. 3-{2,13-bis(methoxymethyloxy)-8-[(1,1-dimethylethyl)dimethylsilyl oxy]-13-[octahydro-5'-(1-(methoxymethyloxy)undecyl) [2.2'-bifuran]-5-yl] trideca-4,11-diynyl}-5-methyl-2-(5H)-furanone

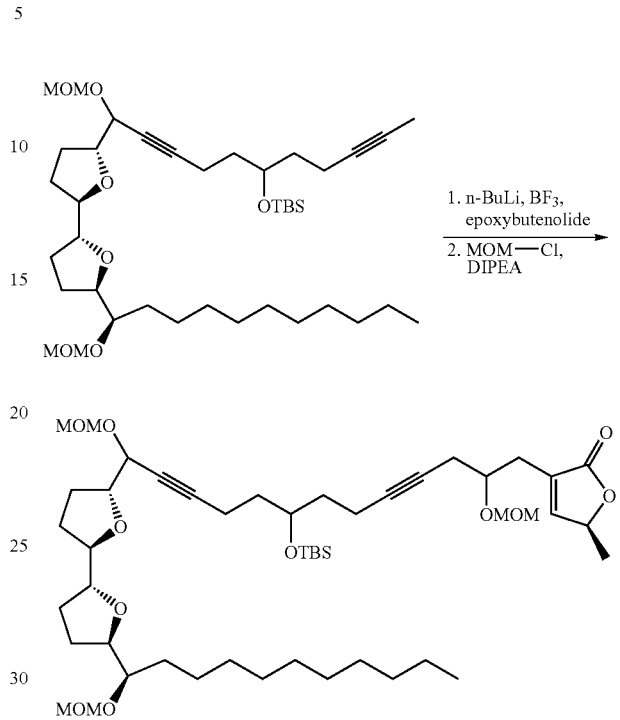

A solution of 5-(1,1-dimethylethyl)dimethylsilyloxy-10-methoxymethyloxy-10-[octahydro-5'-(1-(methoxymethyloxy)undecyl) [2.2'-bifuran]-5-yl]deca-1,8-diyne (1.035 g, 1.5 mmol) in THF (6 mL) is cooled at −78° C. while n-butyllithium in hexanes (2.0M, 0.75 mL) is added. After stirring for 30 minutes, boron trifluoride etherate (190 uL, 1.5 mmol) is added, and after an additional fifteen minutes, a solution of (5S)-methyl-3-[(2S)-oxiranylmethyl]-5H-faran-2-one (154 mg, 1.0 mmol) in THF (2 mL) is added. The reaction mixture is stirred at −78° C. for three hours, and is poured into an aqueous solution of NH4Cl (100 mL, 2.0 M). The mixture is extracted with ethyl acetate (3×100 mL) and the combined organic fractions are washed (1× water), dried (saturated aqueous NaCl, sodium sulfate), filtered, and concentrated. Chromatography (hexane-2:1 hexane:ethyl acetate gradient over silica gel 230-400 mesh) affords 3-{2-hydroxy-13-methoxymethyloxy-8-[(1,1-dimethylethyl)dimethylsilyl oxy]-13-[octahydro-5'-(1-(methoxymethyloxy)undecyl) [2.2'-bifuran]-5-yl]trideca-4,11-diynyl}-5-methyl-2-(5H)-furanone as an oil.

This oil is dissolved in diisopropylethylamine (3 mL) and chloromethyl methyl ether (120 mg, 1.5 mmol) is added. The mixture is stirred at room temperature for eight hours, concentrated in vacuo, and the residue is partitioned between water (50 mL) and ethyl acetate (50 mL). The aqueous phase is separated and extracted with ethyl acetate (2×50 mL) and the combined organic fractions are washed (1× water), dried (saturated aqueous NaCl, sodium sulfate), filtered, and concentrated. Chromatography (hexane-2:1 hexane:ethyl acetate gradient over silica gel 230-400 mesh) affords the desired product as an oil.

2e. 3-{2,13-bis(methoxymethyloxy)-8-(p-toluene-sulfonato)-13-[octahydro-5'-(1-(methoxymethyloxy) undecyl) [2.2'-bifuran]-5-yl]tridecyl}-5-methyl-2-(5H)-furanone

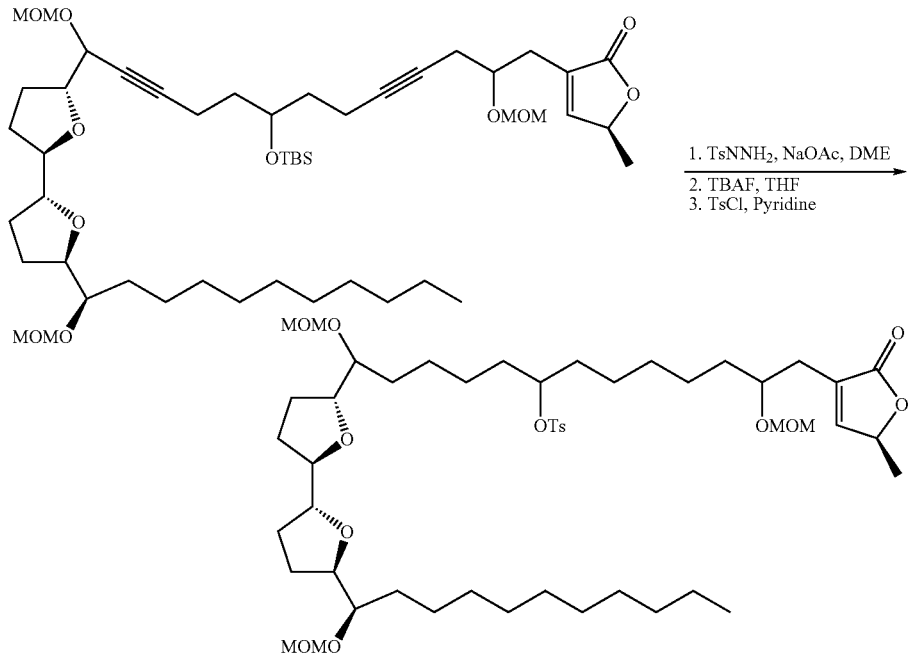

A solution of 3-{2,13-bis(methoxymethyloxy)-8-[(1,1-dimethylethyl)dimethylsilyl oxy]-13-[octahydro-5'-(1-(methoxymethyloxy)undecyl) [2.2'-bifuran]-5-yl]trideca-4,11-diynyl}-5-methyl-2-(5H)-furanone (87.8 mg, 0.10 mmol) and p-toluenesulfonhydrazide (1.86 g, 10 mmol) in dimethoxyethane (15 mL) is heated at reflux while a solution of NaOAc (984 mg 12 mmol) in water (10 mL) is added over three hours. The mixture is cooled to room temperature and poured into water (100 mL), and extracted with dichloromethane (2×30 mL). The combined organic layers are dried (sodium sulfate), filtered, and concentrated.

The residue is dissolved in THF (5 mL) and TBAF (1.0M in THF, 120uL) is added. The mixture is stirred at room temperature for 30 minutes and concentrated. The residue is partitioned between water (50 mL) and ethyl acetate (50 mL). The aqueous phase is separated and extracted with ethyl acetate (2×50 mL) and the combined organic fractions are washed (1× water), dried (saturated aqueous NaCl, sodium sulfate), filtered, and concentrated.

The oil is dissolved in pyridine (1.0 mL) and p-toluenesulfonyl chloride (28.5 mg, 0.15 mmol) is added. The mixture is stirred at room temperature for two hours, and concentrated in vacuo. The residue is partitioned between dichloromethane (5 mL) and water (5 mL). The aqueous phase is separated and extracted with dichloromethane (2×5 mL) and the combined organic fractions are washed (1× water), dried (saturated aqueous NaCl, sodium sulfate), filtered, and concentrated. Chromatography (hexane-2:1 hexane:ethyl acetate gradient over silica gel 230-400 mesh) affords the desired product as an oil.

2f. 3-{2,13-bis(methoxymethyloxy)-8-[18F]fluoro-13-[octahydro-5'-(1-(methoxymethyloxy)undecyl) [2.2'-bifuran]-5-yl]tridecyl}-5-methyl-2-(5H)-furanone

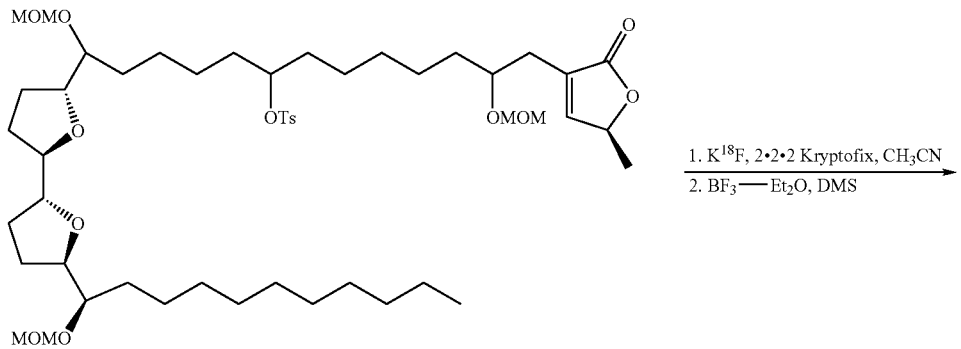

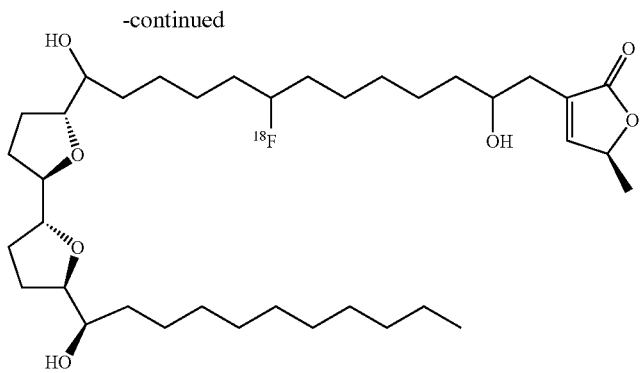

A thin-wall 10 mL, silanized vacutainer with a silanized stopper is charged with tetrabutyl ammonium hydroxide (5 uL, 40% w/v solution in water), and a solution of 18F— in water (10 mCi, 200 uL). The resultant mixture is evaporated to dryness under a flow of nitrogen at 100° C. The residue is dried further by repeated cycles of addition and evaporation of acetonitrile (3×200 uL). An additional aliquot of acetonitrile is added and concentrated under vacuum without heating. Prior to complete solvent removal, a solution of 3-{2,13-bis(methoxymethyloxy)-8-(p-toluenesulfonato)-13-[octahydro-5'-(1-(methoxymethyloxy)undecyl) [2.2'-bifuran]-5-yl]tridecyl}-5-methyl-2-(5H)-furanone (1 mg) in THF (150 uL) is added rapidly. The vial is heated at 65° C. for 15 minutes. After cooling, dimethylsulfide (100 uL) is added, followed by boron trifluoride etherate (200 uL). The vial is heated again to 65° C. for 15 minutes, then cooled. The contents of the vial are diluted with water (4 mL) and passed through a silica gel cartridge (pre-loaded Waters Light C-18 Sep-Pak) to load the sample. The cartridge is rinsed with water and eluted with acetonitrile (2 mL). The acetonitrile is evaporated and the residue is purified via HPLC to afford the desired product.

EXAMPLE 3

3a. 3-{8-(p-toluenesulfonato)-2,13-bis(methoxymethyloxy)-13-[tetrahydro-5-(1-methoxymethyloxytridecyl) furan-2-yl]tridecyl}-5-methyl-2-(5H)-furanone

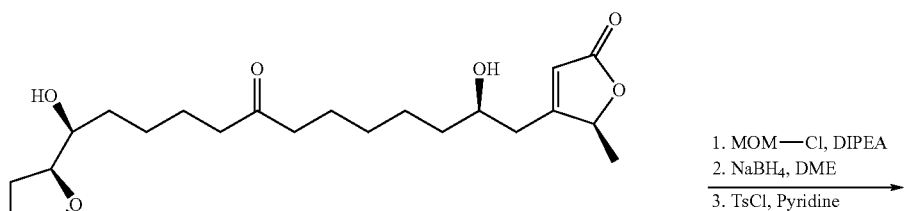

Annonacinone

1. MOM—Cl, DIPEA
2. NaBH$_4$, DME
3. TsCl, Pyridine

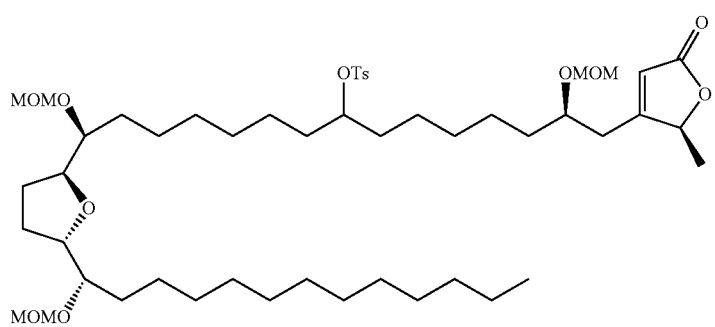

A solution of annonacinone (595 mg, 1.0 mmol) in diisopropylethylamine (7 mL) is stirred at room temperature while chloromethyl methyl ether (360 mg, 4.5 mmol) is added. The mixture is stirred at room temperature for eight hours, concentrated in vacuo, and the residue is partitioned between water (50 mL) and ethyl acetate (50 mL). The aqueous phase is separated and extracted with ethyl acetate (2×50 mL) and the combined organic fractions are washed (1× water), dried (saturated aqueous NaCl, sodium sulfate), filtered, and concentrated. Chromatography (hexane-2:1 hexane:ethyl acetate gradient over silica gel 230-400 mesh) affords 3-{2,13-bis(methoxymethyloxy)-13-[tetrahydro-5-(1-methoxymethyloxytridecyl) furan-2-yl]tridecan-8-on-1-yl}-5-methyl-2-(5H)-furanone.

The above prepared protected ketone is dissolved in ethanol (3 mL) with the aid of THF (100 uL). Solid sodium borohydride (76 mg, 2.0 mmol) is added in one portion and the mixture is stirred for thirty minutes at room temperature. The reaction mixture is diluted with water (20 mL) and extracted with ethyl acetate (3×50 mL). The combined organic fractions are washed (1× water), dried (saturated aqueous NaCl, sodium sulfate), filtered, and concentrated. Chromatography (hexane-2:1 hexane:ethyl acetate gradient over silica gel 230-400 mesh) affords the protected alcohol.

A portion of the alcohol (365 mg, 0.5 mmol) is dissolved in pyridine (5 mL) and p-toluenesulfonyl chloride (143 mg, 0.75 mmol) is added. The mixture is stirred at room temperature for two hours, and concentrated in vacuo. The residue is partitioned between dichloromethane (5 mL) and water (5 mL). The aqueous phase is separated and extracted with dichloromethane (2×5 mL) and the combined organic fractions are washed (1× water), dried (saturated aqueous NaCl, sodium sulfate), filtered, and concentrated. Chromatography (hexane-2:1 hexane:ethyl acetate gradient over silica gel 230-400 mesh) affords the desired product.

3b. 3-{8-[18F]fluoro-2,13-dihydroxy-13-[tetrahydro-5-(1-hydroxytridecyl) furan-2-yl]tridecyl}-5-methyl-2-(5H)-furanone A thin-wall 10 mL, silanized vacutainer with a silanized stopper is charged with tetrabutyl ammonium hydroxide (5 uL, 40% w/v solution in water), and a solution of 18F— in water (10 mCi, 200 uL). The resultant mixture is evaporated to dryness under a flow of nitrogen at 100° C. The residue is dried further by repeated cycles of addition and evaporation of acetonitrile (3×200 uL). An additional aliquot of acetonitrile is added and concentrated under vacuum without heating. Prior to complete solvent removal, a solution of affords 3-{8-(p-toluenesulfonato)-2,13-bis(methoxymethyloxy)-13-[tetrahydro-5-(1-methoxymethyloxy tridecyl) furan-2-yl] tridecyl}-5-methyl-2-(5H)-furanone (1 mg) in THF (150 uL) is added rapidly. The vial is heated at 65° C. for 15 minutes. After cooling, dimethylsulfide (100 uL) is added, followed by boron trifluoride etherate (200 uL). The vial is heated again to 65° C. for 15 minutes, then cooled. The contents of the vial are diluted with water (4 mL) and passed through a silica gel cartridge (pre-loaded Waters Light C-18 Sep-Pak) to load the sample. The cartridge is rinsed with water and eluted with acetonitrile (2 mL). The acetonitrile is evaporated and the residue is purified via HPLC to provide the desired product.

EXAMPLE 4

4a. 5-methyl-1, 2,3,4-tetramethoxy-6-(1-hydroxytridec-12-yn-1-yl)benzene

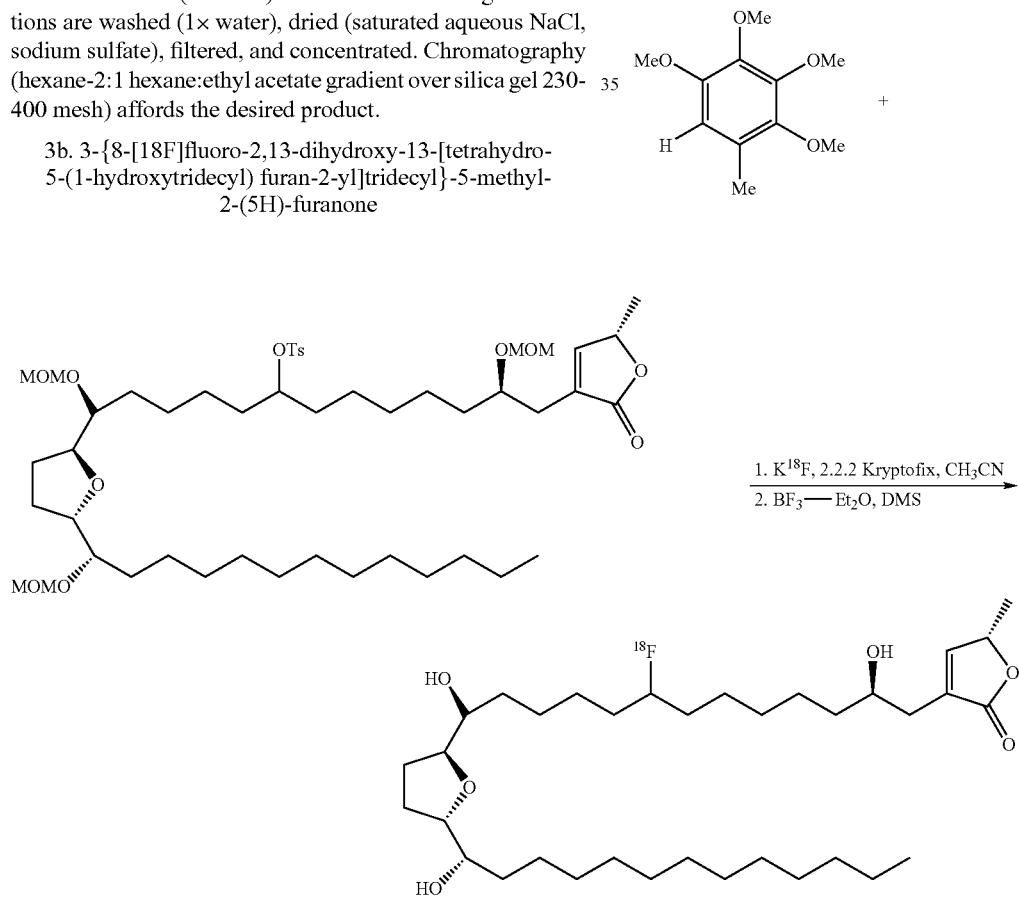

-continued

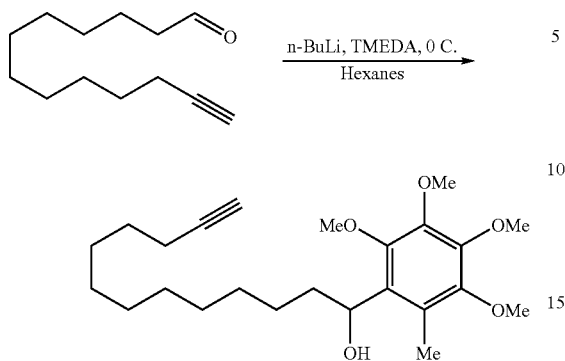

A solution of 5-methyl-1,2,3,4-tetramethoxybenzene (2.12 g, 10 mmol, Hansen, C. A.; Dean, A. B.; Draths, K. M.; Frost, J. W. *J. Am. Chem. Soc.* 1999, 121(15), 3799-3800.) and tetramethylethylenediamine (TMEDA, 2.96 mL, 20 mmol) in hexanes (25 mL) is cooled at 0° C. in an ice bath while a solution of n-butyllithium (2.0M in hexanes, 5 mL) is added dropwise. The yellow reaction mixture is stirred for thirty minutes and is then diluted with THF (20 mL). A solution of 12-tridecynal (4.27 g, 22 mmol, *J. Org. Chem.* 2001, 66(14), 4766-4770) in THF (10 mL) is added, and the mixture stirred for two hours. The reaction is quenched by the addition of saturated aqueous NH$_4$Cl (20 mL). Water (30 mL) is added and the aqueous phase is separated and extracted with ethyl acetate (2×50 mL). The combined organic fractions are washed (1× water), dried (saturated aqueous NaCl, sodium sulfate), filtered, and concentrated. Chromatography (hexane-2:1 hexane:ethyl acetate gradient over silica gel 230-400 mesh) provides the desired product.

4b. 5-methyl-1,2,3,4-tetramethoxy-6-(1-(1,1-dimethylethyl)dimethylsilyloxy tridec-12-yn-1-yl)benzene

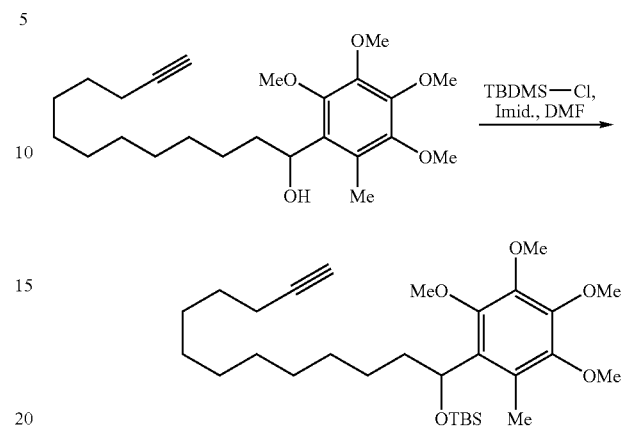

Imidazole (1.36 g, 20 mmol) and 5-methyl-1,2,3,4-tetramethoxy-6-(1-hydroxytridec-12-yn-1-yl)benzene (6.10 g, 15 mmol) are dissolved in DMF (20 mL) and stirred at room temperature while tert-butyldimethylsilyl chloride (2.42 g, 16 mmol) is added as a solid. The resultant solution is stirred at room temperature for two hours, and is poured into water (50 mL). The aqueous phase is separated and extracted with ethyl acetate (2×100 mL). The combined organic fractions are washed (1× water), dried (saturated aqueous NaCl, sodium sulfate), filtered, and concentrated. Chromatography (hexane-2:1 hexane:ethyl acetate gradient over silica gel 230-400 mesh) affords the desired product.

4c. 6-{14-methoxymethyloxy-2-[(1,1-dimethylethyl) dimethylsilyl oxy]-13-[octahydro-5'-(1-(methoxymethyloxy)undecyl) [2.2'-bifuran]-5-yl]tetradeca-12-yn-1-yl}-5-methyl-1,2,3,4-tetramethoxybenzene.

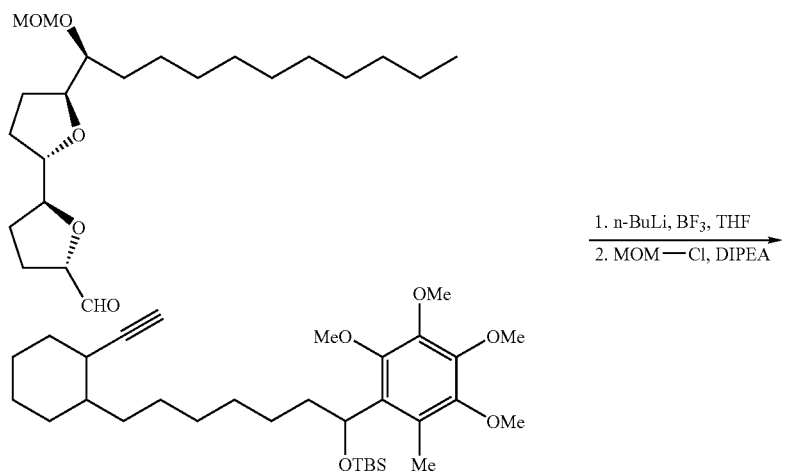

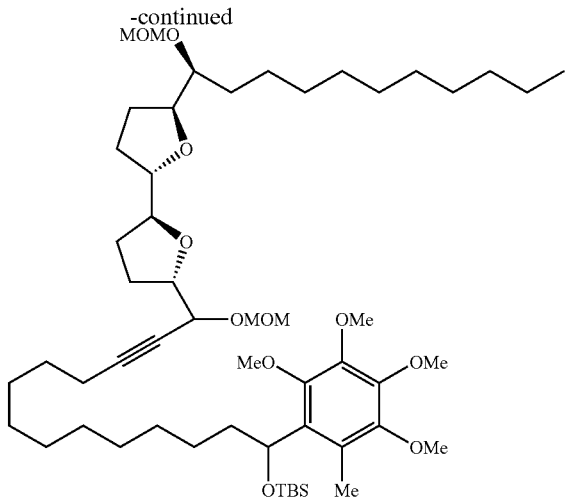

A solution of 5-methyl-1,2,3,4-tetramethoxy-6-(1-(1,1-dimethylethyl)dimethylsilyloxy tridec-12-yn-1-yl)benzene (4.06 g, 10 mmol) in THF (15 mL) is stirred at −78° C. while a solution of n-butyllithium (2.0M in hexanes, 4.95 mL) is added. The mixture is stirred for ten minutes at −78° C. and boron trifluoride etherate (9.9 mmol, 1.25 mL) is added. After another thirty minutes stirring at −78° C., a solution of 5-formyl-octahydro-5'-(1-methoxymethoxy undecyl)-[2.2']-bifuran (1.35 g, 3.5 mmol) in THF (8 mL) is added. The resulting solution is stirred at −78° C. for four hours, and is poured into an aqueous solution of NH$_4$Cl (100 mL, 2.0 M). The mixture is extracted with ethyl acetate (3×100 mL) and the combined organic fractions are washed (1× water), dried (saturated aqueous NaCl, sodium sulfate), filtered, and concentrated. Chromatography (hexane-2:1 hexane:ethyl acetate gradient over silica gel 230-400 mesh) affords 6-{[4-hydroxy-2-[(1,1-dimethylethyl)dimethylsilyl oxy]-13-[octahydro-5'-(1-(methoxymethyloxy)undecyl)-[2.2'-bifuran]-5-yl] tetradeca-12-yn-1-yl}-5-methyl-1,2,3,4-tetramethoxy benzene as an oil.

A solution of this oil (1.81 g, 2 mmol) in diisopropylethylamine (6 mL) is treated with chloromethyl methyl ether (201 mg, 2.5 mmol) at room temperature. After two hours of stirring, the mixture is concentrated in vacuo, and the residue is partitioned between water (50 mL) and ethyl acetate (50 mL). The aqueous phase is separated and extracted with ethyl acetate (2×50 mL) and the combined organic fractions are washed (1× water), dried (saturated aqueous NaCl, sodium sulfate), filtered, and concentrated. Chromatography (hexane-2:1 hexane:ethyl acetate gradient over silica gel 230-400 mesh) affords the desired product as an oil.

4d. 5-{14-methoxymethyloxy-2-[p-toluenesulfonato]-13-[octahydro-5'-(1-(methoxymethyloxy) undecyl) [2.2'-bifuran]-5-yl]tetradec-1-yl}-6-methyl-2,3-dimethoxy-1,4-benzoquinone

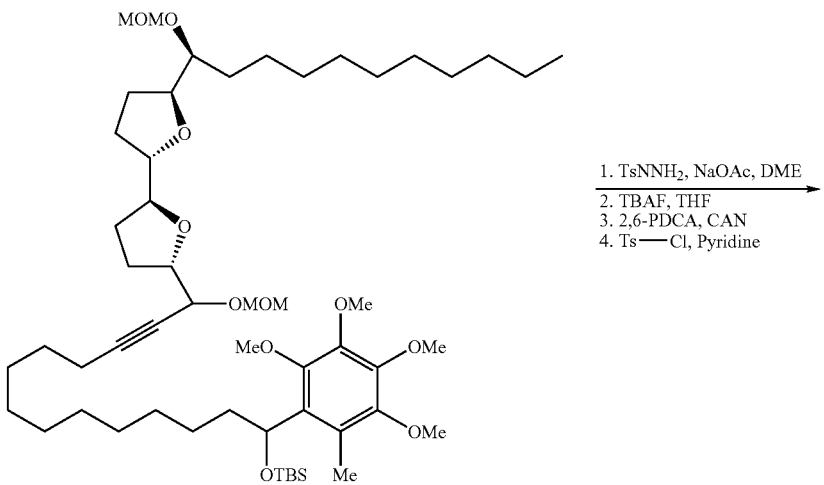

-continued

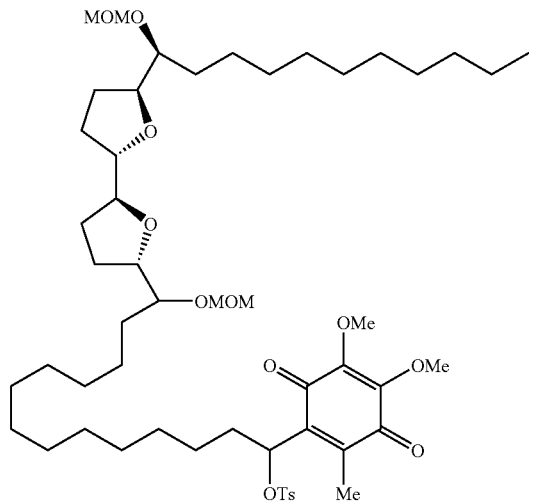

30

A solution of 6-{14-methoxymethyloxy-2-[(1,1-dimethylethyl)dimethylsilyloxy]-13-[octahydro-5'-(1-(methoxymethyloxy)undecyl) [2,2'-bifuran]-5-yl]tetradeca-12-yn-1-yl}-5-methyl-1,2,3,4-tetramethoxybenzene (95 mg, 0.10 mmol) and p-toluenesulfonhydrazide (1.86 g, 10 mmol) in dimethoxyethane (15 mL) is heated at reflux while a solution of NaOAc (984 mg 12 mmol) in water (10 mL) is added over three hours. The mixture is cooled to room temperature and poured into water (100 mL), and extracted with dichloromethane (2×30 mL). The combined organic layers are dried (sodium sulfate), filtered, and concentrated.

The residue is dissolved in THF (5 mL) and TBAF (1.0M in THF, 120 μL) is added. The mixture is stirred at room temperature for 30 minutes and concentrated. The residue is partitioned between water (50 mL) and ethyl acetate (50 mL). The aqueous phase is separated and extracted with ethyl acetate (2×50 mL) and the combined organic fractions are washed (1×water), dried (saturated aqueous NaCl, sodium sulfate), filtered, and concentrated to afford 6-{14-methoxymethyloxy-2-hydroxy-13-[octahydro-5'-(1-(methoxymethyloxy)undecyl) [2.2'-bifuran]-5-yl]tetradec-1-yl}-5-methyl-1,2,3,4-tetramethoxybenzene.

A solution of 6-{14-methoxymethyloxy-2-hydroxy-13-[octahydro-5'-(1-(methoxymethyloxy)undecyl) [2.2'-bifuran]-5-yl]tetradec-1-yl}-5-methyl-1,2,3,4-tetramethoxybenzene (42 mg, 0.05 mmol) and pyridine-2,6-dicarboxylic acid (83.5 mg, 0.5 mmol) in acetonitrile (6 mL) is stirred at 0° C. while a solution of ceric ammonium nitrate (CAN, 180 mg, 0.33 mmol) in acetonitrile/water (1:1, 5 mL) is added dropwise. The mixture is stirred at 0° C. for five hours and is quenched by the addition of CHCl$_3$/2-propanol (1:1, 10 mL) followed by water (10 mL). The layers were separated, and the aqueous phase is extracted with CHCl$_3$/2-propanol (1:1, 3×30 mL). The combined organic fractions are concentrated and the residue is purified by flash chromatography (hexane-2:1 hexane:ethyl acetate gradient over silica gel 230-400 mesh) to afford a yellow solid: 5-{14-methoxymethyloxy-2-hydroxy-13-[octahydro-5'-(1-(methoxymethyloxy)undecyl) [2.2'-bifuran]-5-yl]tetradec-1-yl}-6-methyl-2,3-dimethoxy-1,4-benzoquinone.

The 5-{14-methoxymethyloxy-2-hydroxy-13-[octahydro-5'-(1-(methoxymethyloxy)undecyl) [2.2'-bifuran]-5-yl]tetradec-1-yl}-6-methyl-2,3-dimethoxy-1,4-benzoquinone (84 mg, 0.1 mmol) is dissolved in pyridine (1.0 mL) and p-toluenesulfonyl chloride (28.5 mg, 0.15 mmol) is added. The mixture is stirred at room temperature for two hours, and concentrated in vacuo. The residue is partitioned between ethyl acetate (5 mL) and water (5 mL). The aqueous phase is separated and extracted with ethyl acetate (2×5 mL) and the combined organic fractions are washed (1× water), dried (saturated aqueous NaCl, sodium sulfate), filtered, and concentrated. Chromatography (hexane-2:1 hexane:ethyl acetate gradient over silica gel 230-400 mesh) affords the desired product.

4e. 5-{14-methoxymethyloxy-2-[$^{18}$F]fluoro-13-[octahydro-5'-(1-(methoxymethyloxy)undecyl) [2.2'-bifuran]-5-yl]tetradec-1-yl}-6-methyl-2,3-dimethoxy-1,4-benzoquinone

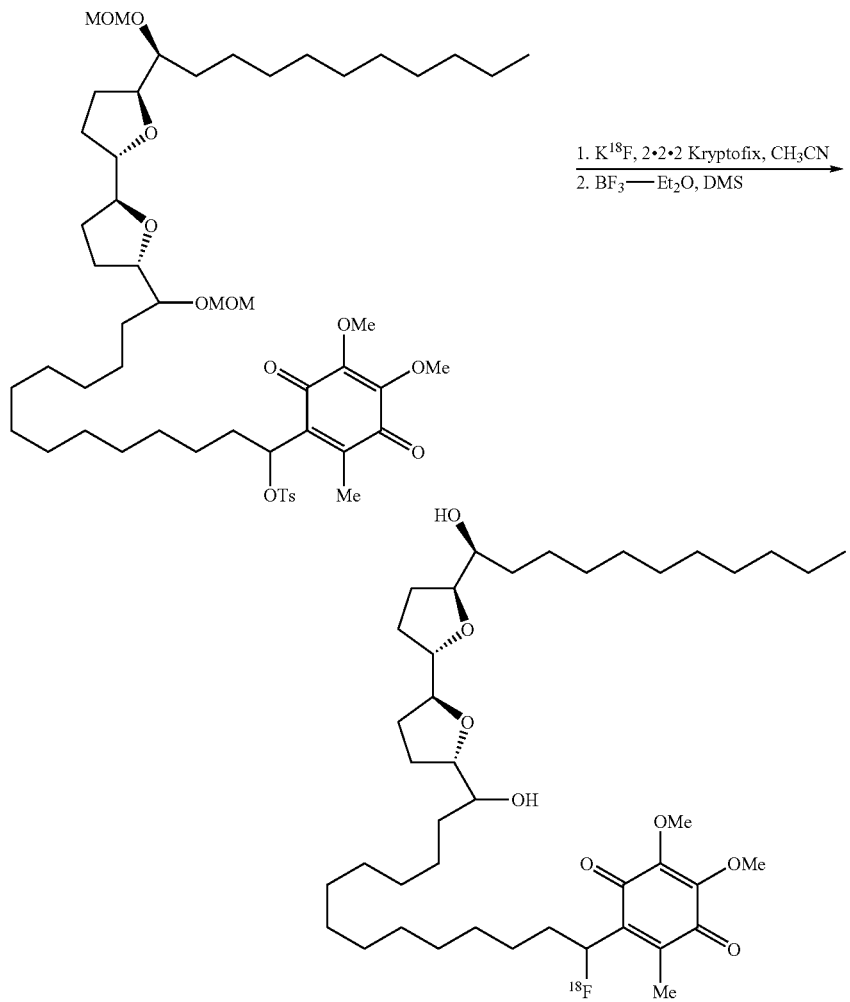

A thin-wall 10 mL, silanized vacutainer with a silanized stopper is charged with tetrabutyl ammonium hydroxide (5 uL, 40% w/v solution in water), and a solution of $^{18}$F$^-$ in water (10 mCi, 200 uL). The resultant mixture is evaporated to dryness under a flow of nitrogen at 100° C. The residue is dried further by repeated cycles of addition and evaporation of acetonitrile (3×200 uL). An additional aliquot of acetonitrile is added and concentrated under vacuum without heating. Prior to complete solvent removal, a solution of 5-{14-methoxymethyloxy-2-[p-toluenesulfonato]-13-[octahydro-5'-(1-(methoxymethyloxy)undecyl) [2.2'-bifuran]-5-yl] tetradec-1-yl}-6-methyl-2,3-dimethoxy-1,4-benzoquinone (1 mg) in THF (150 uL) is added rapidly. The vial is heated at 65° C. for 15 minutes. After cooling, dimethylsulfide (100 uL) is added, followed by boron trifluoride etherate (200 uL). The vial is heated again to 65° C. for 15 minutes, then cooled. The contents of the vial are diluted with water (4 mL) and passed through a silica gel cartridge (pre-loaded Waters Light C-18 Sep-Pak) to load the sample. The cartridge is rinsed with water and eluted with acetonitrile (2 mL). The acetonitrile is evaporated and the residue is purified via HPLC to afford the desired product.

EXAMPLE 5

5a. Succinic acid 4-(4-oxobutyric acid methyl ester) benzyl ester methyl ester

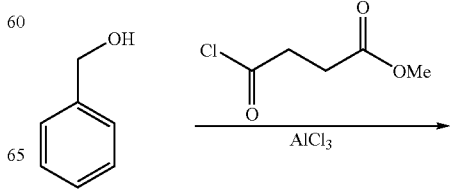

-continued

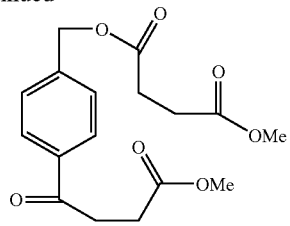

Benzyl alcohol (20 g, 0.185 mol) is added to a 100 mL round bottom flask charged with dichloromethane (50 mL). The flask is cooled to 0° C. Aluminum chloride (1.85 mol) and 3-chlorocarbonyl propionylmethylester (0.37 mol) are then added to the above flask. The mixture is stirred for 3 hours after which water is slowly added to the flask. The contents are poured into a separatory funnel and the layers are separated. The aqueous layer is extracted with dichloromethane and the organic layers are combined and washed with brine and dried over magnesium sulfate, filtered, and concentrated in vacuo to give a crude residue that is used directly in the next step.

5b. 4-[4-(Hydroxymethyl)-phenyl]-4-oxo-butyric acid methyl ester

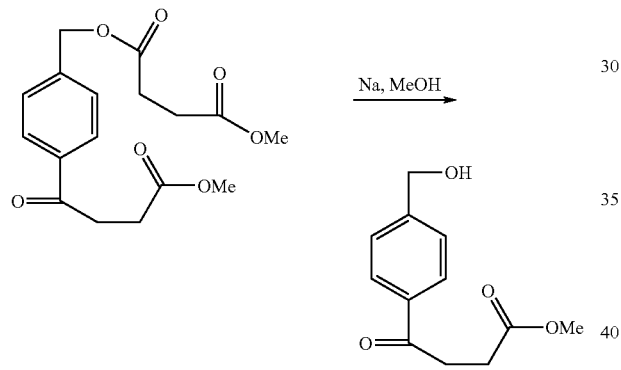

Succinic acid 4-(4-oxobutyric acid methyl ester) benzyl ester methyl ester (15 g, 44.6 mmol) is dissolved in methanol in a 50 mL round bottom flask. Sodium is then added to the above solution until the pH is 9. The solution is stirred for 2 hours after which the methanol is removed on rotary evaporator, the crude residue is taken up in ethyl acetate and washed with water and brine after which it is dried and filtered. The organic solvent is removed in vacuo and the crude so obtained is purified by silica gel flash chromatography (ethyl acetate: hexanes) to obtain the desired product.

5c. 4-[4-(Hydroxymethyl)-phenyl]-butyric acid methyl ester

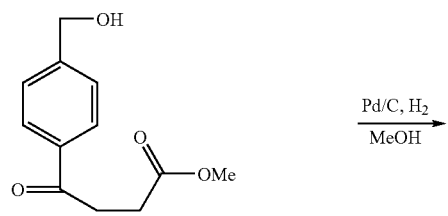

-continued

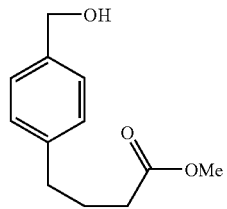

4-[4-(Hydroxymethyl)-phenyl]-4-oxo-butyric acid methyl ester (8 g, 36 mmol) is dissolved in methanol. Pd/C (0.8 g, 10% wt dry basis) is added. The flask is then sealed with a rubber septum and a balloon filled with $H_2$ gas is applied to it. The heterogeneous mixture is then stirred for 4 hours after which the balloon and the stopper are removed and the hydrogen is allowed to escape. The reaction mixture is then filtered through a pad of diatomaceous earth (Celite®) and the filtrate so obtained is concentrated in vacuo to provide the desired product.

5d. 2-thio-3-methyl chromen-4-one

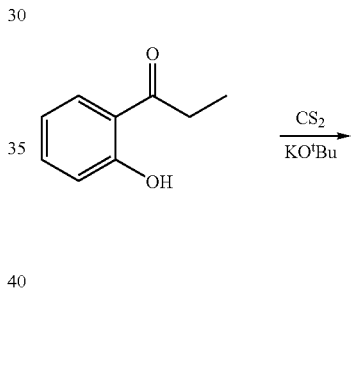

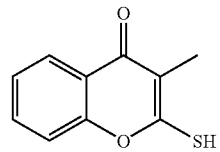

$C_{10}H_8O_2S$
Exact Mass: 192.02

To a 250 mL round bottom flask charged with potassium tert-butoxide (0.599 mmol) is added dropwise a solution of 1-(2-Hydroxy-phenyl)-propan-1-one (30 g, 0.199 mol mmol) and carbon disulfide (0.24 mmol) in 75 mL of toluene with cooling to maintain the temperature between 15-22° C. The reaction mixture is stirred for 4 days at room temperature after which it is poured into water (250 mL). The aqueous layer is separated, washed with dichloromethane and acidified with acetic acid until pH is 5. This is stirred again for 2 hours after which the aqueous layer is poured into a separatory funnel and extracted with dichloromethane (3×30 mL). The organic layer is then washed with saturated solution of sodium bicarbonate followed by water. The organic layer is then dried with brine and then over sodium sulfate and filtered. The crude material obtained after removing the organic solvent is purified by flash chromatography (ether:hexanes) to afford pure 2-thio-3-methyl chromen-4-one.

5e. 2-(4-(butyric acid methylester)phenyl methyl)thio 3-methyl chromen-4-one

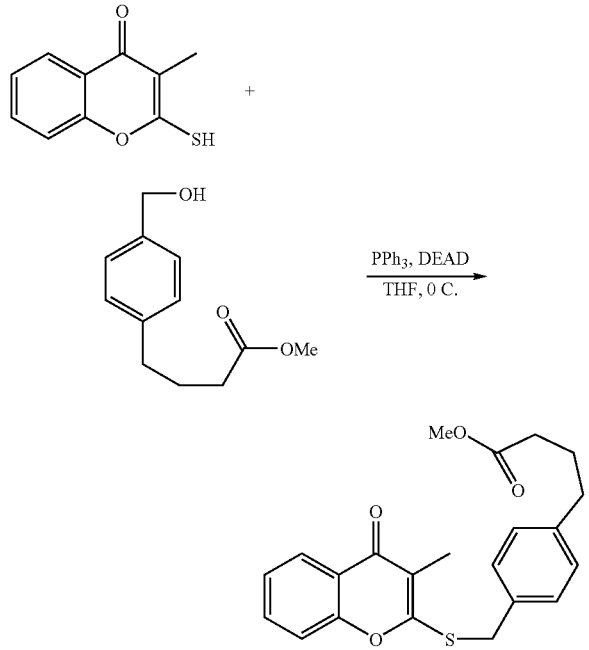

A 50 mL round bottom flask is charged with triphenylphosphine (33.6 mmol) and diethylazodicarboxylate (3.6 mmol). THF (30 mL) is then added to the flask and the flask is cooled to 0° C. The above mixture is stirred for 30 minutes after which 2-thio-3-methyl chromen-4-one (22.4 mmol) and 4-[4-(Hydroxymethyl)-phenyl]-butyric acid methyl ester (7 g, 33.6 mmol) are added in one lot. The reaction mixture is allowed to warm to room temperature and stirred for 24 hours. 5% NaHCO$_3$ (10 mL) is then added and the mixture poured into a separatory funnel. The aqueous layer is then extracted with ethyl acetate (2×25 mL) and the combined organic layers were washed with brine and then dried over magnesium sulfate, filtered, and concentrated in vacuo. Purification of the residue by flash chromatography (ethyl acetate:hexanes) affords the above product.

5f. 2-(4-(4-hydroxybutyl)phenyl methyl)thio 3-methyl chromen-4-one

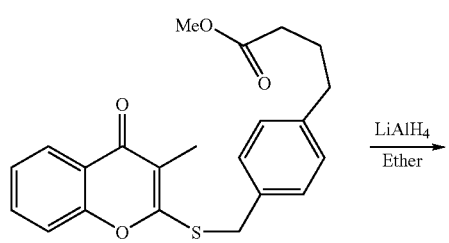

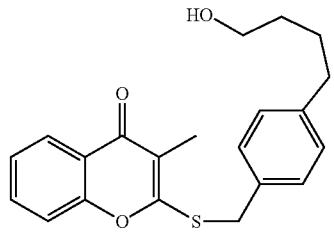

Lithium aluminum hydride (33.2 mmol) is charged to a 50 mL round bottom flask and ether (25 mL) is added to it and the flask is cooled to 0° C. 2-(4-(butyric acid methylester)phenyl methyl)thio 3-methyl chromen-4-one (7.5 g, 22.15 mmol) dissolved in ether is slowly added to the above flask via a pressure equalizing addition funnel. The reaction mixture is stirred for 3 hours after which water (1.25 mL), 15% NaOH (1.25 mL) and the water (3.7 mL) are added sequentially to it. This is allowed to stir for 20 minutes after which the contents are filtered. The filtrate is washed with water and brine and dried over sodium sulfate, filtered, and concentrated in vacuo to give a residue which is purified by silica gel flash chromatography (ethyl ether: hexanes) to give the above product.

5 g. 2-(4-(4-tosyloxybutyl)phenyl methyl)thio 3-methyl chromen-4-one

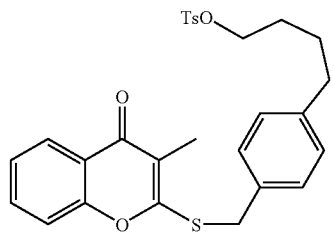

A 50 mL round bottom flask is charged with 2-(4-(4-hydroxybutyl)phenyl methyl)thio 3-methyl chromen-4-one (6.0 g, 16.9 mmol) and pyridine (15 mL) is added to it. Toluenesulfonyl chloride (25.4 mmol) is then added in one lot and the mixture is stirred for 8 hours after which water and ethyl acetate are added to it. The contents are poured into a separatory funnel and the layers separated. The organic layer is washed with 5% CuSO$_4$ (2×10 mL) and then with water and brine. It is then dried over magnesium sulfate, filtered, and concentrated in vacuo. The residue obtained is purified by silica gel flash chromatography (ethyl acetate:hexanes) to afford the product.

5h. 2-(4-(4-fluorobutyl)phenyl methyl)thio 3-methyl chromen-4-one

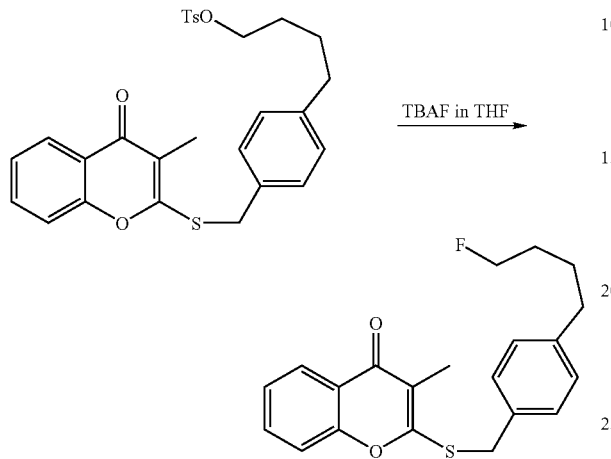

2-(4-(4-tosyloxybutyl)phenyl methyl)thio 3-methyl chromen-4-one (7.5 g, 14.7 mmol)is dissolved in THF in a 25 mL round bottom flask. Tetrabutyammonium fluoride (14.7 mmol) solution (1M in THF) is then added to it and the solution heated to reflux for 2 hours. The contents are concentrated on the rotary evaporator and the residue obtained is purified by silica gel flash chromatography (ethyl acetate hexanes).

5i. 2-(4-(4-[18F]-fluorobutyl)phenyl methyl)thio 3-methyl chromen-4-one

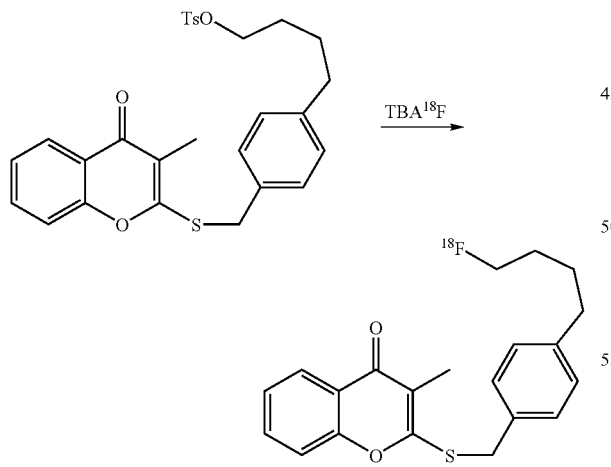

Aqueous 18F (16 mCi, 0.1 mL) is added to a vacutainer containing 5 µl of tetrabutylammonium hydroxide (40% wt sol. in water). The mixture is concentrated under nitrogen in an oil bath at 100° C. and 250 µL of acetonitrile is added and this too is concentrated under nitrogen. The procedure is repeated twice and then 100 µL of acetonitrile is added to it and the contents subjected to vacuum. THF is added prior to the point of dryness, followed by 5 mg of 2-(4-(4-tosyloxybutyl)phenyl methyl)thio 3-methyl chromen-4-one. The mixture is then heated in an oil bath at 70° C. for 30 minutes. This is then diluted with water, applied to a C18 Sep-Pak, rinsed with water and eluted with acetonitrile to get the above mentioned compound.

EXAMPLE 6

6a. Synthesis of 2-ethylthio-3-methyl chromen-4-one

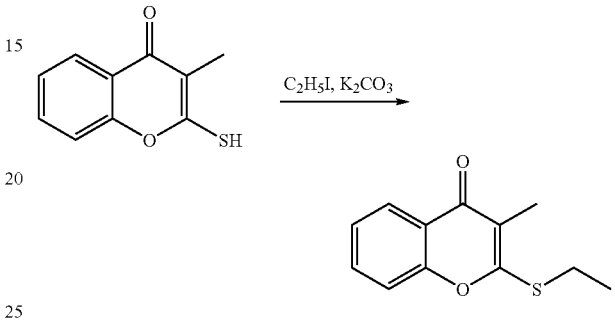

To a round bottom flask containing 2-thio-3-methyl chromen-4-one (10 g, 52 mmol) is added DMF. Iodoethane (62.4 mmol) and potassium carbonate (62.4 mmol) are then added to the flask and the reaction mixture is stirred for 3 hours. Water is then added to the reaction and it is poured into a separatory funnel. The aqueous layer then is extracted with ethyl acetate (2×25 mL). The combined organic layers are then washed with water and brine and dried over magnesium sulfate, filtered, and concentrated. The residue obtained after concentration of the organic layer is purified by silica gel flash chromatography (ethyl ether: hexanes) to provide the desired product.

6b. 2-ethylsulfinyl-3-hydroxymethyl chromen-4-one

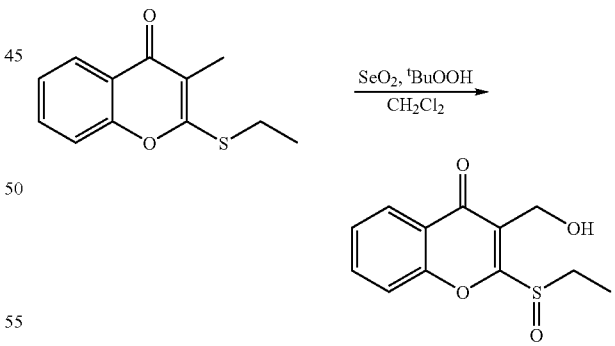

A 50 mL round bottom flask is charged with selenium dioxide (13.6 mmol) and 90% tert-butyl hydroperoxide (54.5 mmol). To this is then added dichloromethane (25 mL) and the mixture is stirred for 30 minutes at room temperature. 2-Ethylthio-3-methyl chromen-4-one (6 g, 27.2 mmol) is added to the flask and the reaction mixture stirred for 10 hours. The dichloromethane is removed on the rotary evaporator and ether is added to the residue. The organic phase is washed with 10% KOH and once with brine. The solvent is again removed and cold acetic acid and methyl sulfide is added to the flask. The contents are stirred for a few hours after which 20% K₂CO₃ is added to the flask. The aqueous phase is extracted with ethyl acetate, washed with water and brine and dried over sodium sulfate, filtered, and concentrated. The residue obtained after concentration is purified by using silica gel flash chromatography (ethyl ether:hexanes).

6c. 2-ethylsulfinyl-3-((2-tetrahydropyranyloxy)methyl) chromen-4-one

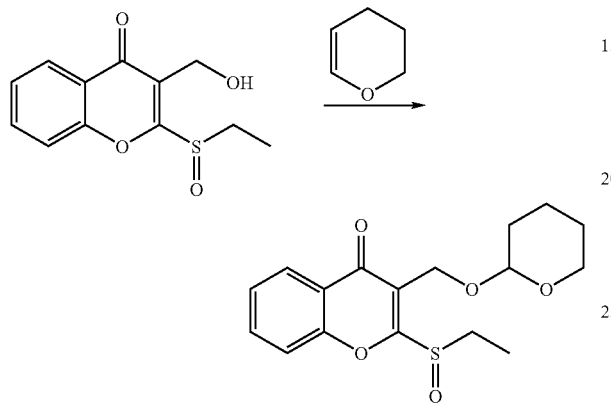

To 2-ethylsulfinyl-3-hydroxymethyl chromen-4-one (5 g, 19.8 mmol) dissolved in dichloromethane (20 mL) in a 25 mL round bottom flask is added dihydropyran (29.7 mmol) and toluenesulfonic acid (0.99 mol). The reaction mixture is stirred for 3 hours after which it is poured into a separatory funnel and water is added. Ethyl acetate is then added and the layers are separated. The organic layer is washed with water (3×10) and brine and dried over sodium sulfate and filtered. The filtrate is concentrated in vacuo and the residue obtained is purified by silica gel flash chromatography (ethyl ether:hexanes) to yield the above product.

6d. 2-(4-tertbutylbenzyl)thio-3-((2-tetrahydropyranyloxy)methyl) chromen-4-one

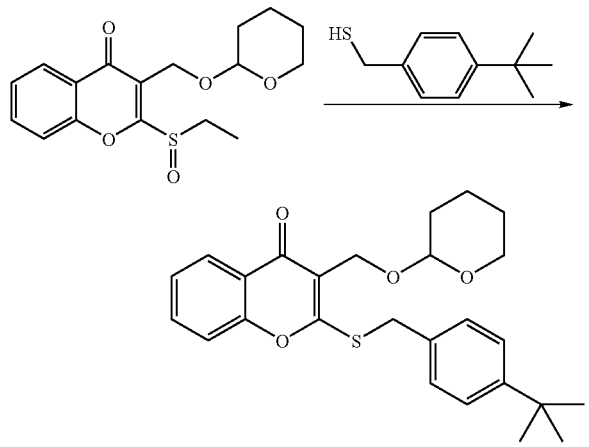

Into a 25 mL round bottom flask is introduced 2-ethylsulfinyl-3-((2-tetrahydropyranyloxy)methyl) chromen-4-one (5 g, 14.87 mmol). Acetonitrile is then added to it followed by 4-tertbutylbenzyl mercaptan (74.3 mmol). The reaction mixture is stirred for 10 hours at room temperature after which the solvent is removed in vacuo. The crude residue obtained is purified by silica gel chromatography (ethyl acetate:hexanes) to obtain the product.

6e. 2-(4-tert-butylbenzyl)thio-3-hydroxymethyl chromen-4-one

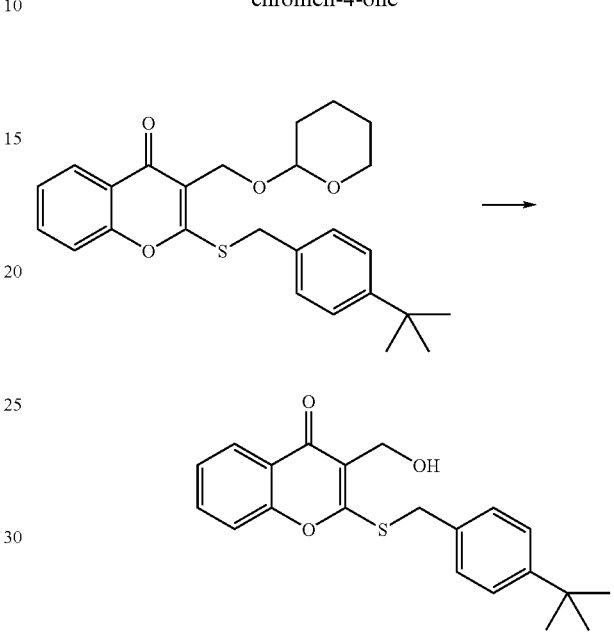

2-(4-Tertbutylbenzyl)thio-3-((2-tetrahydropyranyloxy) methyl) chromen-4-one (5.5 g, 12.55 mmol) is dissolved in tetrahydrofuran in a 50 mL round bottom flask. Acetic acid and water are then added such that the ratio of THF:Acetic acid:Water is 4:2:1 (28 mL). The flask is warmed to 45° C. and the mixture stirred for 3 hours. After cooling the flask the contents are poured into a separatory funnel and the aqueous layer extracted with ethyl acetate. The organic layer is then washed with water and brine and dried over sodium sulfate and filtered. The filtrate is concentrated in vacuo and the residue obtained is purified by silica gel flash chromatography (ethyl acetate:hexanes) to give the above-mentioned product.

6f. 2-(4-tert-butylbenzyl)thio-3-tosyloxymethyl chromen-4-one

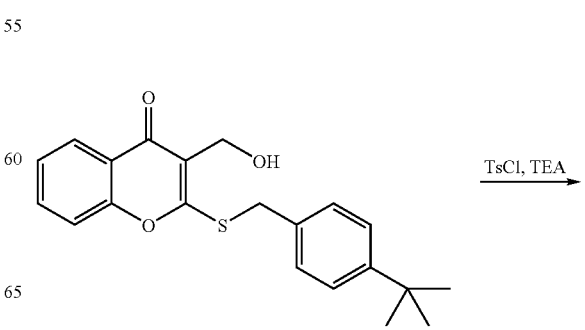

-continued

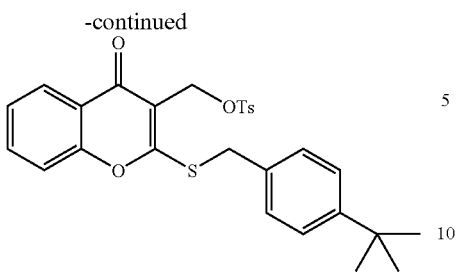

Into a 25 mL round bottom flask is introduced 2-(4-tert-butylbenzyl)thio-3-hydroxymethyl chromen-4-one (3 g, 8.47 mmol) and this is dissolved in dichloromethane (10 mL). Toluenesulfonyl chloride (12.7 mmol) and triethylamine (12.7 mmol) are then added to it and the reaction mixture is stirred for 4 hours at room temperature. The solvent is then removed in vacuo and the residue obtained is purified by silica gel flash chromatography (ethyl acetate:hexanes) to get the above-mentioned compound.

6g. 2-(4-tert-butylbenzyl)thio-3-fluoromethyl chromen-4-one

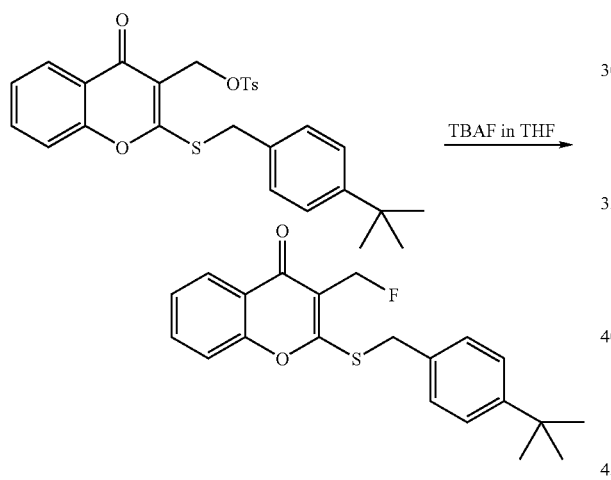

2-(4-Tert-butylbenzyl)thio-3-tosyloxymethyl chromen-4-one (3 g, 5.9 mmol) is introduced into a 15 mL round bottom flask and tetrabutylammonium fluoride solution (5.9 mmol; 1M in THF) is added to it. The solution is heated to reflux for 3 hours after which all volatiles are removed and the residue obtained is purified by silica gel flash chromatography (ethyl acetate:hexanes).

6h. 2-(4-tert-butylbenzyl)thio-3-[18F]-fluoromethyl chromen-4-one

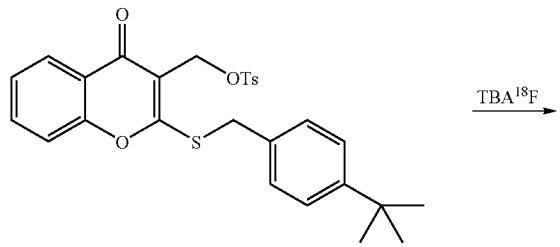

-continued

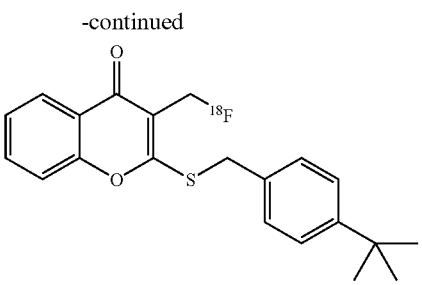

Aqueous 18F (16 mCi, 0.1 mL) is added to a vacutainer containing 5 μl of tetrabutylammonium hydroxide (40% wt sol. in water). The mixture is concentrated under nitrogen in an oil bath at 100° C. and 250 μL of acetonitrile is added and this too is concentrated under nitrogen. The procedure is repeated twice and then 100 μL of acetonitrile is added to it and the contents subjected to vacuum. Prior to complete dryness, THF is added, followed by 5 mg of 2-(4-tert-butylbenzyl)thio-3-tosyloxymethyl chromen-4-one. The mixture is then heated in an oil bath at 70° C. for 30 minutes. This is then diluted with water, applied to a C18 Sep-Pak, rinsed with water and eluted with acetonitrile to get the above mentioned compound

EXAMPLE 7

7a. 2'-tertbutoxy-6'-hydroxy propiophenone

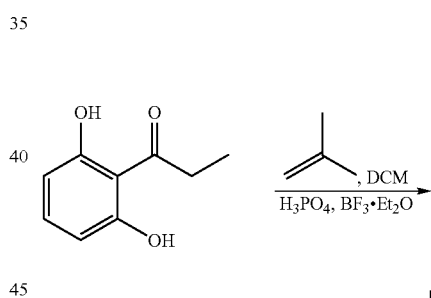

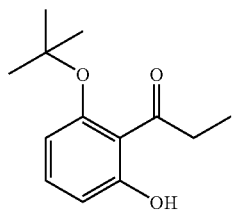

To a 100 mL round bottom flask is added 2',6'dihydroxypropiophenone (25 g, 0.15 mol) and to it is then added dichloromethane (50 mL). This is then cooled to −75° C. and then 2.6 mL of $H_3PO_4$ is added to it followed by 6.22 mL of boron trifluoride etherate and then isobutylene (125 mL). The reaction is then stirred at −75° C. for 1.5 hrs and then at room temperature overnight. The reaction mixture is then poured into a 2N ammonium hydroxide solution (200 mL) and extracted with dichloromethane. The organic layer is then washed with water and then with brine and dried over sodium sulfate and filtered. The crude residue obtained after concentration of the filtrate is purified by flash chromatography using silica gel (ethyl acetate:hexanes) to afford the above product.

7b. 5-tertbutoxy-2-thio-3-methyl chromen-4-one

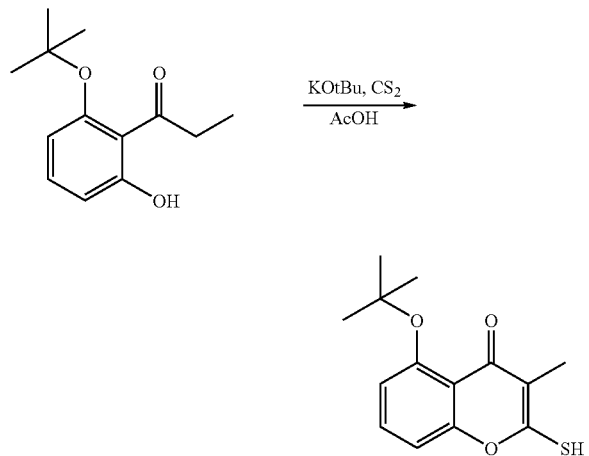

To a 100 mL round bottom flask charged with potassium tert-butoxide (270 mmol) is added dropwise a solution of 2'-tertbutoxy-6'-hydroxy propiophenone (20 g, 90 mmol) and carbon disulfide (99 mmol) in 50 mL of toluene with cooling to maintain the temperature between 15-22° C. The reaction mixture is stirred for 4 days at room temperature after which it is poured into water (250 mL). The aqueous layer is separated, washed with dichloromethane and acidified with acetic acid till pH is 5. This is stirred again for 2 hours after which the aqueous layer is poured into a separatory funnel and extracted with dichloromethane (3×40 mL). The organic layer is then washed with saturated solution of sodium bicarbonate followed by water. The organic layer is then dried with brine and then over sodium sulfate and filtered. The crude material obtained after concentrating the filtrate is purified by flash chromatography to afford pure 2-thio-3-methyl chromen-4-one.

7c. 2-(4-tertbutylbenzylmercapto)-3-methyl-5-tertbutoxy chromen-4-one

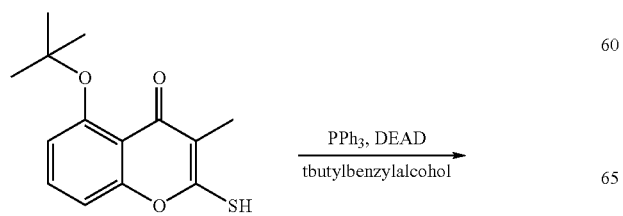

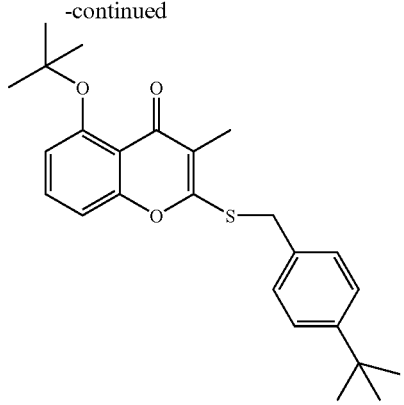

A 50 mL round bottom flask is charged with triphenylphosphine (37.8 mmol) and diethylazodicarboxylate (37.8 mmol). THF (20 mL) is then added to the flask and the flask is cooled to 0° C. The above mixture is stirred for 30 minutes after which 2-thio-3-methyl 5-tert-butoxy chromen-4-one (10 g, 37.8 mmol) and 4-tertbutylbenzylalcohol (38 mmol) are added in one lot. The reaction mixture is allowed to warm to room temperature and stirred for 24 hours. 5% NaHCO$_3$ is then added and the mixture poured into a separatory funnel. The aqueous layer is then extracted with ethyl acetate (2×25 mL) and the combined organic layers were washed with brine and then dried over magnesium sulfate, filtered, and concentrated in vacuo. Purification of the residue by flash chromatography affords the above product.

7d. 2-(4-tertbutylbenzylmercapto)-3-methyl-5-hydroxy chromen-4-one

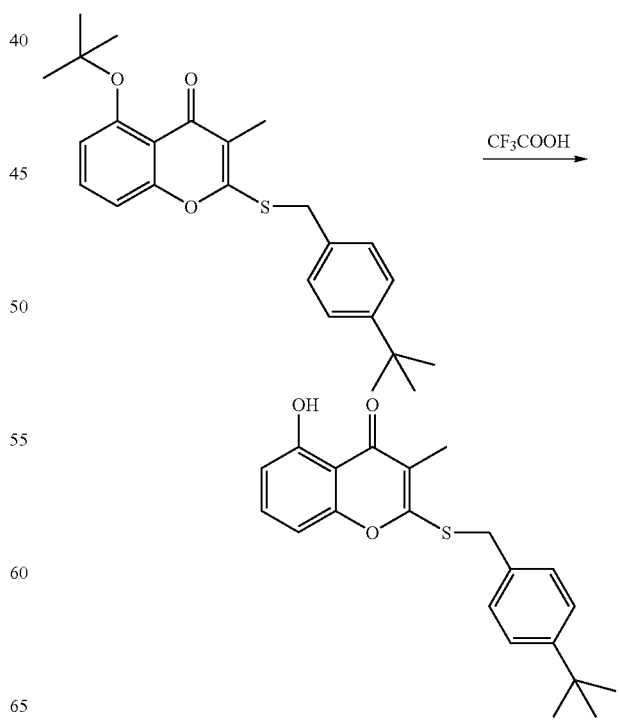

A 50 mL round bottomed flask is charged with 2-(4-tert-butylbenzylmercapto)-3-methyl-5-tertbutoxy chromen-4-one (10 g, 24.3 mmol). To this is then added anhydrous trifluoroacetic acid (15 mL) and the reaction mixture is stirred for 8 hours at 0° C. Dichloromethane is then added to the flask and the mixture poured into a separatory funnel. It is then washed with water and then with brine and dried over sodium sulfate and filtered. The filtrate is then concentrated in vacuo and the residue obtained is purified by silica gel flash chromatography (ethyl acetate:hexanes) to obtain the desired product.

7e. 2-(4-tertbutylbenzylmercapto)-3-methyl-5-tosyloxy chromen-4-one 2-(4-tert-butylbenzylmercapto)-3-methyl-5-hydroxy chromen-4-one (5 g, 14.1 mmol) is dissolved in pyridine in a 25 mL round bottom flask and p-toluenesulfonyl chloride (15 mmol) is added to it. The reaction mixture is stirred for 8 hours. Water is then added to the flask and the contents are poured into a separatory funnel. Ethyl acetate is added and the layers are separated. The organic layer is then washed with water and brine and dried over sodium sulfate and filtered. The filtrate is concentrated in vacuo and the residue obtained is purified by silica gel flash chromatography (hexanes:ethyl acetate) to afford the above product.

7f. 2-(4-tertbutylbenzylmercapto)-3-methyl-5-fluoro chromen-4-one

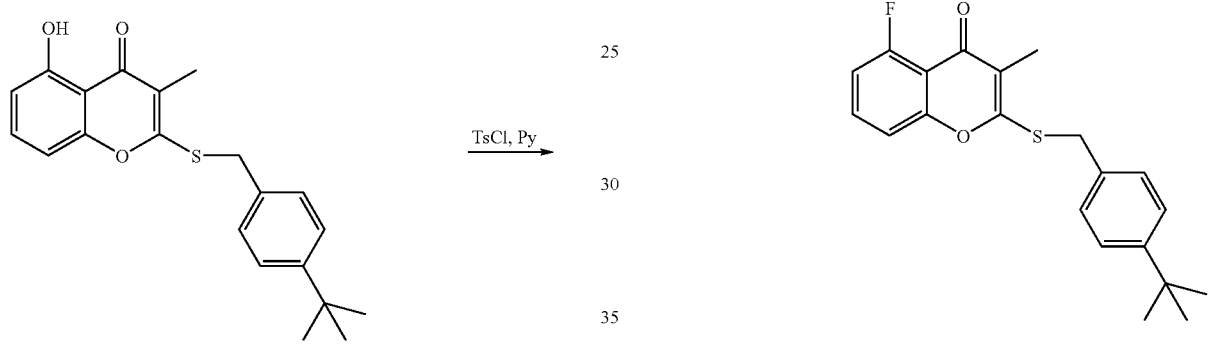

2-(4-tertbutylbenzylmercapto)-3-methyl-5-tosyloxy chromen-4-one (200 mg, 0.39 mmol) is dissolved in THF in a 15 mL round bottom flask and potassium fluoride (0.39 mmol) and Kryptofix (0.39 mmol) are added to it. The solution is heated to reflux for 3 hours after which it is cooled to room temperature. The reaction mixture is then concentrated and the crude residue obtained is purified by silica gel flash chromatography to obtain the above product.

7g. 2-(4-tertbutylbenzylmercapto)-3-methyl-5-[$^{18}$F]-fluoro chromen-4-one

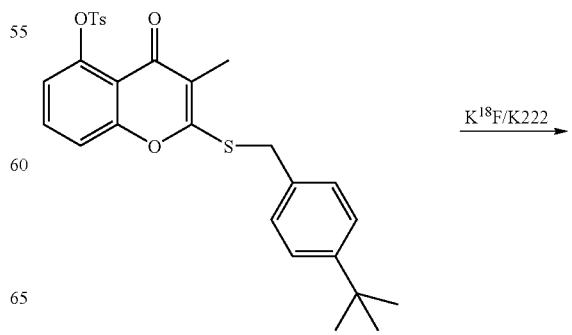

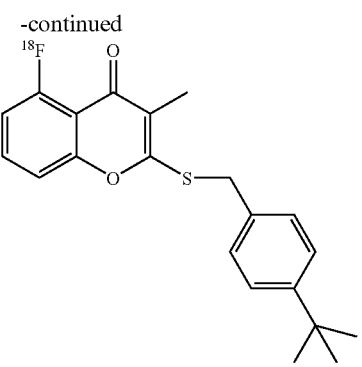

To a 5 mL reaction vial containing 100 mCi of 18F in 300 mg of $^{18}$O water is added a 1 mL solution consisting of 10 mg of Kryptofix, 1 mg potassium carbonate, 0.005 mL water and 0.95 mL acetonitrile. The vial is heated to remove all the solvents and dry acetonitrile (1 mL) is added to the vial. This is also removed by evaporation. 2-(4-tertbutylbenzylmercapto)-3-methyl-5-tosyloxy chromen-4-one (5 mg) in acetonitrile is then added to it. The vial is sealed and heated for 30 minutes at 100° C. The mixture is diluted with dichloromethane and passed through a Sep-Pak and eluted with tetrahydrofuran. The solvent is evaporated to get desired compound.

EXAMPLE 8

8a. 2-bromo-1-(2,2-dimethyl-chromen-6-yl)-2-(3, 4, 5-trimethoxy-phenyl)-ethanone

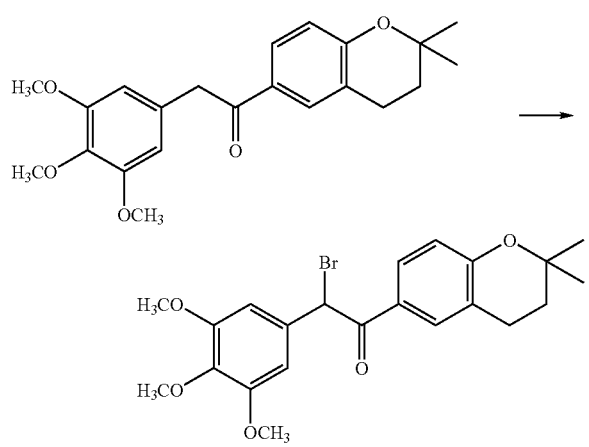

To a solution of 1-(2,2-dimethyl-chroman-6-yl)-2-(3,4,5-trimethoxy-phenyl)-ethanone (37 g, 0.1 mol, *Chemistry and Biology* 2000, 7, 979) in carbon tetrachloride (300 mL) is added bromine (16.0 g, 0.1 mol) at such a rate to obtain a continuous discoloration of the reaction mixture. After the addition is complete (about 10 minutes), the reaction mixture is evaporated under reduced pressure to obtain 2-bromo-1-(2, 2-dimethyl-chroman-6-yl)-2-(3,4,5-trimethoxy-phenyl)-ethanone, which is used in the next step without further purification.

8b. 2-[$^{18}$F]fluoro-1-(2,2-dimethyl-chroman-6-yl)-2-(3,4,5-trimethoxy-phenyl)-ethanone

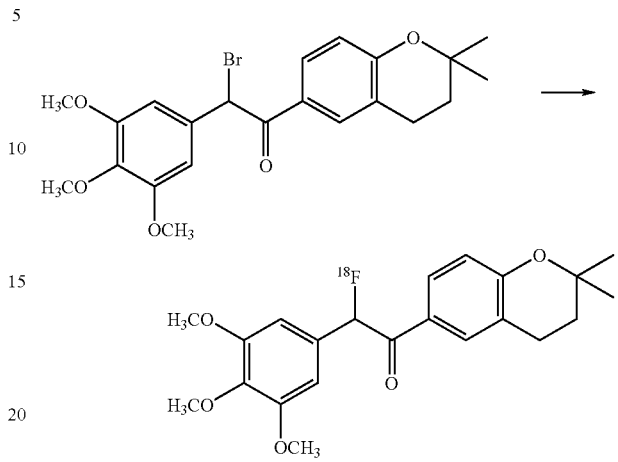

To a 5 mL reaction vial containing 50 mCi of $^{18}$F in 300 mg of 18O water is added a 1 mL solution consisting of 10 mg of Kryptofix, 1 mg potassium carbonate, 0.005 mL water and 0.95 mL acetonitrile. The vial is heated to remove all the solvents and dry acetonitrile (1 mL) is added again to the vial, which is removed once more under vacuum. Tributyl-[2-(2, 2-dimethyl-2H-chromen-6-yl)-3-(3,4,5-trimethoxy-phenyl)-propenyl]-stannane (5 mg) in acetonitrile is then added to the vial. The vial is sealed and heated for 30 minutes to 100° C. The mixture is diluted with dichloromethane and passed through a Sep-Pak and eluted with THF. The filtrate is concentrated to obtain 2-[$^{18}$F]fluoro-1-(2,2-dimethyl-chroman-6-yl)-2-(3,4,5-trimethoxy-phenyl)-ethanone.

EXAMPLE 9

9a. 1-(2,2-dimethyl-2H-chromen-6-yl)-2-hydroxy-2-(3,4,5-trimethoxy-phenyl)-ethanone

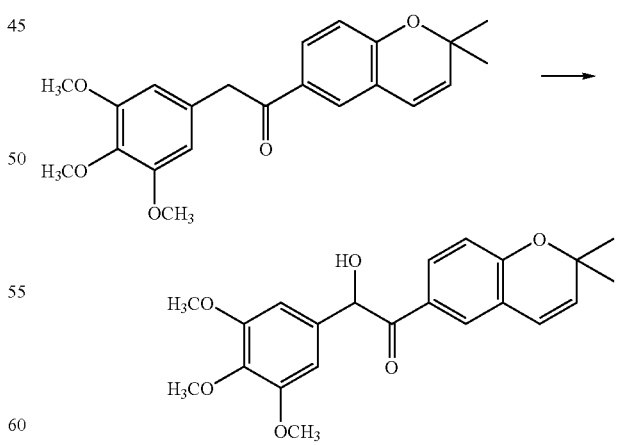

The 1-(2,2-dimethyl-chroman-6-yl)-2-(3,4,5-trimethoxy-phenyl)-ethanone (184.1 mg, 0.5 mmol) dissolved in THF (3 mL) is added dropwise to a stirring cold (−78° C.) solution of NaHMDS (0.6 mL, 1.0M in THF) in THF (3 mL). The resulting reaction mixture is stirred for 30 minutes before (+/−)- camphoryl-sulfonyloxaziridine (187 mg, 0.75 mmol) in THF (3 mL) is added dropwise. After 15 minutes the reaction mixture is quenched with sat. NH$_4$I (aqueous) solution (3 mL) and diluted with diethyl ether. The mixture is allowed to warm up to room temperature. The aqueous layer is extracted with diethyl ether. Combined organic layers are washed with water, brine, dried over sodium sulfate, filtered, and concentrated. Crude 1-(2,2-dimethyl-2H-chromen-6-yl)-2-hydroxy-2-(3,4,5-trimethoxy-phenyl)-ethanone is purified using silica gel chromatography.

9b. Toluene-4-sulfonic acid 2-(2,2-dimethyl-2H-chromen-6-yl)-2-oxo-1-(3,4,5-trimethoxy-phenyl)-ethyl ester

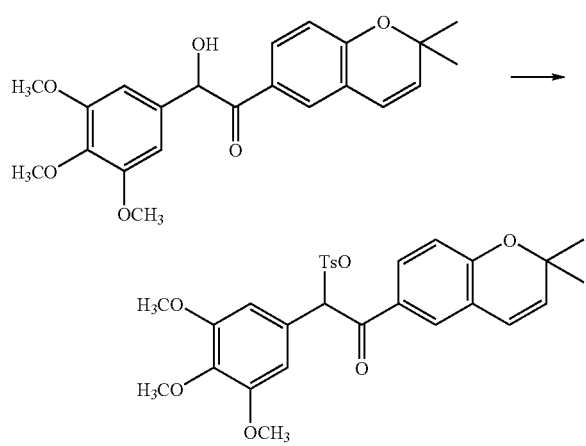

To a stirred solution of 1-(2,2-dimethyl-2H-chromen-6-yl)-2-hydroxy-2-(3,4,5-trimethoxy-phenyl)-ethanone (28 mg, 0.073 mmol) in dichloromethane (1.5 mL) is added p-toluenesulfonyl chloride (15.3 mg, 0.080 mmol) and pyridine (6.47 µL, 0.080 mmol). The reaction mixture continues to stir at room temperature. The crude material is purified using silica gel chromatography.

9c. 1-(2,2-dimethyl-2H-chromen-6-yl)-2-[18F]fluoro-2-(3,4,5-trimethoxy-phenyl)-ethanone

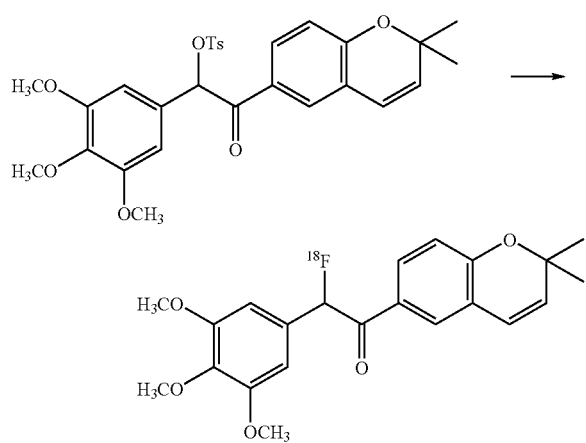

A thin-wall 10 mL, silanized vacutainer with a silanized stopper is charged with tetrabutyl ammonium hydroxide (5 uL, 40% w/v solution in water), and a solution of 18F– in water (10 mCi, 200 uL). The resultant mixture is evaporated to dryness under a flow of nitrogen at 100° C. The residue is further dried by repeated addition and evaporation of acetonitrile (3×200 uL). An additional aliquot of acetonitrile is added and concentrated under vacuum without heating. Prior to complete solvent removal, THF (150 uL) is added, the vial is uncrimped and toluene-4-sulfonic acid 2-(2,2-dimethyl-2H-chromen-6-yl)-2-oxo-1-(3,4,5-trimethoxy-phenyl)-ethyl ester (2 mg) is added in one portion. The vial is recapped and heated at 65° C. for 30 minutes. After cooling, the vial is diluted with water (4 mL) and passed through a silica gel cartridge (pre-loaded Waters Light C-18 Sep-Pak) to load the sample. The cartridge is rinsed with water and eluted with acetonitrile (2 mL). The acetonitrile is evaporated and the residue is purified via HPLC to afford the desired product.

EXAMPLE 10

10a. 6-[2-iodo-1-(3,4,5-trimethoxy-benyl)-vinyl]-2,2-dimethyl-2H-chromene

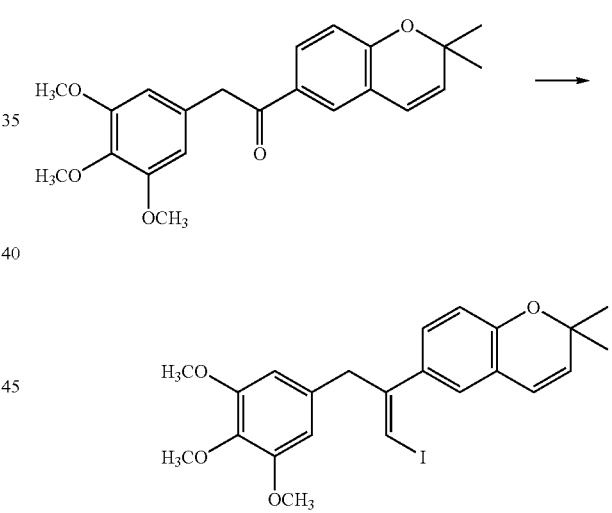

Diodomethane (26.88 g, 0.1 mol) and triphenyl phosphine (26.23 g 0.1 mol) are dissolved ether at stirred at room temperature for 24 hours. The resulting ylide salt is collected by filtration and dried under vacuum. The ylide salt is dissolved in THF (100 mL) and cooled to –78° C. N-sodium hexamethyldisilazide (18.34 g, 0.1 mol) is added dropwise to the stirring reaction mixture. The reaction mixture is stirred for another 30 minutes. The ketone (36.82 g, 0.1 mol) dissolved in THF (50 mL) is added to the reaction mixture. The reaction is warmed to 0° C. After 2 hours the reaction is quenched with sat. NH$_4$Cl (aq). The aqueous layer is extracted with diethyl ether. Combined organic layers are washed with water, brine, dried over sodium sulfate, filtered, concentrated, and purified by chromatography.

10b. Tributyl-[2-(2,2-dimethyl-2H-chromen-6-yl)-3-(3, 4, 5-trimethoxy-phenyl)-propenyl]-stannane

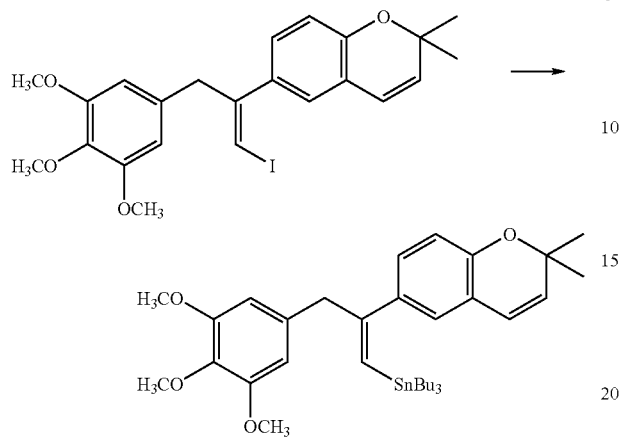

To a solution of 6-[2-iodo-1-(3,4,5-trimethoxy-benyl)-vinyl]-2,2-dimethyl-2H-chromene (974 mg, 1.98 mmol) in 1,4-dioxane (9 mL) is added tri-n-butylethenyl-stannane (650 mg, 2.05 mmol), LiCl (252 mg, 594 mmol), Pd(PPh$_3$)$_4$ (46 mg, 0.04 mmol), and a few crystals of 2,6-di-tert-butyl-4-methyl phenol. The resulting suspension is heated to reflux for 4 hours, cooled to room temperature and treated with pyridine (1 mL) and pyridinium fluoride (2 mL, 1.4 M solution in THF, 2.8 mmol). The resulting mixture is stirred at room temperature for 16 hours and then diluted with diethyl ether and filtered through a small pad of diatomaceous earth (Celite®). The filtrate is washed with water, 10% HCl, water, brine, and dried over sodium sulfate, filtered, and concentrated. Crude material is used in the next step without further purification.

10c. 6-[2-[18F]fluoro-1-(3,4,5-trimethoxy-benyl)-vinyl]-2,2-dimethyl-2H-chromene

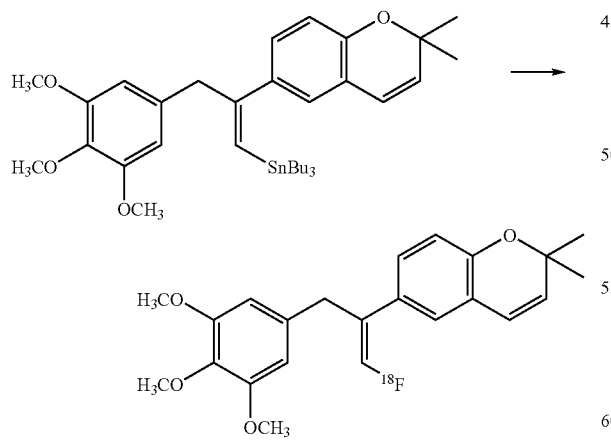

To a 5 mL reaction vial containing 50 mCi of 18F in 300 mg of 18O water is added a 1 mL solution consisting of 10 mg of Kryptofix, 1 mg potassium carbonate, 0.005 mL water and 0.95 mL acetonitrile. The vial is heated to remove all the solvents and dry acetonitrile (1 mL) is added again to the vial, which is removed once more under vacuum. Tributyl-[2-(2,2-dimethyl-2H-chromen-6-yl)-3-(3,4,5-trimethoxy-phenyl)-propenyl]-stannane (5 mg) in acetonitrile is then added to the vial. The vial is sealed and heated for 30 minutes to 100° C. The mixture is diluted with dichloromethane and passed through a Sep-Pak and eluted with THF. The filtrate is concentrated to obtain 6-[2-[18F]fluoro-1-(3,4,5-trimethoxy-benyl)-vinyl]-2,2-dimethyl-2H-chromene.

EXAMPLE 11

11a. 4-hydroxy-2,2-dimethyl-chroman-6-carboxylic acid

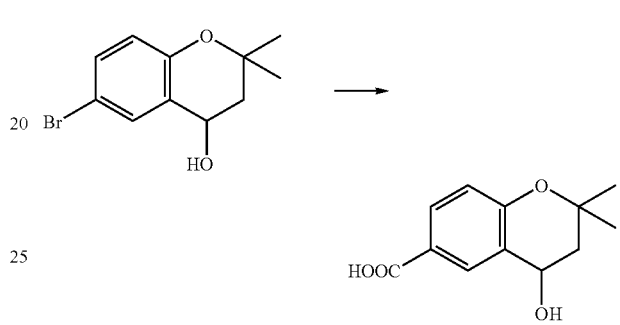

A solution of 6-bromo-2,2-dimethyl-chromanol-4-ol (2.42 g, 10 mmol, Buckle, D. R. et al, J. Med. Chem. 1990, 33, 3028) in anhydrous THF (50 mL) is cooled to −78° C. n-BuLi (2.5 M in hexane, 9.0 mL, 22.6 mmol) is added dropwise to the stirring reaction mixture. The reaction mixture continues to stir at −78° C. for an additional 15 minutes. Gaseous carbon dioxide is bubbled through the reaction mixture, and the temperature is allowed to rise to 25° C. After 12 hours, volatiles are removed by evaporation under reduced pressure, and the crude material is taken up in water. The aqueous layer is acidified with 1 N HCl and extracted with diethyl ether. Combined organic layers are washed with water, brine, dried over sodium sulfate, filtered, and concentrated. The crude product is used in the next step without purification.

11b. 4-hydroxy-2,2-dimethyl-chroman-6-carboxylic Acid 3,4,5-trimethoxy-benzyl ester

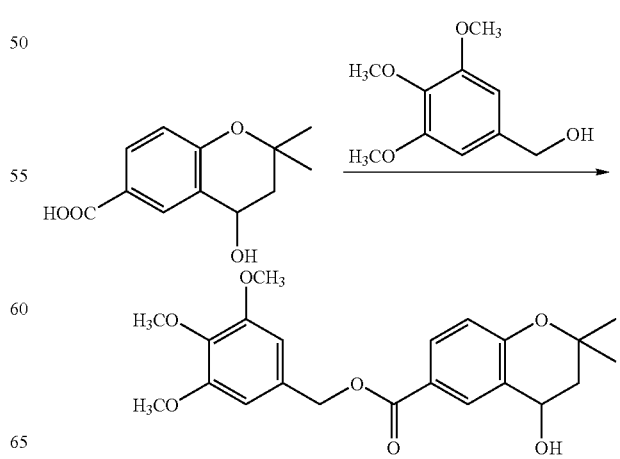

(3,4,5-Trimethoxy phenyl) methanol (1.98 g, 10 mmol) and dimethylaminopyridine (1.47 g, 12 mmol) are dissolved in anhydrous dichloromethane (50 mL). The solution is cooled to 0° C. 1-(3-dimethylaminopropyl)-3-ethylcarbodiimide (4.31 g, 15 mmol) dissolved in dichloromethane (50 mL) is added dropwise. The reaction mixture continues to stir at 0° C. for an additional 2 hours and is then allowed to come to room temperature. After 12 hours the reaction mixture is quenched with saturated $NH_4Cl$. The aqueous layer is extracted with dichloromethane. Combined organic layers are washed with water, brine, dried over sodium sulfate, filtered, and concentrated. Crude 4-hydroxy-2,2-dimethyl-chroman-6-carboxylic acid 3,4,5-trimethoxy benzyl ester is purified using silica gel chromatography.

11c. 2,2-dimethyl-4-(toluene-4-sulfonyloxy)-chroan-6-carboxylic acid 3,4,5-trimethoxy-benzyl ester

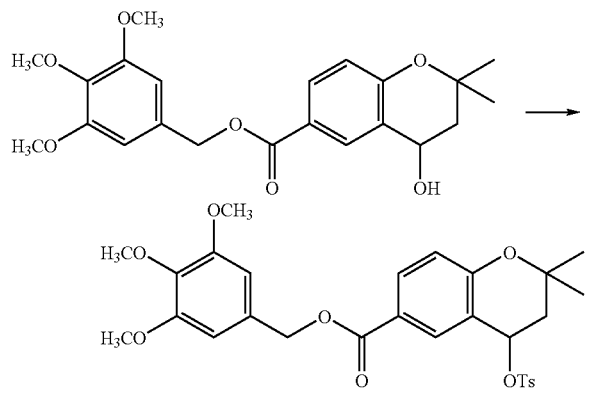

To a stirring solution of 4-hydroxy-2,2-dimethyl-chroman-6-carboxylic acid 3,4,5-trimethoxy benzyl ester (29.4 mg, 0.073 mmol) in dichloromethane (1.5 mL) is added TsCl (15.3 mg, 0.080 mmol) and pyridine (6.47 uL, 0.080 mmol). The reaction mixture continues to stir at room temperature. The crude material is purified using silica gel chromatography to yield 2,2-dimethyl-4-(toluene-4-sulfonyloxy)-chroan-6-carboxylic acid 3,4,5-trimethoxy-benzyl ester.

11d.
4-[18F]Fluoro-2,2-dimethyl-chroman-6-carboxylic Acid 3,4,5-trimethoxy-benzyl ester

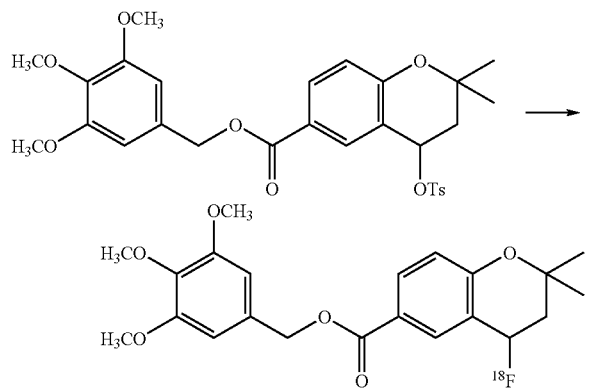

A thin-wall 10 mL, silanized vacutainer with a silanized stopper is charged with tetrabutyl ammonium hydroxide (5 uL, 40% w/v solution in water), and a solution of 18F— in water (10 mCi, 200 uL). The resultant mixture is evaporated to dryness under a flow of nitrogen at 100° C. The residue is further dried by repeated addition and evaporation of acetonitrile (3×200 uL). An additional aliquot of acetonitrile is added and concentrated under vacuum without heating. Prior to complete solvent removal, THF (150 uL) is added, the vial is uncrimped and 2,2-dimethyl-4-(toluene-4-sulfonyloxy)-chroman-6-carboxylic acid 3,4,5-trimethoxy-benzyl ester (2 mg) is added in one portion. The vial is recapped and heated at 65° C. for 30 minutes. After cooling, the vial is diluted with water (4 mL) and passed through a silica gel cartridge (pre-loaded Waters Light C-18 Sep-Pak) to load the sample. The cartridge is rinsed with water and eluted with acetonitrile (2 mL). The acetonitrile is evaporated and the residue is purified via HPLC to afford the desired product.

EXAMPLE 12

Synthesis of 8-[18F]fluoro-2,2-dimethyl-2H-chromene-6-carboxylic acid 3,4,5-trimetoxy-benzyl ester

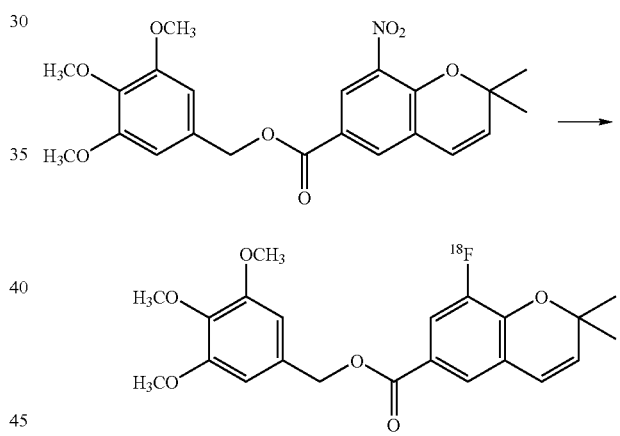

A thin-wall 10 mL, silanized vacutainer with a silanized stopper is charged with tetrabutyl ammonium hydroxide (5 uL, 40% w/v solution in water), and a solution of 18F— in water (10 mCi, 200 uL). The resultant mixture is evaporated to dryness under a flow of nitrogen at 100 degrees C. The residue is dried further by repeated addition and evaporation of acetonitrile (3×200 uL). An additional aliquot of acetonitrile is added and concentrated under vacuum without heating. Prior to complete solvent removal, THF (150 uL) is added, the vial is uncrimped and 2,2-dimethl-8-nitro-2H-chromene-6-carboxylic acid 3,4,5-trimethoxy-benzyl ester, previously prepared by Chemistry and Biology 2000, 7, 979,(2 mg) is added in one portion. The vial is recapped and heated at 65° C. for 30 minutes. After cooling to room temperature, the vial is diluted with water (4 mL) and passed through a silica gel cartridge (pre-loaded Waters Light C-18 Sep-Pak) to load the sample. The cartridge is rinsed with water and eluted with acetonitrile (2 mL). The acetonitrile is evaporated and the residue is purified via HPLC to afford the desired product.

EXAMPLE 13

13a. (4-Hydroxy-phenylsulfanyl)-(3,4,5-trimethoxy-phenyl)-acetic acid ethyl ester

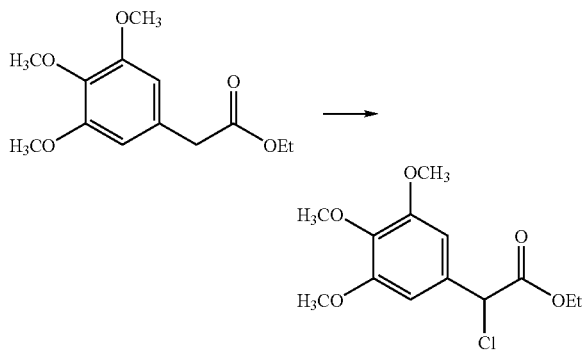

Trimethylsilyl chloride (4.52 g, 14 mmol) and (3,4,5-trimethoxy-phenyl)-acetic acid ethyl ester (2.03 g, 8 mmol) in THF (25 mL) are added successively to a solution of lithium diisopropylamide (prepared from diisopropyl amine (8.8 mmol) and n-Butyl lithium (1.6 N in hexane, 5.5 mL) in THF (25 mL) at −78° C. The mixture is stirred at −78° C. for 1 h. N-chlorosuccinimide (1.12 g, 8.4 mmol) is added in one portion to the stirred solution. The reaction mixture is allowed to warm up to 0° C. over 3 hours, stirring at 0° C. for 30 minutes and then diluted with water. The aqueous layer is extracted with dichloromethane. Combined organic layers are washed with water, brine, dried over sodium sulfate, filtered, and concentrated. The crude product is purified using silica gel chromatography.

13b. 4-Hydroxy-phenylsulfanyl)-(3,4,5-trimethoxy-phenyl)-acetic acid ethyl ester

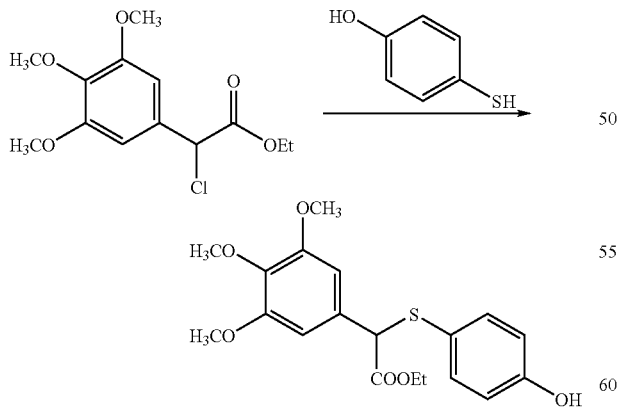

To a solution of 4-mercapto-phenol (1.26 g, 10 mmol), K₂CO₃ (4.14 g, 30 mmol) and tetra butyl ammonium iodide (0.74 g, 2 mmol) dissolved in DMF (20 mL) is added dropwise 4-chloro-(3,4,5-trimethoxy-phenyl)-acetic acid ethyl ester (2.88 g, 10 mmol) in DMF (10 mL). The reaction mixture continues to stir at room temperature. After 12 hours the reaction mixture is quenched with 3% HCl (aqueous). The aqueous layer is extracted with ethyl acetate. Combined organic layers are washed with water, brine, dried over sodium sulfate, filtered, and concentrated. The crude product is purified using silica gel chromatography.

13c. 4-[2-Hydroxy-1-(3,4,5-trimethoxy-phenyl)-ethylsulfanyl]-phenol

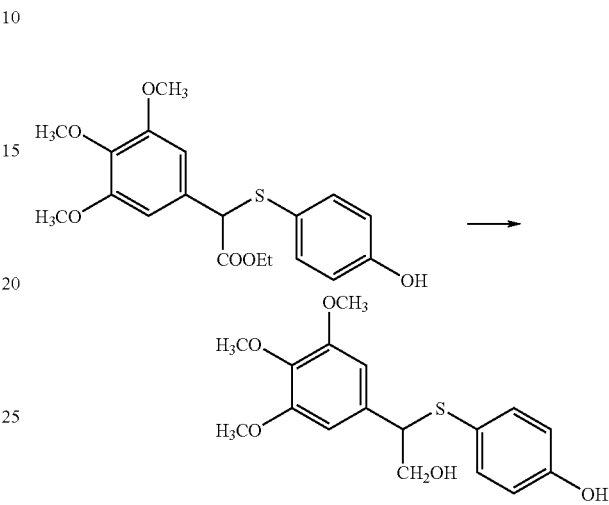

4-Hydroxy-phenylsulfanyl)-(3,4,5-trimethoxy-phenyl)-acetic acid ethyl ester (4.8 g, 12.7 mmol) dissolved in THF (30 mL) is added rapidly to a cooled (0° C.) solution of lithium aluminum hydride (3.15 g, 12.7 mmol) in THF (32.7 mL). The reaction mixture is stirred at room temperature. After 1.5 hours the reaction mixture is quenched with 2.5 N HCl and diluted with water. The aqueous layer is extracted with ethyl acetate. Combined organic layers are washed with water, brine, dried over sodium sulfate, filtered, and concentrated. The crude product is purified using silica gel chromatography.

13d. 2-[4-(1,1-dimethyl-prop-2-ynyloxy-phenylsulfanyl]-2-(3, 4, 5-trimethoxy-phenyl)-ethanol

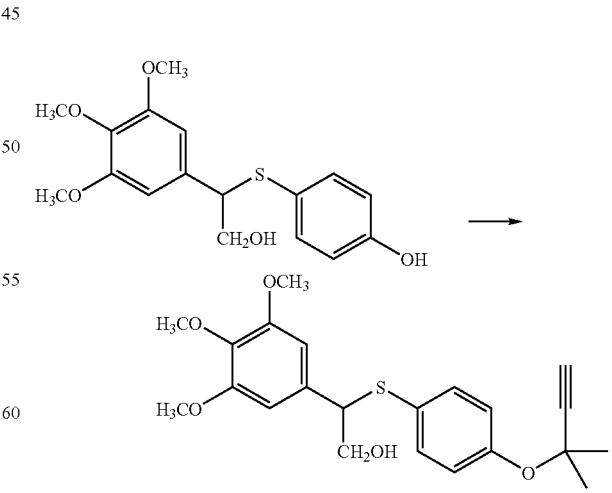

3-Chloro-3-methyl-1-butyne (1.72 g, 16.8 mmol) is added to a mixture of 4-[2-hydroxy-1-(3,4,5-trimethoxy-phenyl)-ethylsulfanyl]-phenol (2.83 g, 8.41 mmol), potassium carbonate (2.35 g, 16.82 mmol), potassium iodide (2.37 g, 14.23 mmol), and copper iodide (33 mg, 0.17 mmol) in dry DMF (10 mL). The reaction mixture is then heated to 70° C. After 4 hours, the reaction is cooled down to room temperature and concentrated under reduced pressure. The residue is redissolved in dichloromethane and washed with water, brine, and dried over sodium sulfate, filtered, and concentrated. The crude product is purified using silica gel chromatography 13e. 2-(2,2-Dimethyl-2H-chromen-6-ylsulfanyl)-2-(3, 4, 5-trimethoxy-phenyl)-ethanol

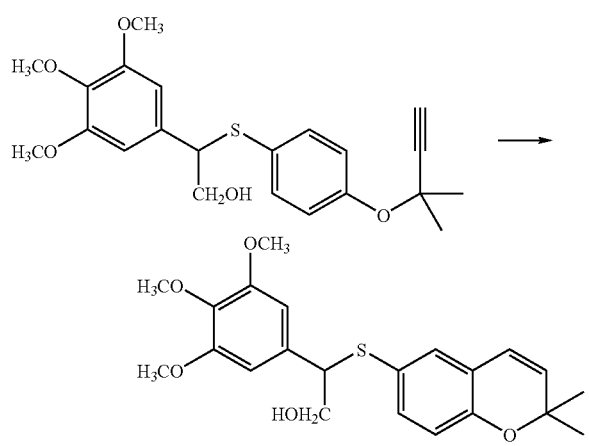

N,N-diethyl aniline (9.53 mL) is heated to 185° C. 2-[4-(1,1-Dimethyl-prop-2-ynyloxy-phenylsulfanyl]-2-(3,4,5-trimethoxy-phenyl)-ethanol (16.11 g, 0.04 mol) is added dropwise. The reaction mixture is then heated to 195° C. After 1 hour the reaction mixture is cooled down to room temperature and is diluted with hexanes. The organic layer is extracted with 5% HCl, dried over sodium sulfate, filtered, and concentrated to yield the desired product which is used in the next step without further purification.

13f. Toluene-4-sulfonic acid 2-(2,2-dimethyl-2H-chromen-6-ylsulfanyl)-2-(3,4,5-trimethoxy-phenyl)-ethyl ester

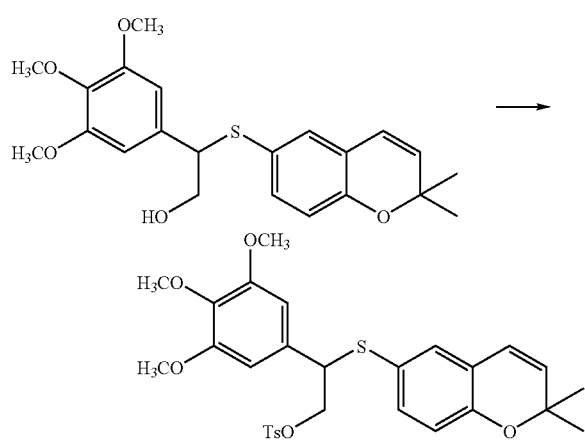

To a stirring solution of 2-(2,2-dimethyl-2H-chromen-6-ylsulfanyl)-2-(3,4,5-trimethoxy-phenyl)-ethanol (29.3 mg, 0.073 mmol) in dichloromethane (1.5 mL) is added p-toluenesulfonylchloride (15.3 mg, 0.080 mmol) and pyridine (6.47 uL, 0.080 mmol). The reaction mixture continues to stir at room temperature. The crude material is purified using silica gel chromatography to yield the desired product.

13g. 6-[2-[18F]fluoro-1-(3, 4, 5-trimethoxy-phenyl)-ethylsulfanyl]-2,2-dimethyl-2H-chromene

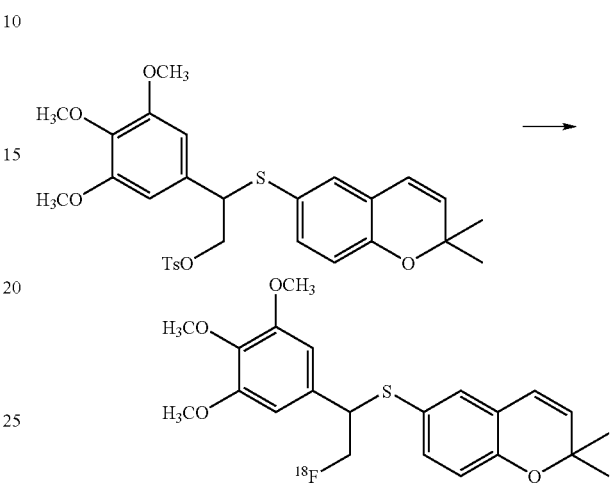

A thin-wall 10 mL, silanized vacutainer with a silanized stopper is charged with tetrabutyl ammonium hydroxide (5 uL, 40% w/v solution in water), and a solution of 18F— in water (10 mCi, 200 uL) is added. The resultant mixture is evaporated to dryness under a flow of nitrogen at 100° C. The residue is further dried by repeated addition and evaporation of acetonitrile (3×200 uL). An additional aliquot of acetonitrile is added and concentrated under vacuum without heating. Prior to complete solvent removal, THF (150 uL) is added, the vial is uncrimped and 2-(2,2-dimethyl-2H-chromen-6-ylsulfanyl)-2-(3,4,5-trimethoxy-phenyl)-ethyl ester (2 mg) is added in one portion. The vial is recapped and heated at 65° C. for 30 minutes. After cooling, the vial is diluted with water (4 mL) and passed through a silica gel cartridge (pre-loaded Waters Light C-18 Sep-Pak) to load the sample. The cartridge is rinsed with water and eluted with acetonitrile (2 mL). The acetonitrile is evaporated and the residue is purified via HPLC to afford the desired product.

EXAMPLE 14

EXAMPLE 14a

Synthesis of 4-(4-hydroxy-but-1-ynyl)-benzoic acid methyl ester

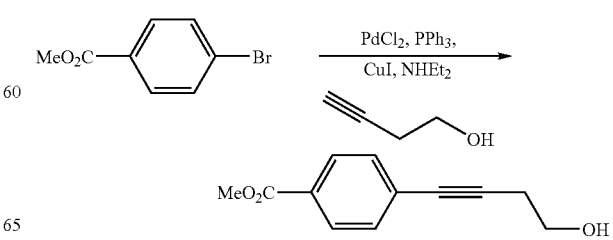

To a stirring solution of methyl 4-bromobenzoate (13.4 g, 0.62 mmol) in diethyl amine (200 mL) was added palladium chloride (0.55 g, 3.06 mmol), and triphenylphosphine (0.16 g, 0.62 mmol). The solution was degassed and copper iodide (0.12 g, 0.62 mmol) and 3-butyn-1-ol (4.34 g, 62 mmol) were added. The reaction mixture continued to stir at room temperature overnight. Over the next two days, an additional 0.5 mol % palladium chloride, 1.0 mol % triphenylphosphine, and 12 mol % 3-butyn-1-ol were added. Once the reaction was complete according to LCMS, the reaction mixture was concentrated and the crude material was taken up in a slurry of silica gel and ethyl acetate. The organic solvent was removed and the remaining dried silica gel was packed in a fritted funnel. Extensive washes with a hexane:ethyl acetate mixture (1:4) followed by ethyl acetate (100%) washes yielded the desired 4-(4-hydroxy-but-1-ynyl)-benzoic acid methyl ester (11.9 g, 0.58 mmol) as the desired product (94% yield). $^1$H (CDCl$_3$, 600 MHz): δ 7.95 (2H, d, J=8.4 Hz), 7.45 (2H, d, J=8.4 Hz), 3.9 (s, 3H), 3.83 (2H, t, J=6.6 Hz), 2.71 (2H, t, J=6.0 Hz).

EXAMPLE 14b

Synthesis of 4-(4-hydroxy-butyl)-benzoic acid methyl ester

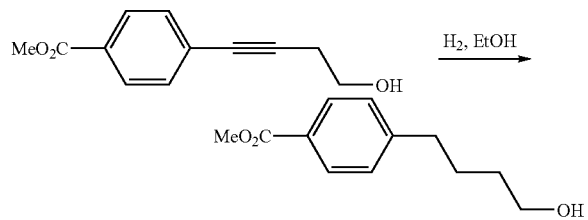

To a stirring solution of 4-(4-hydroxy-but-1-ynyl)-benzoic acid methyl ester (6.29 g, 0.031 mol) in ethanol (60 mL) was added palladium on carbon (5 g, 10% on carbon) and the reaction mixture was hydrogenated at 50 psi. After 20 hours, the reaction mixture was filtered to remove the catalyst and the filtrate was concentrated to afford 4-(4-hydroxy-butyl)-benzoic acid methyl ester (5.67 g, 0.027 mol) as the desired product (89% yield). $^1$H (CDCl$_3$, 600 MHz): δ 7.94 (2H, d, J=8.4 Hz), 7.24 (2H, d, J=8.4 Hz), 3.89 (s, 3H), 3.65 (2H, t, J=6.6 Hz), 2.65 (2H, t, J=7.8 Hz), 1.71 (2H, m), 1.58 (2H, m).

EXAMPLE 14c

Synthesis of 4-(4-hydroxymethyl-phenyl)-butan-1-ol

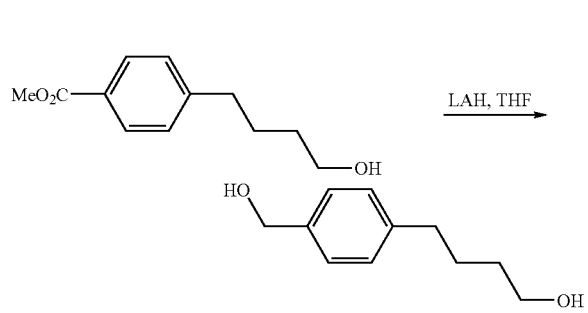

To a stirring solution of 4-(4-hydroxy-butyl)-benzoic acid methyl ester (2.24 g, 0.01 mol) in THF (100 mL) was added dropwise a solution of lithium aluminum hydride (8.0 mL, 1M in THF). After completion of addition the reaction mixture continued to stir at room temperature. After 6 hours, the reaction mixture was quenched with water. The aqueous layer was extracted with ethyl acetate. All combined organic layers were dried over Na$_2$SO$_4$, filtered, and concentrated to yield 4-(4-hydroxymethyl-phenyl)-butan-1-ol as a yellow oil (1.90 g, 0.01 mol, 98% yield). $^1$H (CDCl$_3$, 600 MHz): δ 7.29 (2H, d, J=8.1 Hz), 7.16 (2H, d, J=8.1 Hz), 4.60 (2H, s), 3.60 (2H, t, J=7.5 Hz), 2.62 (2H, t, J=7.5 Hz), 1.67 (2H, m), 1.56 (2H, m); $^{13}$C (CDCl$_3$, 150 MHz): δ 141.7, 138.5, 128.5, 127.0, 65.0, 62.5, 35.2, 32.1, 27.5.

EXAMPLE 14d

Synthesis of 4-[4-(tert-butyl-dimethyl-silanyloxy)-butyl]-benzoic acid methyl ester

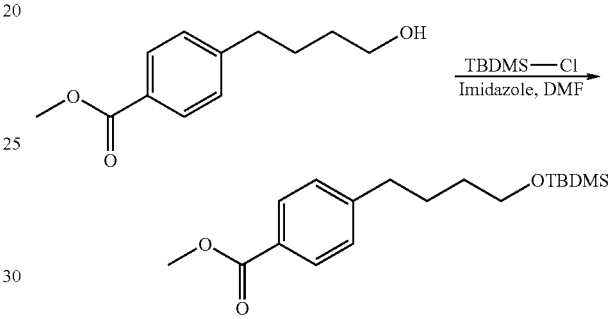

To a solution of 4-(4-hydroxy-butyl)-benzoic acid methyl ester (300 mg, 1.44 mmol) in DMF (4 mL) was added imidazole (147 mg, 2.16 mmol) followed by TBDMS-Cl (324 mg, 2.16 mmol). The reaction stirred at room temperature for 2 hours, monitoring by TLC (3:1 Hexane:ethyl acetate). After consumption of the starting material, the reaction was diluted with ethyl acetate and washed with water (3×) and saturated sodium bicarbonate (1×). The organic layer was dried over sodium sulfate, filtered, and concentrated down to obtain a yellow oil (360 mg, 77% yield). This crude oil was taken on to the next step without further purification.

EXAMPLE 14d

Synthesis of {4-[4-(tert-butyl-dimethyl-silanyloxy)-butyl]-phenyl}-methanol

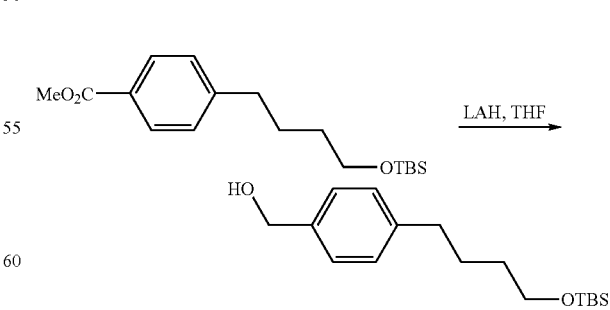

To a stirring cooled (0° C.) solution of 4-[4-(tert-butyl-dimethyl-silanyloxy)-butyl]-benzoic acid methyl ester (0.80 g, 2.48 mol) in THF (5.5 mL) was added dropwise a solution of lithium aluminum hydride (4.96 mL, 1M in THF). After

EXAMPLE 14e

Synthesis of 2-[4-(4-hydroxy-butyl)-benzylsulfanyl]-3-methyl-chromen-4-one

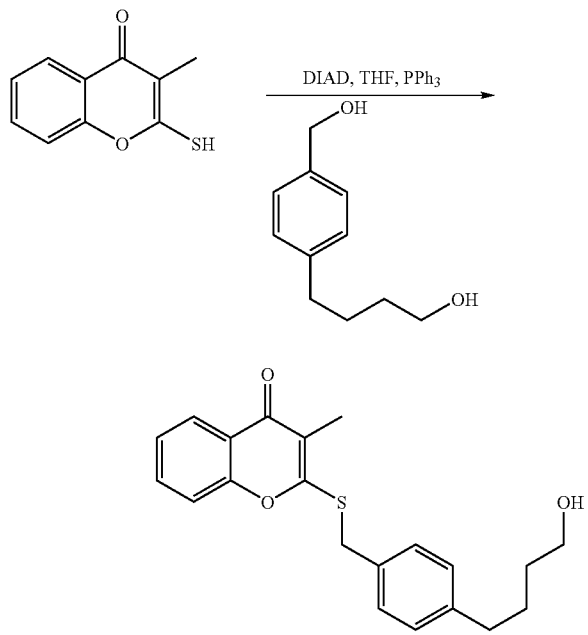

To solution of 2-mercapto-chromen-4-one (1.52 g, 7.90 mmol) and 4-(4-hydroxymethyl-phenyl)-butan-1-ol (1.90 g, 9.90 mmol) dissolved in anhydrous THF (80 mL) was added solid PPh₃ (3.11 g, 11.90 mmol) and DIAD (2.30 mL, 11.90 mmol). After completion of addition the reaction mixture continued to stir at room temperature. After 20 hours, the reaction mixture was diluted with water. The aqueous layer was separated and extracted with ethyl acetate (3×). All combined organic layers were dried over Na₂SO₄, filtered, and concentrated to yield an oil. The crude material was purified using silica gel chromatography (1:1 pentane: ethyl acetate) to yield 2-[4-(4-hydroxy-butyl)-benzylsulfanyl]-3-methyl-chromen-4-one (1.29 g, 3.64 mmol) in moderate yield (46%). $^1$H (CDCl$_3$, 600 MHz): δ 8.18 (1H, dd, J=7.9, 1.3 Hz), 7.60 (1H, ddd, J=8.6, 7.2, 1.7 Hz), 7.31 (2H, t, J=8.5 Hz), 7.29 (2H, d, J=8.1 Hz), 7.12 (2H, d, J=8.1 Hz), 4.36 (2H, s), 3.62 (2H, m), 2.61 (2H, t, J=7.5 Hz), 2.00 (3H, s), 1.67 (2H, m), 1.56 (2H, m); $^{13}$C (CDCl$_3$, 150 MHz): δ 174.9, 161.3, 156.0, 141.5, 133.2, 132.3, 128.3, 128.2, 125.7, 124.5, 122.2, 117.2, 116.3, 62.3, 34.7, 31.8, 29.2, 26.9, 10.1.; HRMS calcd for C21H22O3S 355.1363:, found 355.1364

EXAMPLE 14f

Synthesis of Toluene-4-sulfonic acid 4-[4-(3-methyl-4-oxo-4H-chromen-2-ylsulfanylmethyl)-phenyl]-butyl ester

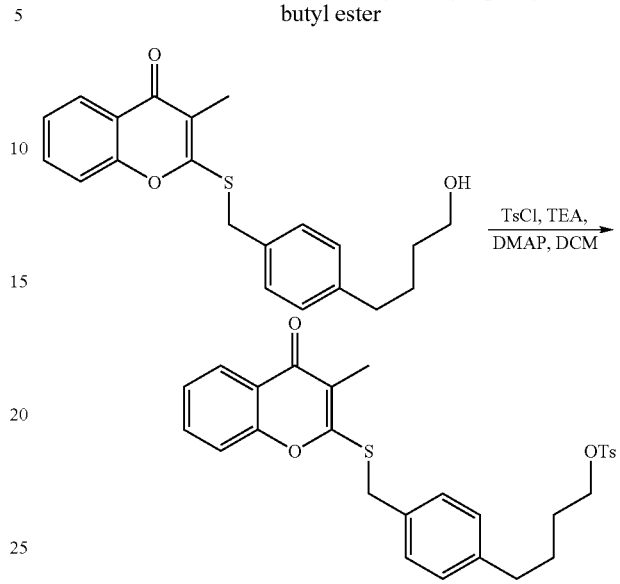

To a solution 2-[4-(4-hydroxy-butyl)-benzylsulfanyl]-3-methyl-chromen-4-one (300 mg, 0.85 mmol) dissolved in anhydrous dichloromethane (8.0 mL) was added TsCl (194 mg, 1.01 mmol), DMAP (124 mg, 1.01 mmol) and TEA (0.213 mL, 1.52 mmol). The reaction mixture continued stirring at room temperature. After 3 hours the reaction mixture was diluted with water. The aqueous layer was separated and extracted with ethyl acetate (3×). All combined organic layers were dried over Na₂SO₄, filtered, and concentrated to yield an oil. The crude material was purified using silica gel chromatography (1:1 pentane: ethyl acetate) to yield toluene-4-sulfonic acid 4-[4-(3-methyl-4-oxo-4H-chromen-2-ylsulfanylmethyl)-phenyl]-butyl ester (280 mg, 0.55 mmol) in moderate yield (65%). $^1$H (CDCl$_3$, 600 MHz): δ 8.18 (1H, dd, J=7.9, 1.3 Hz), 7.77 (2H, d, J=8.2 Hz). 7.62 (1H, m), 7.39 (2H, t, J=8.0 Hz), 7.33 (2H, d, J=8.0 Hz), 7.30 (2H, d, J=8.0 Hz), 7.07 (2H, d, J=8.0 Hz), 4.37 (2H, s), 4.02 (2H, t, J=5.8 Hz), 2.55 (2H, t, J=7.3 Hz), 2.05 (3H, s), 1.65 (4H, m); $^{13}$C (CDCl$_3$, 150 MHz): δ 175.5, 162.2, 156.7, 144.9, 141.5, 134.1, 133.4, 133.0, 130.0, 129.1, 129.0, 128.1, 126.5 125.3, 122.9, 117.5, 117.0, 70.5, 35.3, 34.9, 28.6, 27.2, 21.8, 10.8.; HRMS calcd for C28H28O5S2 509.1450:, found 509.1441

EXAMPLE 14g

Synthesis of 2-[4-(4-fluoro-butyl)-benzylsulfanyl]-3-methyl-chromen-4-one

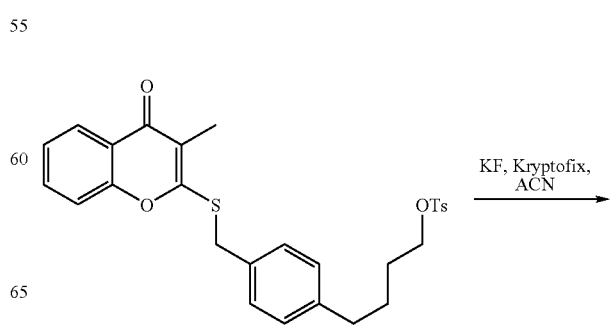

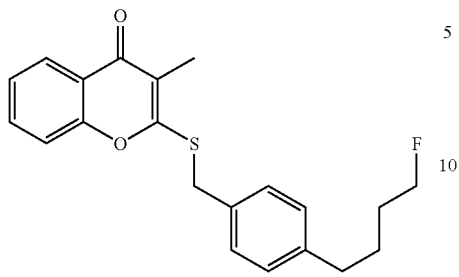

To a solution of toluene-4-sulfonic acid 4-[4-(3-methyl-4-oxo-4H-chromen-2-ylsulfanylmethyl)-phenyl]-butyl ester (10 mg, 0.020 mmol) in anhydrous acetontirile (0.2 mL) was added KF (2.28 mg, 0.04 mmol) and Kryptofix (14.8 mg, 0.04 mmol). After completion of addition the reaction mixture was heated to 90° C. After 25 minutes, the reaction mixture was cooled down to room temperature and diluted with water. The aqueous layer was separated and extracted with ethyl acetate (3×). All combined organic layers were dried over $Na_2SO_4$, filtered, and concentrated to yield an oil. The crude material was purified using reverse phase chromatography (Luna, 10u, C18, 250×21.2 mm 10 micro, 20% of water in 90% Acetonitrile in water with 0.1% TFA as the modifier in both mobile phases) to yield 2-[4-(4-fluoro-butyl)-benzylsulfanyl]-3-methyl-chromen-4-one (3.3 mg, 0.01 mmol) in moderate yield (46%). $^{19}F$ (CDCl$_3$, 564 MHz): 6-218.67(1F, m). $^1H$ (CDCl$_3$, 600 MHz): δ 8.18 (1H, dd, J=7.8, 1.8 Hz), 7.60 (1H, m), 7.36 (2H, m), 7.31 (2H, d, J=7.8 Hz), 7.13 (2H, d, J=8.0 Hz), 4.47 (1H, m), 4.39 (1H, m), 4.36 (2H, s), 2.63 (2H, t, J=6.6 Hz), 2.03 (3H, s), 1.69 (4H, m); $^{13}C$ (CDCl$_3$, 150 MHz): δ 175.3, 162.0, 156.5, 141.7, 133.8, 132.7, 128.8, 126.2 125.2, 122.6, 117.3, 116.8, 84.4 (83.3), 35.1, 35.0, 29.9 (29.8), 26.9, 10.5.

EXAMPLE 15

Synthesis of 2-{4-[4-(tert-butyl-dimethyl-silanyloxy)-butyl]-phenyloxy}-3-methyl-chromen-4-one

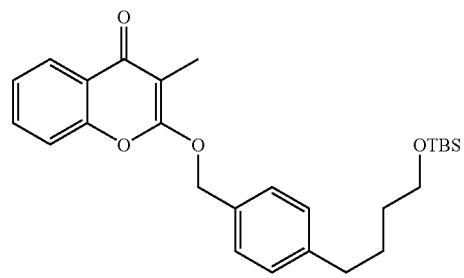

Solid NaH (37 mg, 1.5 mmol) was placed in a reaction flask and cooled to 0° C. in an ice bath. A solution of 4-[4-(tert-butyl-dimethyl-silanyloxy)-butyl]-phenyl}-methanol (377 mg, 1.28 mmol) in dry DMF (23 mL) was added to the reaction flask dropwise while stirring. After completion of addition the reaction mixture continued to stir at 0° C. for an additional hour. A solution of 2-methanesulfonylo-3-methyl-chromen-4-one (0.92 g, 3.84 mmol) dissolved in dry DMF (20 mL) was added dropwise to the stirring reaction mixture. After completion of addition the reaction mixture continued to stir at room temperature. Once the reaction was complete as judged by TLC the reaction mixture was cooled to 0° C. and quenched with water. The aqueous layer was separated and extracted with ethyl acetate (3×). All combined organic layers were dried over $Na_2SO_4$, filtered, and concentrated to yield an oil. The crude material was purified using silica gel chromatography (1:1 hexanes:ethyl acetate) to yield 2-{4-[4-(tert-butyl-dimethyl-silanyloxy)-butyl]-phenyloxy}-3-methyl-chromen-4-one (258 mg, 0.73 mg, 49%). HRMS calcd for C27H36O4Si: 453.2455, found 453.2457.

EXAMPLE 15b

Synthesis of 2-[4-(4-hydroxy-butyl)-benzyloxy]-3-methyl-chromen-4-one

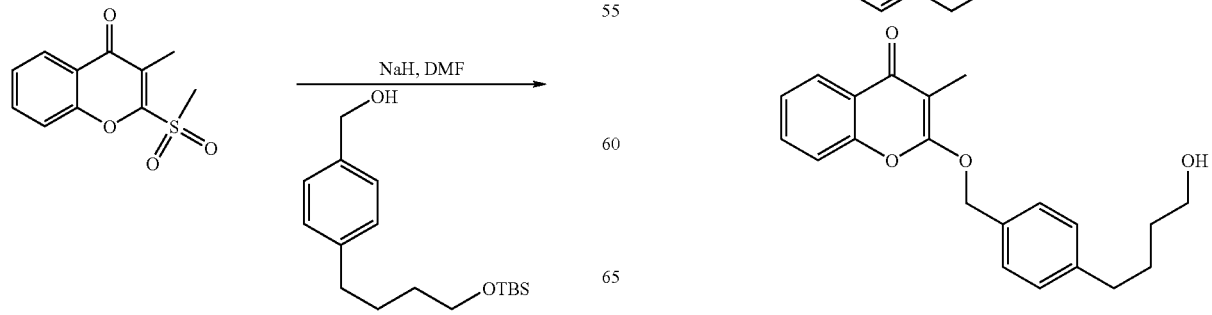

To a solution of 2-{4-[4-(tert-butyl-dimethyl-silanyloxy)-butyl]-phenyloxy}-3-methyl-chromen-4-one (258 mg, 0.57 mmol) dissolved in anhydrous THF (5 mL) was added a solution of TBAF (1.0 M solution in THF, 1.15 mL, 1.15 mmol) dropwise. After completion of addition the reaction was stirred a room temperature for 1 h and then quenched with water. The aqueous layer was separated and extracted with ethyl acetate (3×). All combined organic layers were dried over Na$_2$SO$_4$, filtered, and concentrated to yield an oil. The crude material was purified using silica gel chromatography (1:2 hexanes:ethyl acetate) to yield 2-[4-(4-hydroxy-butyl)-benzyloxy]-3-methyl-chromen-4-one (101 mg, 0.30 mmol) in moderate yield (52%).

HRMS calcd for C21H22O4 339.1590:, found 339.1591.

EXAMPLE 15c

Synthesis of toluene-4-sulfonic acid 4-[4-(3-methyl-4-oxo-4H-chromen-2-yloxymethyl)-phenyl]-butyl ester

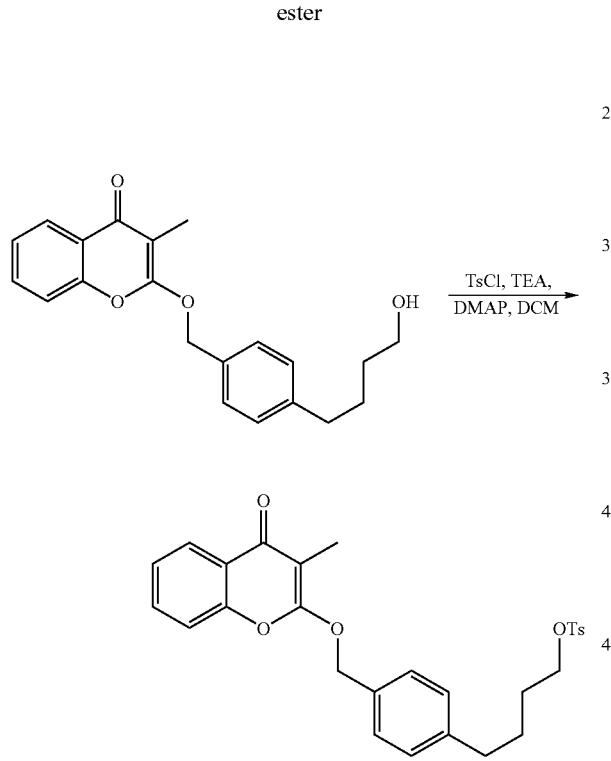

a solution 2-[4-(4-hydroxy-butyl)-benzyloxy]-3-methyl-chromen-4-one (101 mg, 0.30 mmol) dissolved in anhydrous dichloromethane (3.0 mL) was added TsCl (68 mg, 0.36 mmol), DMAP (55 mg, 0.45 mmol) and TEA (0.050 mL, 0.36 mmol). The reaction mixture continued stirring at room temperature. After 20 h, the reaction mixture was diluted with water. The aqueous layer was separated and extracted with ethyl acetate (3×). All combined organic layers were dried over Na$_2$SO$_4$, filtered, and concentrated to yield an oil. The crude material was purified using silica gel chromatography (4:1 pentane: ethyl acetate) to yield toluene-4-sulfonic acid 4-[4-(3-methyl-4-oxo-4H-chromen-2-yloxymethyl)-phenyl]-butyl ester (75.2 mg, 0.15 mmol) in moderate yield (51%). $^1$H (CDCl$_3$, 600 MHz): δ 8.21 (1H, dd, J=8.2, 1.5 Hz), 7.77 (2H, d, J=8.3 Hz). 7.60 (1H, m), 7.33 (2H, d, J=8.0 Hz), 7.36 (2H, d, J=8.0 Hz), 7.39 (2H, d, J=8.2 Hz), 7.33 (2H, d, J=8.0 Hz), 7.99 (2H, d, J=7.9 Hz), 5.43 (2H, s), 4.04 (2H, t, J=5.9 Hz), 2.59 (2H, t, J=7.3 Hz), 2.44 (3H, s), 1.99 (3H, s), 1.68 (4H, m);); $^{13}$C (CDCl$_3$, 150 MHz): δ 178.2, 161.8, 152.2, 144.2, 141.9, 132.7, 132.2, 131.9, 129.3, 128.3, 127.7, 127.4, 125.6, 127.7, 122.1, 116.1, 70.1, 69.8,34.3, 27.9,26.5, 21.1, 6.7. HRMS calcd for C28H28O6S: 545.1498, found. 515.1493.

EXAMPLE 15d

Synthesis of 2-[4-(4-fluoro-butyl)-benzyloxy]-3-methyl-chromen-4-one

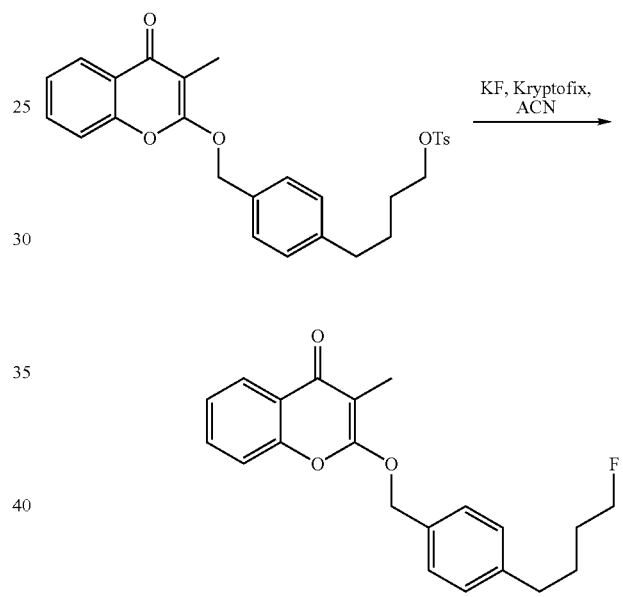

To a solution of toluene-4-sulfonic acid 4-[4-(3-methyl-4-oxo-4H-chromen-2-yloxymethyl)-phenyl]-butyl ester (20 mg, 0.04 mmol) in anhydrous acetonitrile (0.5 mL) was added KF (4.72 mg, 0.08 mmol) and Kryptofix (30.6 mg, 0.08 mmol). After completion of addition the reaction mixture was heated to 90° C. After 15 minutes, the reaction mixture was cooled down to room temperature and diluted with water. The aqueous layer was separated and extracted with ethyl acetate (3×). All combined organic layers were dried over Na$_2$SO$_4$, filtered, and concentrated to yield an oil. The crude material was purified using reverse phase chromatography (Luna, 10u, C18, 250×21.2 mm 10 micro, 30% of water in 90% Acetonitrile in water with 0.1% TFA as the modifier in both mobile phases) to yield 2-[4-(4-fluoro-butyl)-benzyloxy]-3-methyl-chromen-4-one (6.8 mg, 0.02 mmol) in low yield (13.6%).$^{19}$F (CDC13, 564 MHz): δ −218.72 (1F, m). HRMS calcd for C21H21FO3: 341.1547, found 341.1547.

$^1$H (CDCl$_3$, 600 MHz): δ 8.21 (1H, dd, J=8.3, 1.6 Hz), 7.60 (1H, m), 7.39 (2H, m), 7.22 (2H, d, J=8.0 Hz), 7.13 (2H, d,

J=8.0 Hz), 5.44 (2H, s), 4.50 (1H, m), 4.41 (1H, m), 2.68 (2H, t, J=7.1 Hz), 1.99 (3H, s), 1.75 (4H, m).

EXAMPLE 16

EXAMPLE 16a

Synthesis of 2-(4 Iodo-benzyl)-isoindole-1,3-dione

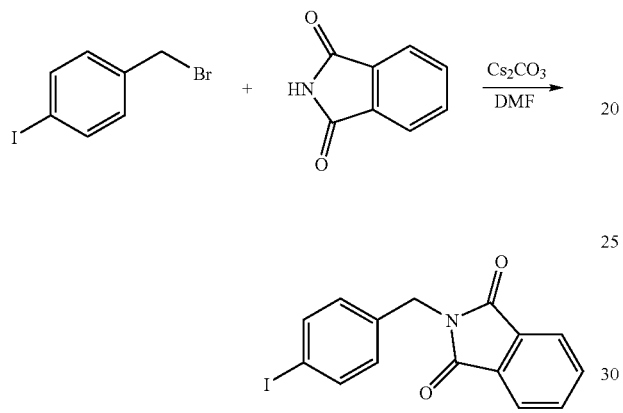

To a solution of 4-iodo-benzyl bromide (9.04 g, 30.4 mmol) in DMF (316 mL) was added phthalimide (4.47 g, 30.4 mmol) and cesium carbonate (14.86 g, 45.6 mmol). The reaction stirred at room temperature overnight under nitrogen atmosphere. The next day, the reaction mixture was quenched with water. The product precipitated from the quenched reaction mixture and was filtered off, washed with water, and collected as a white solid (9.5 g, 86% yield). $^1$H NMR (600 MHz, CDCl$_3$): δ 7.84 (m, 2H), 7.71 (m, 2H), 7.63 (d, 2H, J=8.4 Hz), 7.17 (d, 2H, J=8.4 Hz), 4.77 (s, 2H). $^{13}$C NMR (150 MHz, CDCl$_3$): δ 168.1, 138.0, 136.2, 134.3, 132.2, 130.8, 123.6, 93.7, 41.3.

EXAMPLE 16b

Synthesis of 2-[4-(4-Hydroxy-but-1-ynyl)-benzyl]-isoindole-1,3-dione

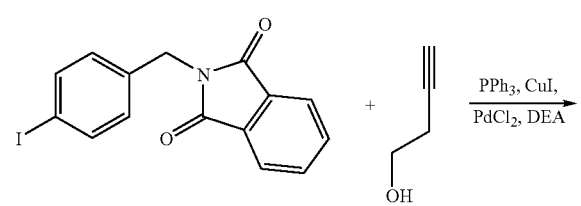

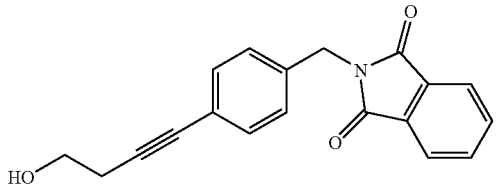

To a slurry of 2-(4 iodo-benzyl)-isoindole-1,3-dione (2.0 g, 5.51 mmol), triphenylphosphine (14.4 mg, 0.055 mmol), and palladium chloride (5 mg, 0.028 mmol) in DEA (20 mL) was added DMF (4 mL) and copper iodide (11 mg, 0.055 mmol) followed by 3-butyn-1-ol (417 µL, 5.51 mmol). The reaction stirred at room temperature overnight under nitrogen atmosphere. The next day, the reaction mixture was concentrated and purified by flash column chromatography (2:1 Hexane: ethyl acetate) to yield the product as a yellow solid (0.76 g, 45% yield). $^1$H NMR (600 MHz, CDCl$_3$): δ 7.86 (m, 2H), 7.76 (m, 2H), 7.36 (s, 4H), 4.83 (s, 2H), 3.80 (q, 2H, J=6.3 Hz), 2.68 (t, 2H, J=6.2 Hz), 1.80 (t, 1H, J=6.4 Hz); $^{13}$C NMR (150 MHz, CDCl$_3$): δ 167.5, 135.5, 133.6, 131.5, 131.4, 128.0, 122.9, 122.5, 86.3, 81.5, 60.6, 40.8, 23.3.

EXAMPLE 16c

Synthesis of 2-[4-(4-Hydroxy-butyl)-benzyl]-isoindole-1,3-dione

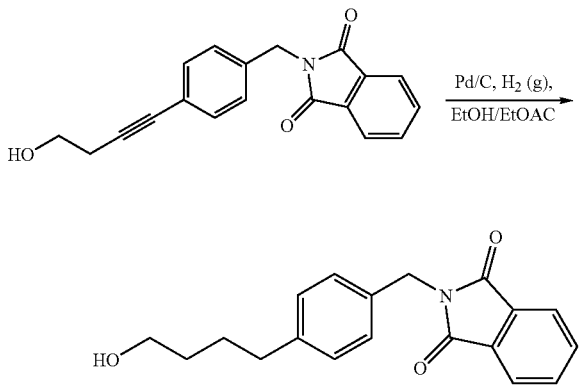

To a solution of 2-[4-(4-hydroxy-but-1-ynyl)-benzyl]-isoindole-1,3-dione (2.0 g, 6.55 mmol) in ethanol/ethyl acetate (3:1, 163 mL) was added palladium on carbon (10 wt. %, 1.04 g). The reaction stirred at room temperature overnight under 50 psi of hydrogen. The reaction was monitored by $^1$H NMR to see conversion to product. Upon completion, the reaction mixture was filtered through diatomaceous earth (Celite®), washed with ethyl acetate, and concentrated to obtain the product as a yellow oil (1.88 g, 93% yield). $^1$H NMR (600 MHz, CDCl$_3$): δ 7.81 (2H, m), 7.67 (m, 2H), 7.33 (d, 2H, J=8.1 Hz), 7.10 (d, 2H, J=8.1 Hz), 4.79 (s, 2H), 3.69 (q, 3H, J=7.0 Hz), 3.60 (t, 2H, J=6.5 Hz), 2.58 (t, 2H, J=7.4 Hz), 1.64 (m, 2H), 1.55 (m, 2H); $^{13}$C NMR (150 MHz, CDCl$_3$): 168.3, 142.2, 134.1, 134.0, 132.3, 128.8, 128.8, 123.5, 62.9, 41.5, 35.4, 32.4, 27.6.

EXAMPLE 16d

Synthesis of 2-[4-(4-Hydroxy-butyl)-benzylamino]-3-methyl-chromen-4-one

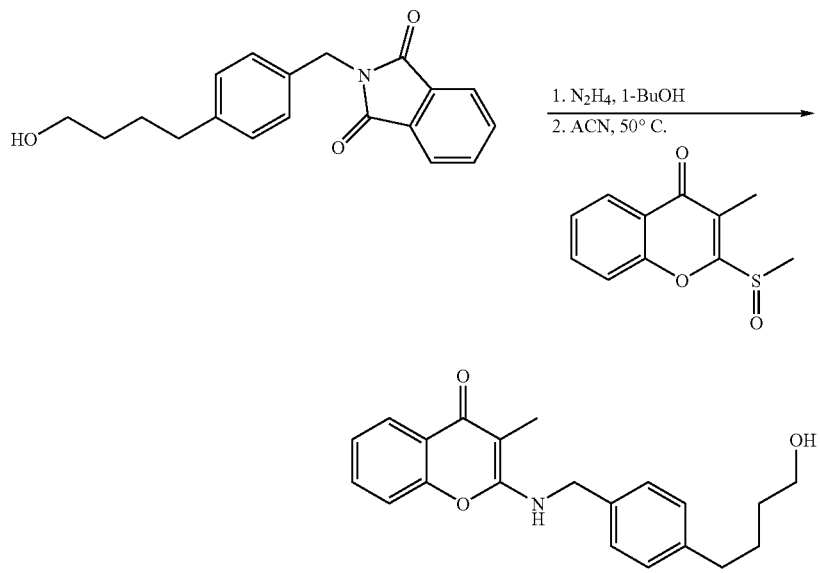

A solution of 2-[4-(4-hydroxy-butyl)-benzyl]-isoindole-1,3-dione (964 mg, 3.12 mmol) and hydrazine (215 μL, 6.86 mmol) in n-butanol (59 mL) was placed under reflux for 1 h. A precipitate formed upon cooling to room temperature, which was filtered off and washed with n-butanol. The filtrate was then concentrated down to obtain the product as a yellow solid, which was used in the next step without any further purification. $^1$H NMR (600 MHz, DMSO-$d_6$): δ=7.22 (d, 2H, J=7.8 Hz), 7.11 (d, 2H, J=7.8 Hz), 3.69 (s, 2H), 3.39 (t, 2H, J=6.6 Hz), 2.54 (t, 2H, J=7.6 Hz), 1.56 (m, 2H), 1.41 (m, 2H); $^{13}$C NMR (150 MHz, CDCl$_3$): 168.3, 142.2, 134.1, 134.0, 132.3, 128.8, 128.8, 123.5, 62.9, 41.5, 35.4, 32.4, 27.6.

To a solution of 2-methanesulfinyl-3-methyl-chromen-4-one (0.35 g, 1.78 mmol) in acetonitrile (37 mL), 4-(4-aminomethyl-phenyl)-butan-1-ol (0.47 g, 2.13 mmol) and DMF (18 mL) were added. The reaction stirred in a 50° C. oil bath overnight under N$_2$ atmosphere. The next day, the reaction mixture was cooled to room temperature and concentrated to yield an oil. Purification of the oil by flash column chromatography (100% ethyl acetate) afforded the desired product as a white solid (120 mg, 20% yield). $^1$H NMR (600 MHz, CDCl$_3$): δ 8.20 (d, 1H, J=7.9 Hz), 7.53 (t, 1H, J=7.8 Hz), 7.35 (t, 1H, J=7.6 Hz), 7.31 (d, 1H, J=8.4 Hz), 7.29 (d, 2H, J=7.9 Hz), 7.21 (d, 2H, J=7.9 Hz), 4.82 (bt, 1H, J=5.9 Hz), 4.66 (d, 2H, J=5.6 Hz), 3.68 (m, 2H), 2.66 (t, 2H, J=7.5 Hz), 1.97 (s, 3H), 1.70 (m, 2H), 1.61 (m, 2H), 1.24 (bt, 1H, J=5.3 Hz); $^{13}$C NMR (150 MHz, CDCl$_3$): δ 174.0, 160.3, 152.2, 141.4, 135.5, 130.7, 128.2, 126.9, 125.0, 123.8, 122.3, 115.8, 92.7, 61.5, 44.6, 34.8, 31.8, 27.2, 7.3.

EXAMPLE 16e

Synthesis of toluene-4-sulfonic acid 4-(4-[(3-methyl-4-oxo-4H-chromen-2-ylamino)-methyl]-phenyl)-butyl ester

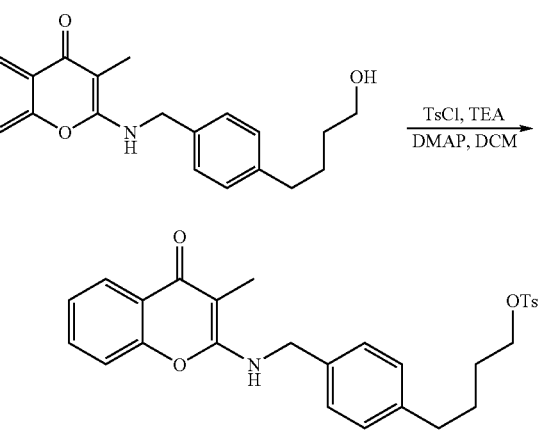

To a solution of 2-[4-(4-hydroxy-butyl)-benzylamino]-3-methyl-chromen-4-one (100 mg, 0.30 mmol) in dichloromethane (37 mL) was added p-toluenesulfonylchloride (68 mg, 0.36 mmol), dimethylaminopyridine (43.4 mg, 0.36 mmol), and triethylamine (62 μL, 0.44 mmol) in a 0° C. ice bath. The reaction slurry stirred overnight under N$_2$ atmosphere, warming to room temperature slowly overnight. The next day, the reaction mixture was concentrated and purified by flash column chromatography (3:1→1:1 Hexane:ethyl acetate→100% ethyl acetate) to obtain the product as an oil (45 mg, 31% yield). $^1$H NMR (600 MHz, CDCl$_3$): δ 8.19 (dd, 1H, J=1.5 and 7.9 Hz), 7.76 (d, 2H, J=8.3 Hz), 7.76 (m, 1H), 7.32 (d, 2H, J=7.9 Hz), 7.29 (d, 2H, J=8.1 Hz), 7.26 (d, 2H, J=8.0 Hz), 7.13 (d, 2H, J=8.0 Hz), 4.90 (t, 1H, J=5.1 Hz), 4.64 (d, 2H, J=5.6 Hz), 4.02 (t, 2H, J=5.9 Hz), 2.57 (t, 2H, J=7.3 Hz), 2.43 (s, 3H), 1.96 (s, 3H), 1.65 (m, 4H); $^{13}$C NMR (150 MHz, CDCl$_3$): δ 174.9, 160.2, 152.8, 144.7, 141.5, 135.4, 133.1, 131.4, 129.8, 128.9, 127.9, 127.7, 125.9, 124.6, 122.8, 116.2, 93.4, 70.3, 45.5, 34.7, 28.4, 27.1, 21.6, 7.6.

EXAMPLE 16f

Synthesis of 2-[4-(4-Fluoro-butyl)-benzylamino]-3-methyl-chromen-4-one

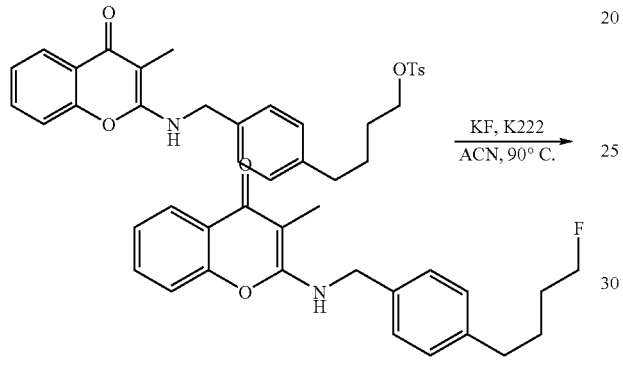

To a solution of toluene-4-sulfonic acid 4-{4-[(3-methyl-4-oxo-4H-chromen-2-ylamino)-methyl]-phenyl}-butyl ester (24 mg, 0.049 mmol) in ACN (1.1 mL) was added K222 (37 mg, 0.098 mmol) followed by KF (6 mg, 0.098 mmol). The reaction stirred in a 90° C. oil bath for 30 minutes under nitrogen atmosphere, monitored by LC-MS. The reaction was then cooled to room temperature and injected directly onto the preparative HPLC coloum chromatography (Luna, 10u, C18, 250×21.2 mm 10 micro, 60% of water in 90% acetonitrile in water with 0.1% TFA as the modifier in both mobile phases). The desired fractions were collected and neutralized to pH 7.6, then lyophilized. The material was re-purified by flash column chromatography (3:1 Hexane:ethyl acetate) to obtain the desired product as a solid (0.3 mg, <2% yield).

$^1$H NMR (600 MHz, CDCl$_3$/DMSO-d$_6$): δ 8.03 (m, 1H), 7.35 (m, 1H), 7.16 (m, 4H), 7.07 (m, 2H), 4.52 (m, 2H), 4.35 (m, 1H), 4.27 (m, 1H), 2.58 (m, 2H), 1.75 (s, 3H), 1.24 (m, 4H).

EXAMPLE 17

EXAMPLE 17a

Synthesis of 3-Methyl-2-methylsulfanyl-chromen-4-one

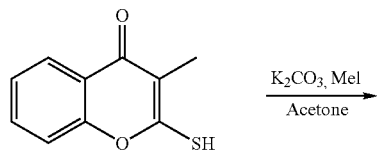

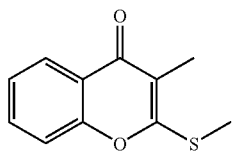

To a solution containing 2-mercapto-3-methyl-chromen-4-one (2.26 g, 11.76 mmol) and potassium carbonate (1.62 g, 11.76 mmol) in acetone (120 mL) was added iodomethane (807 μL, 12.93 mmol). The reaction stirred under nitrogen atmosphere at room temperature for 16 hours before being concentrated to yield a crude oil. The residue was taken up in water and adjusted to pH 7 with 5% HCl. The resulting aqueous layer was washed with ethyl acetate. The the organic layer was then washed with water and brine, dried over sodium sulfate, filtered, and concentrated to obtain the desired product as a yellow solid (1.95 g, 80% yield), which was taken on to the next step without further purification. $^1$H NMR (600 MHz, CDCl$_3$): δ 8.21 (d, 1H, J=6.6 Hz), 7.61 (m, 1H), 7.38 (m, 2H), 2.66 (s, 3H), 2.09 (s, 3H).

EXAMPLE 17b

Synthesis of 2-Methanesulfinyl-3-methyl-chromen-4-one

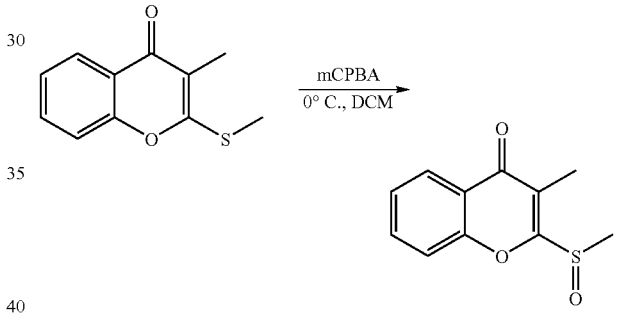

To a solution containing 3-methyl-2-methylsulfanyl-chromen-4-one (1.95 g, 9.45 mmol) in dichloromethane (75 mL) at 0° C. was added mCPBA (2 g, 11.82 mmol). The reaction stirred for 2 hours. After consumption of the starting material, the reaction mixture was filtered and the resulting filtrate was washed with cold 5% sodium carbonate, water, and saturated sodium bisulfate. The organic layer was dried over sodium sulfate, filtered, and concentrated to obtain the desired product as a light yellow solid (1.74 g, 83% yield), which was taken on to the next step without further purification. $^1$H NMR (600 MHz, DMSO-d$_6$): δ 8.08 (dd, 1H, J=7.8, 1.2 Hz), 7.88 (m, 1H), 7.76 (d, 1H, J=7.8 Hz), 7.55 (m, 1H), 3.01 (s, 3H), 2.12 (s, 3H).

EXAMPLE 17c

Synthesis of 2-Methanesulfonyl-3-methyl-chromen-4-one

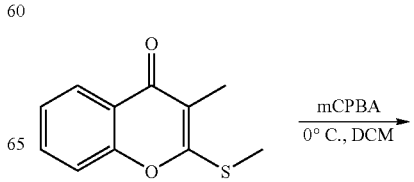

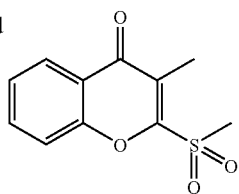

To a solution containing 3-methyl-2-methylsulfanyl-chromen-4-one (2.39 g, 11.6 mmol) in dichloromethane (75 mL) at 0° C. was added mCPBA (4 g, 11.82 mmol). The reaction stirred for 2 hours. After consumption of the starting material, the reaction mixture was filtered and the resulting filtrate was washed with cold 5% sodium carbonate, water, and saturated sodium bisulfate. The organic layer was dried over sodium sulfate, filtered, and concentrated to obtain the desired product as a light yellow solid (0.685 g, 33% yield), which was taken on to the next step without further purification. $^1$H NMR (600 MHz, CDCl$_3$): δ 8.22 (d, 1H, J=3.0 Hz), 7.76 (m, 1H), 7.52 (d, 1H, J=8.4 Hz), 7.48 (m, 1H), 3.31 (s, 3H), 2.46 (s, 3H).

EXAMPLE 18

EXAMPLE 18a

Synthesis of (4-hydroxy-3,5-dimethoxy-phenyl)-acetic acid methyl ester

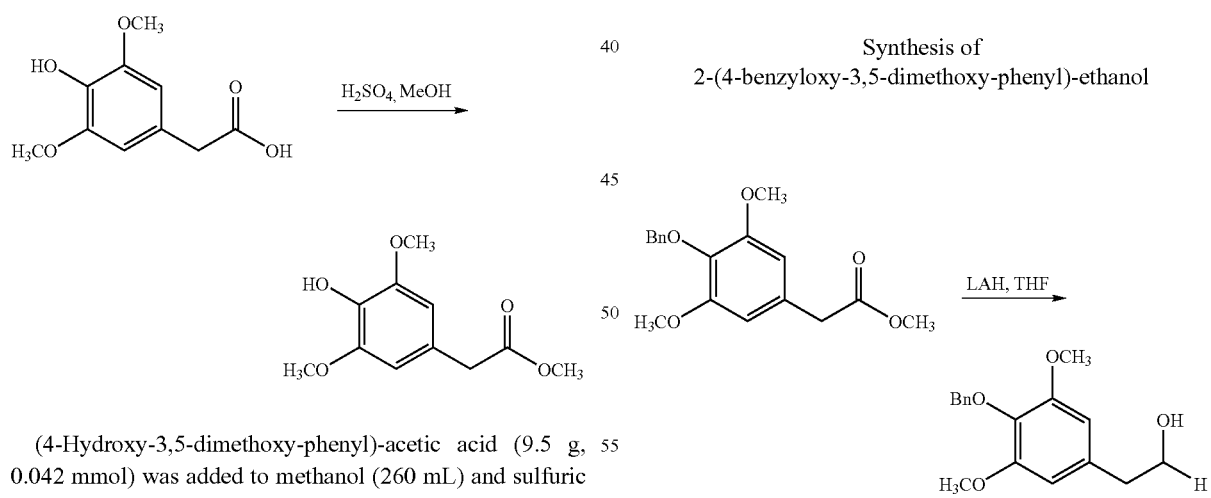

(4-Hydroxy-3,5-dimethoxy-phenyl)-acetic acid (9.5 g, 0.042 mmol) was added to methanol (260 mL) and sulfuric acid (8 mL). After completion of addition the reaction was heated at reflux overnight. The next day, the reaction mixture was cooled down and concentrated to yield a crude oil. The oil was re-dissolved in ethyl acetate, washed with water, brine, and dried over sodium sulfate, and filtered to be concentrated again. The crude material was purified using silica gel chromatography (50%:50% ethyl acetate:pentane) to yield the desired product (1.5 g, 75% yield based on recovered starting material).

EXAMPLE 18b

Synthesis of (4-benzyloxy-3,5-dimethoxy-phenyl)-acetic acid methyl ester

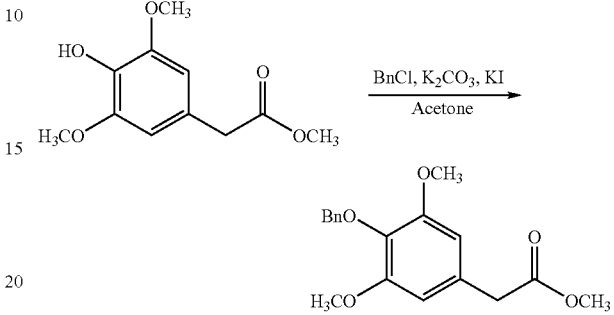

To a solution of (4-hydroxy-3,5-dimethoxy-phenyl)-acetic acid methyl ester (4.1 g, 18.1 mmol) in acetone (50 mL) was added potassium carbonate (1.39 g, 10.1 mmol) benzyl chloride (3.58 g, 28.28 mmol) and potassium iodide (catalytic amount). After completion of addition the reaction mixture was heated to reflux overnight. The next day, the reaction was cooled down to room temperature and diluted with water. The aqueous layer was extracted with ethyl acetate. All combined organic layers were dried over sodium sulfate, filtered, and concentrated. The crude material was purified using silica gel chromatography (gradient 100% pentane to 100% ethyl acetate) to afford the desired compound (1.5 g, 26%).

EXAMPLE 18c

Synthesis of 2-(4-benzyloxy-3,5-dimethoxy-phenyl)-ethanol (4-Benzyloxy-3,5-dimethoxy-phenyl)-acetic acid methyl ester (3.57 g, 11.3 mmol) was dissolved in THF (113 mL). A solution of LAH (1M in THF, 11.3 mL) was added dropwise to the stirring reaction mixture. After completion of addition the reaction continued to stir at room temperature overnight. The next day, the reaction was quenched with water. The aqueous layer was extracted with ethyl acetate. All of the combined organic layers were dried over sodium sulfate,

EXAMPLE 18d

Synthesis of (4-benzyloxy-3,5-dimethoxy-phenyl)-acetaldehyde

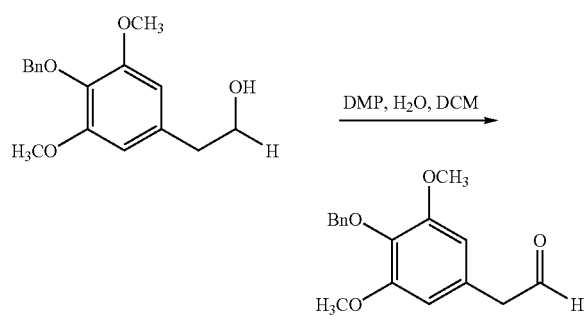

To a solution of 2-(4-benzyloxy-3,5-dimethoxy-phenyl)-ethanol (1.0 g, 3.3 mmol) in dichloromethane (25 mL) was added Dess-Martin reagent (1.54 g, 3.6 mmol) and water (59 µL). After completion of addition the reaction continued to stir for 6 hours. The resulting precipitate was filtered off and the filtrate was concentrated. The crude material was purified using silica gel chromatography (gradient from 1:2 ethyl acetate:hexane to 1:1 ethyl acetate:hexane) to obtain the desired compound as a yellow oil (547 mg, 55%).

EXAMPLE 18e

Synthesis of 2-(4-benzyloxy-3,5-dimethoxy-phenyl)-1-(2,2-dimethyl-2H-chromen-6-yl)-ethanone

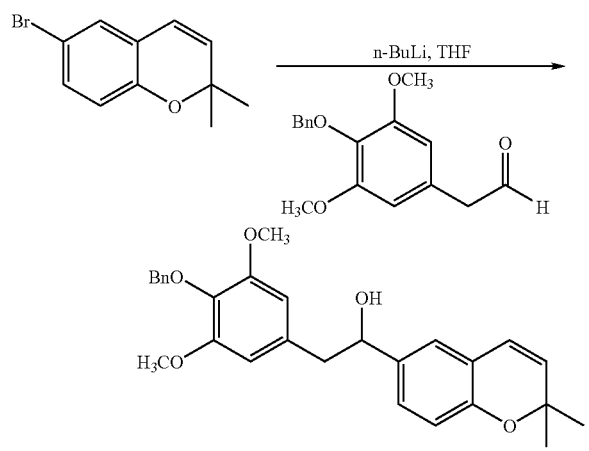

To a cooled (−78° C.) stirring solution of 6-bromo-2,2-dimethyl-2H-chromene, which was prepared according to *Chemistry and Biology*, 2000, Vol. 7, p. 979, (567.7 mg, 2.38 mmol) in THF (7 mL) was added n-BuLi (2.88 M, 0.94 mL, 2.71 mmol). After completion of addition, the reaction mixture continued to stir at −78° C. After 25 minutes, (4-benzyloxy-3,5-dimethoxy-phenyl)-acetaldehyde (619.6 mg, 2.17 mmol) dissolved in THF (7.0 mL) was added. After completion of addition the reaction continued to stir for 15 minutes and was then quenched with saturated ammonium chloride. The aqueous layer was separated and extracted with ethyl acetate. All Combined organic layers were dried over sodium sulfate, filtered, and concentrated to yield a crude oil. The crude material was purified by silica gel chromatography (3:1 ethyl acetate:hexanes) to yield the desired product (200.5 mg, 20% yield).

EXAMPLE 18f

Synthesis of -(4-benzyloxy-3,5-dimethoxy-phenyl)-]-(2,2-dimethyl-2H-chromen-6-yl)-ethanone

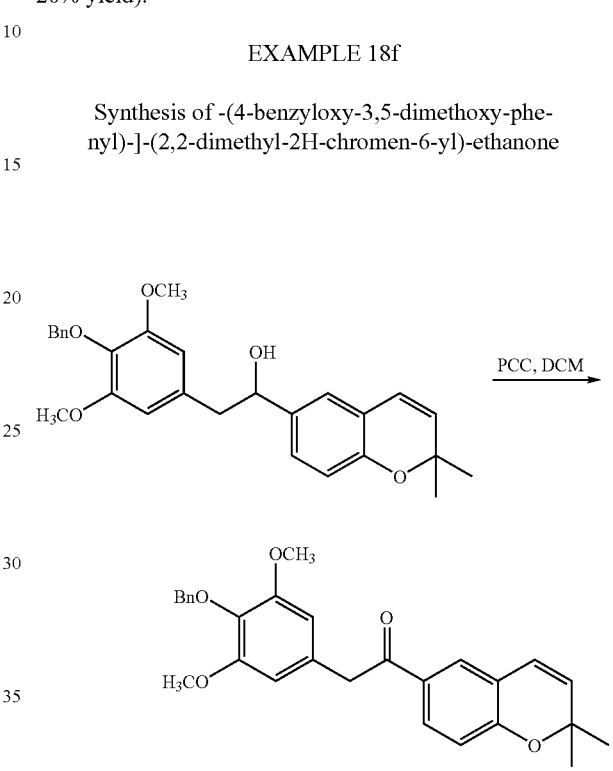

2-(4-benzyloxy-3,5-dimethoxy-phenyl)-1-(2,2-dimethyl-2H-chromen-6-yl)-ethanone (119.4 mg, 0.27 mmol) dissolved in dichloromethane (2 mL) was added dropwise to a stirring solution of PCC (69.2 mg, 0.27 mmol) in dichloromethane (6.0 mL). After 3.5 h the reaction mixture was poured onto a pre-saturated silica gel plug (1:2 hexane:ethyl acetate), which was washed with a 1:1 ethyl acetate:hexane mixture to collect the desired compound as a yellow oil (167 mg, 97% yield).

EXAMPLE 18g

Synthesis of 1-(2,2-dimethyl-chroman-6-yl)-2-(4-hydroxy-3,5-dimethoxy-phenyl]-ethanone

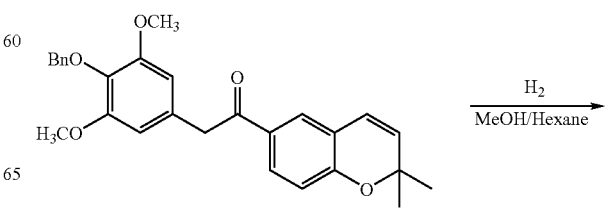

-continued

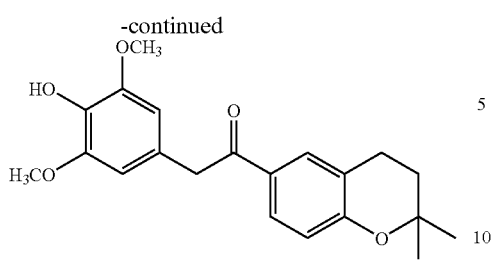

To a solution of 2-(4-benzyloxy-3,5-dimethoxy-phenyl)-1-(2,2-dimethyl-2H-chromen-6-yl)-ethanone (62.8 mg) dissolved in methanol (5.0 mL) and hexanes (3.3 mL) was added palladium on carbon (19.13 mg, 10% on carbon). The reaction mixture was purged with nitrogen numerous times before being exposed to a hydrogen atmosphere. Hydrogenation proceeded at room temperature and at atmospheric pressure. After 15 minutes, the reaction was purged again with nitrogen and the reaction mixture was filtered to remove the catalyst. The filtrate was concentrated to yield the desired product.

EXAMPLE 18h

Synthesis of 1-(2,2-dimethyl-chroman-6-yl)-2-[4-(2-fluoro-ethoxy)-3,5-dimethoxy-phenyl]-ethanone

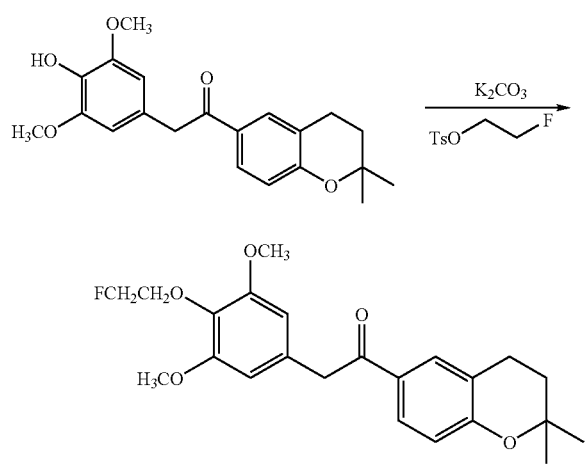

To a solution of 1-(2,2-dimethyl-chroman-6-yl)-2-(4-hydroxy-3,5-dimethoxy-phenyl]-ethanone (5.0 mg, 0.014 mmol) in DMF (1.4 mL) was added potassium carbonate (1N (aq.), 21.1 µL, 0.021 mmol) followed by fluoroethyl tosylate (6.12 mg, 0.028 mmol). After completion of addition the reaction mixture was heated to 90° C. After 1 hour, the reaction mixture was cooled down to room temperature. Water was added to the cooled reaction mixture and the aqueous layer was extracted with ethyl acetate. All combined organic layers were dried over sodium sulfate, filtered, and concentrated to yield a yellow oil. Purification by reverse phase chromatography (Luna, 10u, C18, 150×21.2 mm, 10 micro, solvent system:70% of a 90% acetonitrile in water solution: 30% of water using 01% of TFA in both mobile phases) afforded the desired compound (1.05 mg, 19% yield).

EXAMPLE 19

EXAMPLE 19a

Synthesis of [1-(2,2-dimethyl-chroman-6-yl)-2-(3,4,5-trimethoxy-phenyl)-vinyloxy]-trimethyl-silane

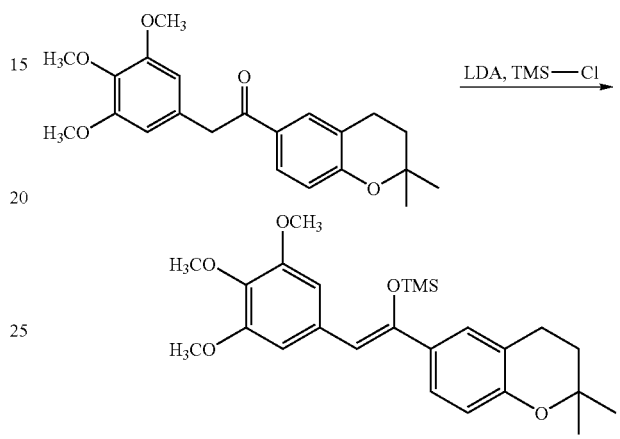

i-Pr$_2$NH (0.556 mL, 4.04 mmol), distilled from CaH, was added to THF (7 mL) and cooled to −78° C. A solution of n-BuLi (2.59 M in THF, 1.56 mL, 4.04 mmol) was added dropwise. After completion of addition the reaction mixture stirred at −30° C. for 35 minutes and then cooled down again to −78° C. TMS-Cl (0.546 mL) and 1-(2,2-dimethyl-chroman-6-yl)-2-(3,4,5-trimethoxy-phenyl)-ethanone (1.20 g, 3.23 mmol) dissolved in THF (25 mL) were added dropwise to the stirring reaction mixture. After completion of addition the reaction mixture continued stirring at −78° C. for an additional 30 minutes before being warmed up to −30° C. After stirring at −30° C. for 1 hour the reaction was diluted with diethyl ether and warmed to room temperature. At room temperature the reaction mixture was concentrated and the resulting crude material was purified using silica gel chromatography (4:1 pentane: ethyl acetate to 1:1 pentane: ethyl acetate) to obtain the desired compound (879.1 mg, 74% yield based on recovered starting material).

EXAMPLE 19b

Synthesis of [1-(2,2-dimethyl-chroman-6-yl)-2-(3,4,5-trimethoxy-phenyl)-ethanone

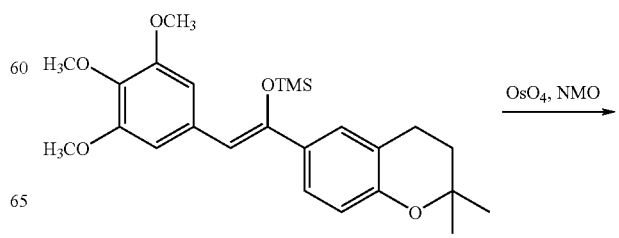

-continued

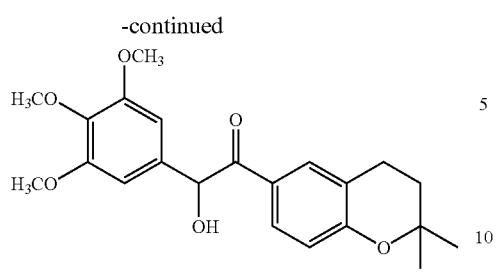

A solution of osmium tetroxide (25% wt., 0.574 mL) and NMO (13.24 mg, 0.113 mmol) dissolved in water (0.27 mL) and acetone (0.48 mL) were cooled to −5° C. [1-(2,2-dimethyl-chroman-6-yl)-2-(3,4,5-trimethoxy-phenyl)-vinyloxy]-trimethyl-silane (50 mg, 0.113 mmol) dissolved in acetone (0.2 mL) was added dropwise to the cooled stirring solution. After completion of addition the reaction continued to stir at 0° C. After 3 h, the reaction was quenched with sodium hydrosulfite and florisil. The reaction mixture was filtered and the filtrate was concentrated. The crude material was purified using silica gel chromatography (4:1 pentane: ethyl acetate to 1:1 pentane ethyl acetate) to afford the desired compound (4.3 mg, 8%).

EXAMPLE 19c

Synthesis of toluene-4-sulfonic acid 2-(2,2-dimethyl-chroman-6-yl)-2-oxo-1-(3,4,5-trimethoxy-phenyl)-ethyl ester

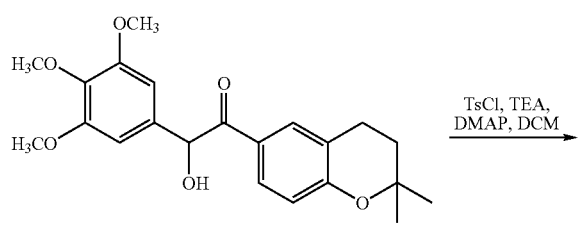

To a solution [1-(2,2-dimethyl-chroman-6-yl)-2-(3,4,5-trimethoxy-phenyl)-ethanone (3.4 mg, 0.009 mmol) dissolved in anhydrous dichloromethane (1.0 mL) is added TsCl (1.94 mg, 0.011 mmol), DMAP (1.24 mg, 0.011 mmol) and TEA (21.3 µL, 0.015 mmol). The reaction mixture continues stirring at room temperature overnight. The next day, the reaction mixture is diluted with water. The aqueous layer is separated and extracted with ethyl acetate (3×). All combined organic layers are dried over $Na_2SO_4$, filtered, and concentrated to yield an oil. The crude material is purified using silica gel chromatography to yield the desired product.

EXAMPLE 19d

Synthesis of 1-(2,2-dimethyl-chroman-6-yl)-2-fluoro-2-(3,4,5-trimethoxy-phenyl)-ethanone

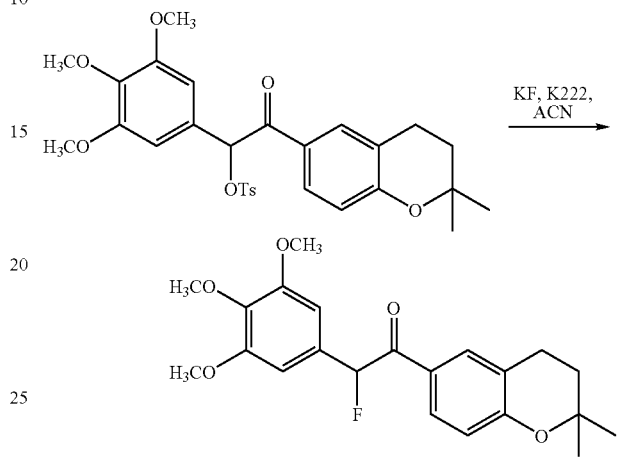

To a solution of toluene-4-sulfonic acid 2-(2,2-dimethyl-chroman-6-yl)-2-oxo-1-(3,4,5-trimethoxy-phenyl)-ethyl ester (21.6 mg, 0.04 mmol) in anhydrous ACN (0.5 mL) is added KF (4.72 mg, 0.08 mmol) and Kryptofix (30.6 mg, 0.08 mmol). After completion of addition the reaction mixture is heated to 90° C. After 15 minutes, the reaction mixture is cooled down to room temperature and diluted with water. The aqueous layer is separated and extracted with ethyl acetate (3×). All combined organic layers are dried over $Na_2SO_4$, filtered, and concentrated to yield an oil. The crude material is purified using reverse phase to yield the desired compound.

EXAMPLE 20

EXAMPLE 20a

Synthesis of 7-bromo-3,3-dimethyl-chroman-4-one

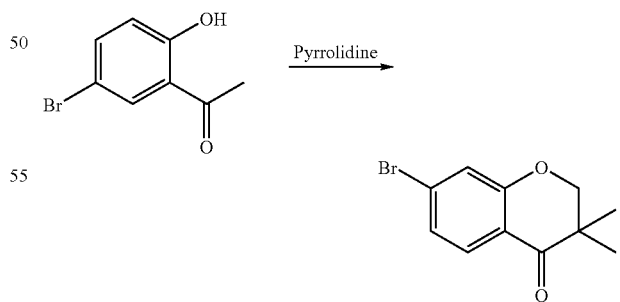

5'-bromo-2'hydroxyacetophenone was dissolved in acetone (8.45 mL) and toluene (43 mL). Pyrrolidine (1.90 mL) was added dropwise to the stirring reaction mixture. After completion of addition the reaction mixture was heated at reflux. The next day, the reaction mixture was cooled to room temperature and washed with 2M HCl (aqueous), dried over sodium sulfate, filtered, and concentrated. The crude material was purified using silica gel chromatography (90:10 pentane:diethyl ether) to yield the desired product (3.11 g, 53% yield).

EXAMPLE 20b

Synthesis of 7-bromo-3,3-dimethyl-chroman-4-ol

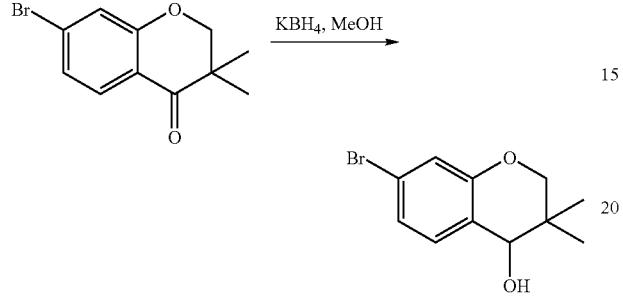

To a cooled (0° C.) solution of 7-bromo-3,3-dimethyl-chroman-4-one (1.5 g, 5.91 mmol) in methanol (17 mL) was added potassium borohydride (0.351 g, 6.5 mmol). After completion of addition the reaction stirred at room temperature for 2 hours and was then quenched with 2M HCl (aq.). The aqueous layer was extracted with ethyl acetate (3×) The combined organic layers were dried over sodium sulfate, filtered, and concentrated to yield an off-white solid, which was used in the next step without further purification.

EXAMPLE 20c

Synthesis of (7-bromo-3,3-dimethyl-chroman-4-yloxy)-tert-butyl-dimethyl-silane

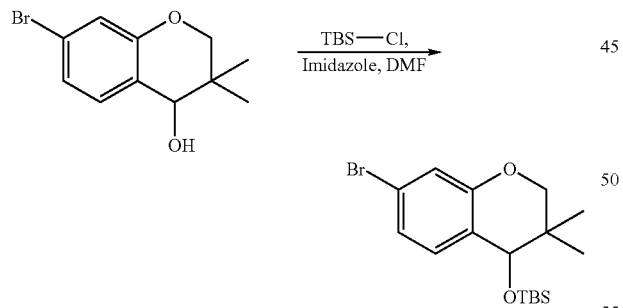

To a solution of 7-bromo-3,3-dimethyl-chroman-4-ol (300 mg, 1.44 mmol) in DMF (3.33 mL) was added imidazole (119 mg, 1.75 mmol) followed by TBDMS-Cl (263 mg, 1.75 mmol). The next day, the reaction was diluted with ethyl acetate and washed with water (3×) and saturated sodium bicarbonate (1×). The organic layer was dried over sodium sulfate, filtered, and concentrated. The crude material was purified using silica gel chromatography (100% pentane to 50% pentane in ethyl acetate) to yield the desired product (290 g, 65% yield).

EXAMPLE 20d

Synthesis of 1-[(4-tert-butyl-dimethyl-silanyloxy)-benzyloxy-(2,2-dimethyl-2H-chroman-6-yl]-2-(3, 4, 5-trimethoxy-phenyl)-ethanone

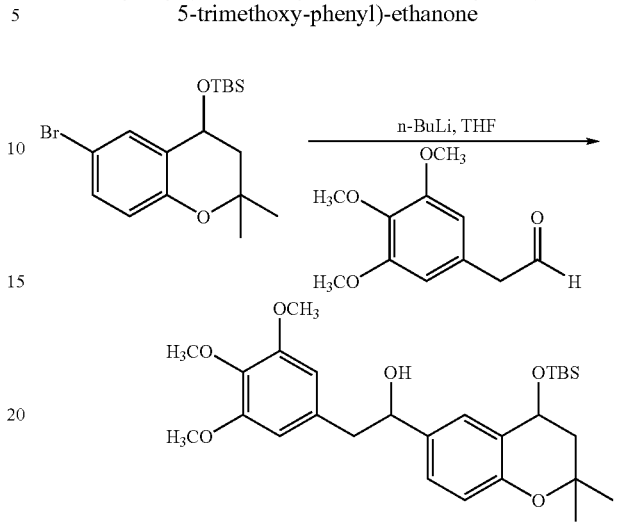

To a cooled (−78° C.) stirring solution of (7-bromo-3,3-dimethyl-chroman-4-yloxy)-tert-butyl-dimethyl-silane (290 mg, 0.78 mmol) in THF (3.75 mL) was added n-BuLi (2.11 M, 0.42 mL, 0.89 mmol). After completion of addition, the reaction mixture continues to stir at −78° C. After 25 minutes, (3,4,5-trimethoxyphenyl)-acetaldehyde (149 mg, 0.71 mmol) dissolved in THF (0.41 mL) was added. After completion of addition the reaction continues to stir for 15 minutes and was then quenched with saturated ammonium chloride. The aqueous layer was separated and extracted with ethyl acetate. All combined organic layers were dried over sodium sulfate, filtered, and concentrated to yield a crude oil. The crude material was purified by silica gel chromatography (1:1 ethyl acetate:hexanes) to yield the desired product (50 mg, 14% yield).

EXAMPLE 20e

Synthesis of 1-[4-(terst-butyl-dimethyl-silanyloxy)-2,2-dimethyl-chroman-6-yl]-2-(3,4, 5 trimethoxy-phenyl)-ethanone

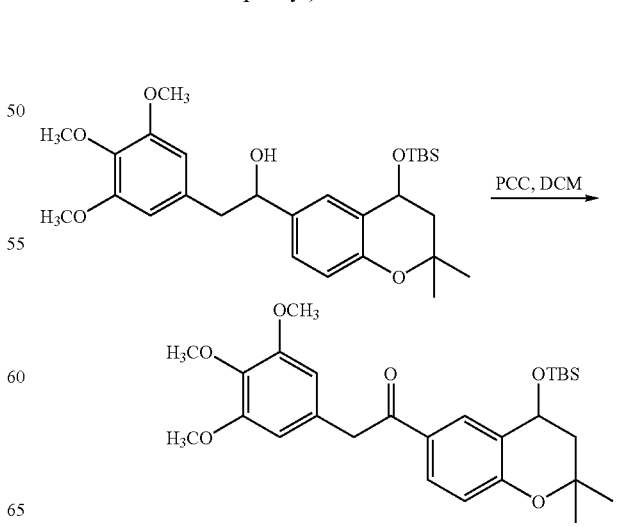

1-[(4-Tert-butyl-dimethyl-silanyloxy)-benzyloxy-(2,2-dimethyl-2H-chroman-6-yl]-2-(3,4,5-trimethoxy-phenyl)-ethanone (50 mg, 0.01 mmol) dissolved in dichloromethane (2.5 mL) was added dropwise to a stirring solution of PCC (23.6 mg, 0.11 mmol) in dichloromethane (2.5 mL). After 2 hours the reaction mixture was poured onto a pre-saturated silica gel plug (100% pentane), which was washed with a 1:1 ethyl acetate:hexane mixture followed by a wash of 100% ethyl acetate to collect the desired compound as an oil.

EXAMPLE 20f

Synthesis of 1-(4-hydroxy-2,2-dimethyl-chroman-6-yl)-2-(3,4,5-trimethoxy-phenyl)-ethanone

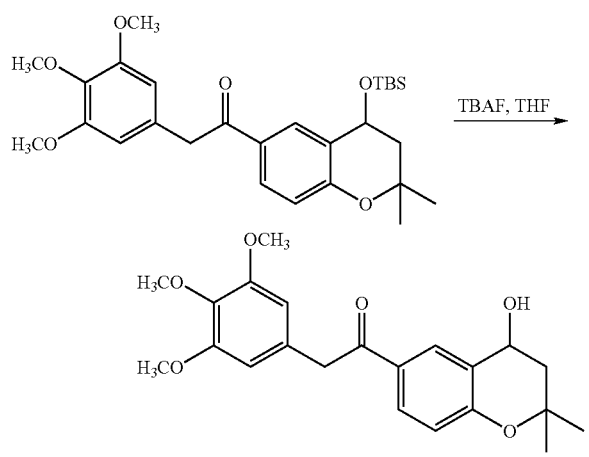

To a solution of 1-[4-(terst-butyl-dimethyl-silanyloxy)-2,2-dimethyl-chroman-6-yl]-2-(3,4,5 trimethoxy-phenyl)-ethanone (54.5 mg, 1.09 mmole) dissolved in anhydrous THF (11 mL) is added a solution of TBAF (1.0 M solution in THF, 1.65 mL, 1.65 mmole) dropwise. After completion of addition the reaction is stirred a room temperature for 1 hour and then quenched with water. The aqueous layer is separated and extracted with ethyl acetate (3×). All combined organic layers are dried over $Na_2SO_4$, filtered, and concentrated to yield an oil. The crude material is purified using silica gel chromatography to yield the desired compound.

EXAMPLE 20g

Synthesis of toluene-4-sulfonic acid 2,2-dimethyl-6-[2-(3,4,5-trimethoxy-phenyl)-acetyl]-chroman-4-yl ester

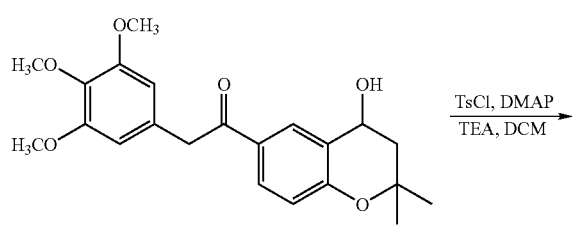

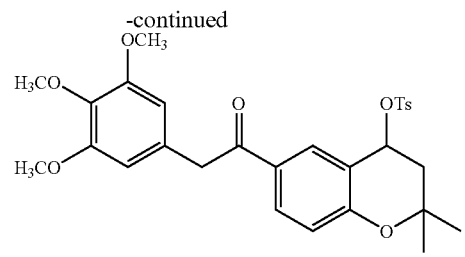

To a solution 1-(4-hydroxy-2,2-dimethyl-chroman-6-yl)-2-(3,4,5-trimethoxy-phenyl)-ethanone (3.5 mg, 0.009 mmol) dissolved in anhydrous dichloromethane (1.0 mL) is added TsCl (1.94 mg, 0.011 mmol), DMAP (1.24 mg, 0.011 mmol) and TEA (21.3 µL, 0.015 mmole). The reaction mixture continues stirring at room temperature overnight. The next day, the reaction mixture is diluted with water. The aqueous layer is separated and extracted with ethyl acetate (3×). All combined organic layers are dried over $Na_2SO_4$, filtered, and concentrated to yield an oil. The crude material is purified using silica gel chromatography to yield the desired product.

EXAMPLE 20h

Synthesis of 1-(4-fluoro-2,2-dimethyl-chroman-6-yl)-2-(3,4,5-trimethyoxy-phenyl)-ethanone

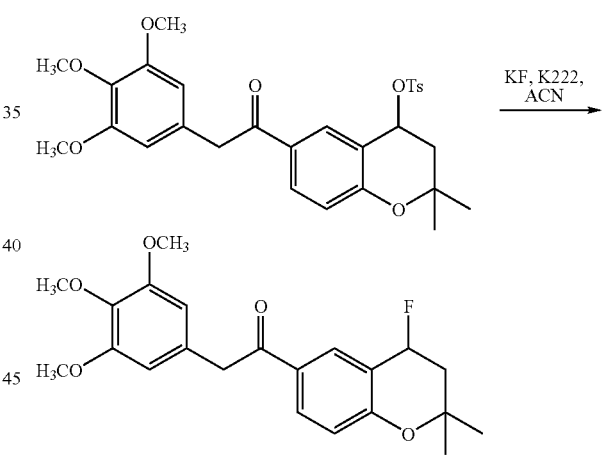

To a solution of toluene-4-sulfonic acid 2-(2,2-dimethyl-chroman-6-yl)-2-oxo-1-(3,4,5-trimethoxy-phenyl)-ethyl ester (21.6 mg, 0.04 mmol) in anhydrous ACN (0.5 mL) is added KF (4.72 mg, 0.08 mmol) and Kryptofix (30.6 mg, 0.08 mmol). After completion of addition the reaction mixture is heated to 90° C. After 15 minutes, the reaction mixture is cooled down to room temperature and diluted with water. The aqueous layer is separated and extracted with ethyl acetate (3×). All combined organic layers are dried over $Na_2SO_4$, filtered, and concentrated to yield an oil. The crude material is purified using reverse phase to yield the desired compound.

Radiosynthetic and Purification Procedures for Preparation of Chromone Analogs Radiolabeled with the Fluorine-18 Radionuclide.

The Fluorine-18 ($^{18}F$) used in the research was produced via the proton bombardment of enriched Oxygen-18 ($^{18}O$) as H$_2$$^{18}$O with using approximately 10 MeV protons by PETnet (Woburn, Mass.). The expression for this nuclear reaction is: O$^{18}$(p,γ) $^{18}$F.

For all of the radiosynthetic reactions a similar procedure was used. All glassware was silanized to preclude adhesion of the material to the vessel walls and optimize transfers. A dedicated, specific HPLC unit was used for purification for all compounds. A dedicated specific HPLC unit was used for radioanalytical analyses of final product.

The $^{18}$F typically was received from the supplier deposited on a processed column ($^{18}$F column) encased in lead shielding. The $^{18}$F column contained the sodium salt coordinated to either alumina or a quaternary ammonium salt housed in a glass column. The column ends are connected to Tygon™ tubing with male and female Luer™ lock fittings. The $^{18}$F is removed from the column using the following method.

1. A solution of 15 mg of potassium carbonate (K$_2$CO$_3$) in 1 mL of distilled/deionized water (H$_2$O) and a solution of 90 mg of 4,7,13,16,21,24-hexaoxa-1,10-diazabicyclo[8.8.8] hexacosane (Kryptofix™; K222) dissolved in 4 mL of anhydrous acetonitrile (CH$_3$CN) were combined and gently stirred, ensuring the layers did not separate, forming the column eluting solution (CES).
2. A one mL aliquot of the CES was extracted from the vial described in step three using a 3 mL syringe and the syringe was attached to the male Luer™ lock of the Tygon™ tubing connected to the $^{18}$F column.
3. A narrow gauge needle was attached to the female Luer™ lock of the other Tygon™ tubing connected to the $^{18}$F column, and the needle was inserted through the rubber septum fitted to a 15 mL 24/40 Pyrex™ pear-shaped glass flask.
4. The 15 mL pear shaped flask was vented with a needle and the flask was flushed with dry nitrogen. The flushing needle was connected to a vacuum line and the flow adjusted such that CES was slowly drawn through the $^{18}$F column into the 15 mL pear-shaped flask.
5. The vacuum and N$_2$ gas flow were adjusted such that the contents of the flask were reduced to dryness. Anhydrous CH$_3$CN (1 mL) was added via syringe to the flask, using vacuum to drive the transfer. The vacuum and N$_2$ gas flow were balanced to remove the acetonitrile. This procedure was repeated twice, after which point the vacuum was removed.
6. The contents of the flask were removed via syringe and the radioactivity was quantified. The $^{18}$F solution was used directly in radiolabeling syntheses.

The next steps describe the radiolabeling of the chromone analogs with $^{18}$F. As previously stated these steps were the same for each of the compounds. The following reaction scheme depicts a representative scenario for all of the $^{18}$F-chromone analogs:

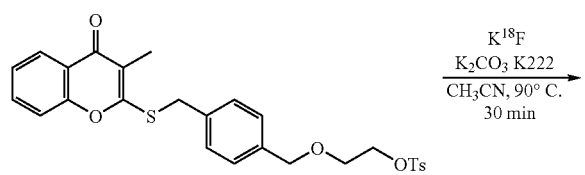

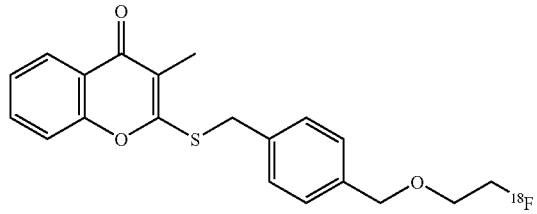

7. The toluenesulfonate ester precursor to the desired chromone analog (2.5 mg) was dissolved in CH$_3$CN (0.5 mL) in a conical silanized 5 mL Wheaton™ glass vial with a magnetic stirring bar. The vial was immersed in a oil bath heated at 90° C. The solution of the $^{18}$F described above was added to the reaction vial the resultant mixture was heated at 90° C. for 30 minutes.
8. The contents were transferred to a 50 mL silanized round bottom flask containing distilled/deionized water (25 mL), and the contents of the flask are removed via syringe, and deposited on a Waters™ Oasis HLB (hydrophilic-lipophilc balance) column, allowing unreacted fluoride and undesired salts to pass through with the eluate.
9. The organic components were eluted from the column into a conical 5 mL vial using dichloromethane, (3 mL, CH$_2$Cl$_2$). The eluant was purified via preparative HPLC (Phenomenex LUNA C-18 column 250×10 mm, 5u particle, 100A pore. gradient elution 90/10 H$_2$O/CH$_3$CN—CH$_3$CN). The appropriate fractions were concentrated and analyzed for radiochemical yield and radiochemical purity (analytical HPLC). The solution was concentrated to dryness in vacuo, and dissolved in the appropriate volume of 10% ethanolic saline for injection and/or biological studies.

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

What is claimed is:
1. A contrast agent of formula (IV)

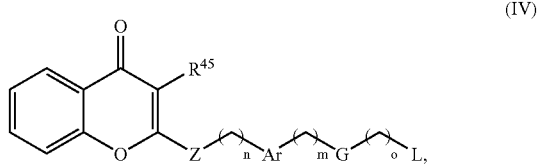

wherein
n, m, and o are independently 1, 2, 3, or 4;
Z is O, S, or NR$^{46}$;
R$^{45}$ is an imaging moiety or C$_1$-C$_4$ alkyl optionally substituted with an imaging moiety;
R$^{45}$ is hydrogen or C$_1$-C$_3$ alkyl;
Ar is phenyl, furyl, thienyl, oxazolinyl, isoxazolinyl, thiazolyl, isothiazolyl, pyridyl, naphthyl, pyrimidinyl, or pyrazinyl;

G is absent or O; and
L is an imaging moiety;
provided that when G is absent, o is 3.
2. A contrast agent which is
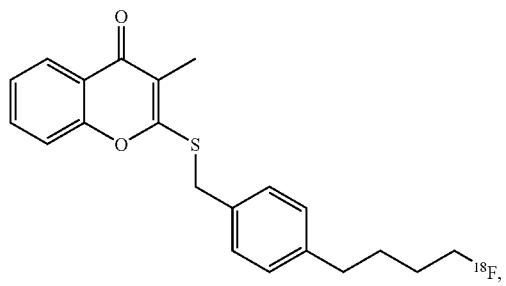
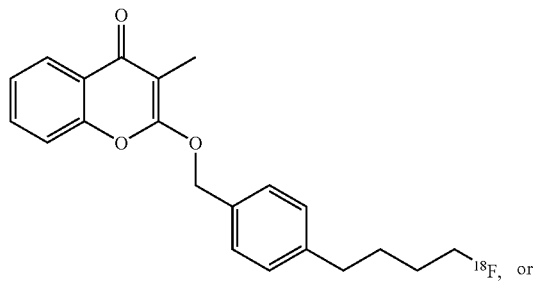, or
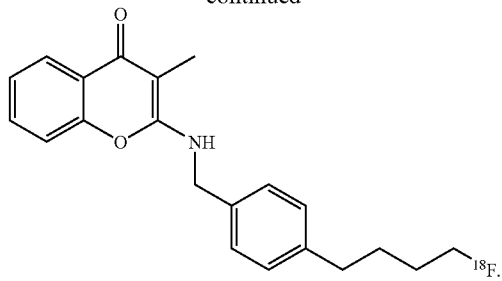
3. A contrast agent which is
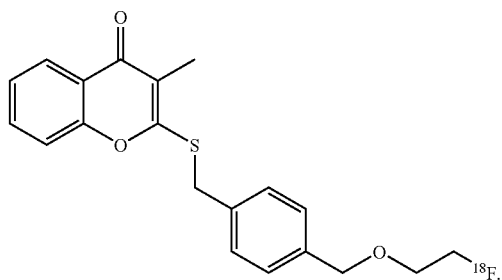
* * * * *

UNITED STATES PATENT AND TRADEMARK OFFICE
CERTIFICATE OF CORRECTION

PATENT NO. : 7,485,283 B2
APPLICATION NO. : 11/113486
DATED : February 3, 2009
INVENTOR(S) : Heike S. Radeke et al.

Page 1 of 1

It is certified that error appears in the above-identified patent and that said Letters Patent is hereby corrected as shown below:

Col. 105 in claim 1, the phrase "$R^{45}$ is hydrogen or…" should read "$R^{46}$ is hydrogen or…"

Signed and Sealed this

Sixteenth Day of June, 2009

JOHN DOLL
*Acting Director of the United States Patent and Trademark Office*

UNITED STATES PATENT AND TRADEMARK OFFICE
CERTIFICATE OF CORRECTION

PATENT NO. : 7,485,283 B2
APPLICATION NO. : 11/113486
DATED : February 3, 2009
INVENTOR(S) : Heike S. Radeke et al.

It is certified that error appears in the above-identified patent and that said Letters Patent is hereby corrected as shown below:

Col. 105 in claim 1, line 64, the phrase "$R^{45}$ is hydrogen or…" should read "$R^{46}$ is hydrogen or…"

This certificate supersedes the Certificate of Correction issued June 16, 2009.

Signed and Sealed this

Fourteenth Day of July, 2009

JOHN DOLL
*Acting Director of the United States Patent and Trademark Office*